(12) United States Patent
Fevre et al.

(10) Patent No.: US 9,951,179 B2
(45) Date of Patent: Apr. 24, 2018

(54) CYCLIC CARBONATE MONOMERS AND RING OPENED POLYCARBONATES THEREFROM

(71) Applicants: International Business Machines Corporation, Armonk, NY (US); Agency for Science, Technology and Research, Singapore (SG)

(72) Inventors: Mareva B. Fevre, San Jose, CA (US); James L. Hedrick, Pleasanton, CA (US); Victor W. L. Ng, Singapore (SG); Robert J. Ono, Seattle, WA (US); Shrinivas Venkataraman, Singapore (SG); Yi Yan Yang, Singapore (SG)

(73) Assignees: International Business Machines Corporation, Armonk, NY (US); Agency For Science, Technology And Research, Singapore (SG)

( * ) Notice: Subject to any disclaimer, the term of this patent is extended or adjusted under 35 U.S.C. 154(b) by 0 days.

(21) Appl. No.: 15/436,955

(22) Filed: Feb. 20, 2017

(65) Prior Publication Data
US 2017/0158811 A1    Jun. 8, 2017

Related U.S. Application Data

(60) Division of application No. 14/862,365, filed on Sep. 23, 2015, now Pat. No. 9,624,191, which is a continuation-in-part of application No. 14/223,630, filed on Mar. 24, 2014, now Pat. No. 9,215,876.

(51) Int. Cl.
| | | |
|---|---|---|
| *C07D 273/01* | (2006.01) | |
| *C08G 64/02* | (2006.01) | |
| *C07D 323/00* | (2006.01) | |
| *C08G 64/30* | (2006.01) | |
| *A01N 47/06* | (2006.01) | |
| *A01N 43/72* | (2006.01) | |

(52) U.S. Cl.
CPC ......... *C08G 64/0241* (2013.01); *A01N 47/06* (2013.01); *C07D 273/01* (2013.01); *C08G 64/30* (2013.01)

(58) Field of Classification Search
CPC  C07B 323/00; C07D 273/01; C08G 64/0241; C08G 64/30; A01N 43/72; A01N 47/06
See application file for complete search history.

(56) References Cited

U.S. PATENT DOCUMENTS

| | | |
|---|---|---|
| 2,824,857 A | 2/1958 | Drechsel |
| 3,422,119 A | 1/1969 | Prochask |
| 4,758,615 A | 7/1988 | Engel et al. |
| 4,879,367 A | 11/1989 | Piejko et al. |
| 4,965,335 A | 10/1990 | Smith |
| 5,097,009 A | 3/1992 | Fyvie et al. |
| 6,034,118 A | 3/2000 | Bischofberger et al. |
| 6,054,596 A | 4/2000 | Ohno et al. |
| 6,689,463 B2 | 2/2004 | Chou et al. |
| 6,808,804 B2 | 10/2004 | Hotaka et al. |
| 7,345,138 B2 | 3/2008 | Wang et al. |
| 7,943,141 B2 | 5/2011 | Harris et al. |
| 7,960,353 B2 | 6/2011 | Blagg |
| 8,044,194 B2 | 10/2011 | Dubois et al. |
| 8,071,082 B2 | 12/2011 | Zugates et al. |
| 8,212,012 B2 | 7/2012 | Blagg |
| 8,247,520 B2 | 8/2012 | Allen et al. |
| 2004/0030093 A1 | 2/2004 | Sakurai et al. |
| 2008/0124532 A1 | 5/2008 | Menovcik et al. |
| 2009/0306275 A1 | 12/2009 | Inagaki |
| 2010/0035359 A1 | 2/2010 | Cormack et al. |
| 2010/0331234 A1 | 12/2010 | Mahon et al. |
| 2011/0008277 A1 | 1/2011 | Bruggeman et al. |
| 2012/0172574 A1 | 7/2012 | Helou et al. |

FOREIGN PATENT DOCUMENTS

| | | |
|---|---|---|
| EP | 0 476 786 A2 * | 3/1992 |
| EP | 2 387 986 A2 * | 11/2011 |

OTHER PUBLICATIONS

Nishiyama et al., in the Journal of hetrocyclic Chemistry, vol. 22, pp. 445 and 446, 1985.*
de Santis et al. "Optically pure 3,6-Dioxazocan-2-one Derivatives by intramolecular Cycloaddtion of Azidoformates and their opening to substituted alpha-Amino Ketones," in European Journal of Organic Chemistry, 1992 2709-2711.*
Burke, et al., "A Safe and Efficient Method for Conversion of 1,2- and 1,3-Diols to Cyclic Carbonates Utilizing Triphosgene," Tetrahedron Letters, vol. 34, No. 3. 395-398 (1993).
Kataoka et al., "Block copolymer micelles for drug delivery: design, characterization and biological significance," Advanced Drug Delivery Reviews 47 (2001) 113-131.
Kojima, et al., "Synthesis of Polyamidoamine Dendrimers Having Poly(ethylene glycol) Grafts and Their Ability to Encapsulate Anticancer Drugs," Bioconjugate Chem. 2000, 11, 910-917.
Li, et al., "PEGylated PLGA nanoparticles as protein carriers: synthesis, preparation and biodistribution in rats," Journal of Controlled Release 71 (2001) 203-211.
Nishiyama, et al., "Mass Spectral Fragmentation of 6-Phenyl-5,6,7,8-tetrahydro-4H-1,3,6-dioxazocin-2-ones", J. Heterocyclic Chem., 1985, 22, pp. 445-446.

(Continued)

*Primary Examiner* — Blessing M Fubara
(74) *Attorney, Agent, or Firm* — Michael R. Roberts

(57) ABSTRACT

Eight-membered ring cyclic carbonates having an oxygen or an acylated nitrogen at position 6 were prepared by reaction of precursor diols with ethyl chloroformate. The cyclic carbonates undergo organocatalyzed ring opening polymerization. In one instance, the initial polymer formed comprises a carbonate repeat unit having a Boc-protected nitrogen in the polymer backbone. Deprotecting the nitrogen with acid forms a cationic carbonate repeat unit having a positive charged secondary ammonium nitrogen in the polymer backbone.

12 Claims, 12 Drawing Sheets

(56) References Cited

OTHER PUBLICATIONS

Nishiyama, et al., "The Conformational Analysis of a Series of 4,8-Dimethyl-6-phenyl-5,6,7,8-tetrahydro-4H-1,3,2,6-dioxathiazocine 2-Oxides Using NMR," Bull. Chem. Soc. Jpn., 54, 1410-1414 (1981).

Nishiyama, et al., "The Stereochemistry of 4,8-Dimethyl-6-phenyl-5,6,7,8-tetrahydro-4H-1,3,6-dioxazocine-2-ones Using NMR," J. Heterocyclic Chem. 21, 1145 (1984).

Ong, et al., "Rational design of biodegradable cationic polycarbonates for gene delivery", Journal of Controlled Release 152 (2011) 120-126.

Sanders, et al., "A Simple and Efficient Synthesis of Functionalized Cyclic Carbonate Monomers Using a Versatile Pentafluorophenyl Ester Intermediate," J. Am. Chem. Soc. 2010, 132, 14724-14726; Published on Web Sep. 30, 2010.

USPTO, non-final office action, dated Oct. 3, 2016, for U.S. Appl. No. 14/862,365, first inventor Mareva B. Fevre, filed Sep. 23, 2015.

Venkataraman, et al., "A Simple and Facile Approach to Aliphatic NSubstituted Functional Eight-Membered Cyclic Carbonates and Their Organocatalytic Polymerization", J. Am. Chem. Soc., 2015, 137 (43), pp. 13851-13860; Publication Date (Web): Oct. 12, 2015.

Wang, et al., "Biocatalytic Fabrication of Fast-Degradable, Water-Soluble Polycarbonate Functionalized with Tertiary Amine Groups in Backbone," Biomacromolecules 2010, 11, 2550-2557; Published on Web Sep. 13, 2010.

Xu, et al., "A Versatile Monomer for Preparing Well-Defined Functional Polycarbonates and Poly(ester-carbonates)," Macromolecules 2011, 44, 2660-2667; Published: Mar. 23, 2011.

* cited by examiner

CYCLIC CARBONATE MONOMERS AND RING OPENED POLYCARBONATES THEREFROM

PARTIES TO A JOINT RESEARCH AGREEMENT

This invention was made under a joint research agreement between International Business Machines Corporation and the Agency For Science, Technology and Research.

BACKGROUND

The incorporated parent disclosure (Part I) is generally related to cyclic carbonate monomers having a tertiary amine nitrogen in the cyclic carbonate ring, and cationic polymers formed therefrom bearing quaternary amine groups. The continuation-in-part disclosure (Part II) is generally related to monomers having an acylated secondary nitrogen or additional oxygen heteroatom in the cyclic carbonate ring, and polycarbonates prepared therefrom.

Part I. Background

The present invention relates to 1,3,6-dioxazocan-2-ones and antimicrobial polycarbonates formed therefrom by organocatalyzed ring opening polymerization, and more specifically to antimicrobial cationic polycarbonates comprising a quaternary nitrogen in the polycarbonate backbone.

Current ring opening polymerizations of cyclic carbonates are limited by the lack of main chain functionality in the polycarbonate other than the carbonate functionality. The incorporation of heteroatoms (e.g., nitrogen) in the polymer backbone is hampered by monomer instability. Heteroatom incorporation other than the carbonate oxygens within a 7-membered ring or smaller ring monomer produces an unstable species (e.g., acetals, hemiaminals, and thioacetals for 6-membered and 7-membered rings, and peroxides and N-oxides for 5-membered rings).

Cyclic carbonate monomers comprising a ring heteroatom in addition to the carbonate oxygens are needed, in particular those comprising a ring nitrogen. Also needed are methods of ring opening polymerizations that produce polymers bearing a heteroatom other than carbonate oxygens.

Part II. Background

There is no additional background.

SUMMARY

Part I. Summary

Accordingly, a compound is disclosed of formula (1):

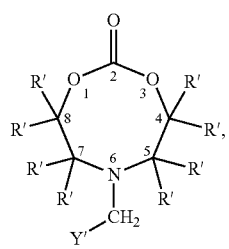

(1)

wherein
ring positions are numbered 1 to 8,
each R' is an independent monovalent radical selected from the group consisting of hydrogen and groups comprising 1 to 10 carbons, and
Y' is a monovalent radical selected from the group consisting of hydrogen and groups comprising 1 or more carbons.

Also disclosed is a method, comprising:
forming a mixture comprising, an organocatalyst, a solvent, a nucleophilic initiator comprising one or more nucleophilic groups capable of initiating a ring opening polymerization, an optional accelerator, and a compound of formula (1):

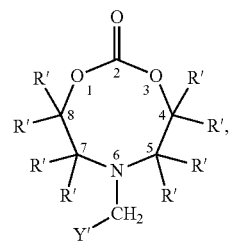

(1)

wherein
ring positions are numbered 1 to 8,
each R' is an independent monovalent radical selected from the group consisting of hydrogen and groups comprising 1 to 10 carbons, and
Y' is a monovalent radical selected from the group consisting of hydrogen and groups comprising 1 or more carbons;
agitating the mixture, thereby forming an initial polymer by ring opening polymerization of the compound, the initial polymer comprising a basic repeat unit comprising a backbone carbonate group and a backbone tertiary nitrogen, the backbone nitrogen capable of reacting with a quaternizing agent to form a positive-charged backbone quaternary nitrogen; and
treating the initial polymer with the quaternizing agent, thereby forming a cationic polymer comprising a cationic repeat unit comprising the backbone carbonate group and the positive-charged backbone quaternary nitrogen, the quaternary nitrogen linked to 4 carbons.

Also disclosed is a cationic polymer having a structure according to formula (6):

$$I''-[Q'-E'']_{n'} \qquad (6),$$

wherein
n' is a positive integer greater than or equal to 1,
each Q' is an independent divalent polymer chain comprising a cationic repeat unit, wherein the cationic repeat unit comprises i) a backbone portion comprising a backbone carbonate group, ii) a positive-charged backbone quaternary nitrogen linked to 4 carbons, iii) a first side chain portion having a structure *—$CH_2$—Y', wherein the starred bond is linked to the backbone quaternary nitrogen, and Y' is selected from the group consisting of hydrogen and groups comprising 1 or more carbons, and iv) a second side chain portion comprising 1 or more carbons, wherein one carbon of the second side chain portion is linked to the quaternary nitrogen,
I'' has a valency of n', I'' comprises 1 or more carbons, and I'' comprises n' heteroatoms independently selected from the group consisting of oxygen, nitrogen, and sulfur, wherein each of the heteroatoms is linked to a respective Q' terminal backbone carbonyl group, each E" is a monovalent second end group selected from the group consisting of hydrogen and moieties comprising 1 to 50 carbons, wherein each E" is linked to a respective Q' terminal backbone oxygen, and the cationic polymer is an effective antimicrobial agent.

Further disclosed is a method of killing a microbe, comprising contacting the microbe with an above-described cationic polymer.

Also disclosed is a medical composition for treating wounds and/or infections, comprising one or more of the above-described cationic polymers.

Also disclosed is a cationic polymer of formula (8):

(8), wherein each Q' is an independent divalent polymer chain comprising a cationic repeat unit, wherein the cationic repeat unit comprises i) a backbone portion comprising a backbone carbonate group, ii) a positive-charged backbone quaternary nitrogen linked to 4 carbons, iii) a first side chain portion having a structure *—CH$_2$—Y', wherein the starred bond is linked to the backbone quaternary nitrogen, and Y' is selected from the group consisting of hydrogen and groups comprising 1 or more carbons, and iv) a second side chain portion comprising 1 or more carbons, wherein one carbon of the second side chain portion is linked to the quaternary nitrogen, I" is a divalent radical comprising 1 or more carbons, and I" comprises 2 heteroatoms independently selected from the group consisting of oxygen, nitrogen, and sulfur, wherein each of the heteroatoms is linked to a respective Q' terminal backbone carbonyl group, each E" is an independent monovalent second end group selected from the group consisting of hydrogen and moieties comprising 1 to 50 carbons, wherein each E" is linked to a respective Q' terminal backbone oxygen.

Part II. Summary

A compound is disclosed of formula (N-1):

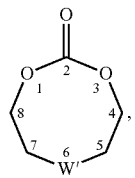
(N-1)

wherein

W' is a divalent radical selected from the group consisting of *—O—* and

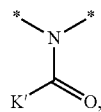

wherein K' is a monovalent radical selected from the group consisting of hydrogen, *—R$^1$, *—OR$^1$, and *—NHR$^1$, wherein R$^1$ is a C$_1$-C$_{10}$ monovalent hydrocarbyl group.

Also disclosed is a method of forming the compound of claim 1, comprising:

forming a mixture comprising ethyl chloroformate, a solvent, an amine base, and a compound of formula (N-2):

(N-2)

wherein

W' is a divalent radical selected from the group consisting of *—O—* and

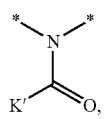

wherein K' is a monovalent radical selected from the group consisting of hydrogen, *—R$^1$, *—OR$^1$, and *—NHR, wherein R$^1$ is a C$_1$-C$_{10}$ monovalent hydrocarbyl group; and agitating the mixture, thereby forming the compound.

Also disclosed is a polycarbonate, comprising:

a repeat unit having a structure according to formula (N-3):

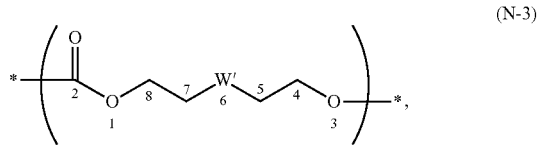
(N-3)

wherein

W' is a divalent radical selected from the group consisting of *—O—* and

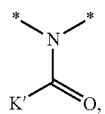

lp;1pwherein K' is a monovalent radical selected from the group consisting of hydrogen, *—R$^1$, *—OR1, and *—NHR1, wherein R1 is a C$_1$-C$_{10}$ monovalent hydrocarbyl group.

Also disclosed is a method of forming the above-described polycarbonate, comprising:

forming a mixture comprising an organocatalyst, a solvent, a nucleophilic initiator comprising one or more nucleophilic groups capable of initiating a ring opening polymerization, an optional accelerator, and a monomer of formula (N-1):

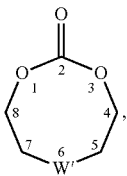
(N-1)

wherein

W' is a divalent radical selected from the group consisting of *—O—* and

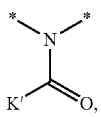

wherein K' is a monovalent radical selected from the group consisting of hydrogen, *—R$^1$, *—OR$^1$, and *—NHR$^1$, wherein R$^1$ is a C$_1$-C$_{10}$ monovalent hydrocarbyl group; and agitating the mixture, thereby forming the polycarbonate by ring opening polymerization of the monomer.

Also disclosed is a cationic polymer, comprising a cationic carbonate repeat unit of formula (N-11):

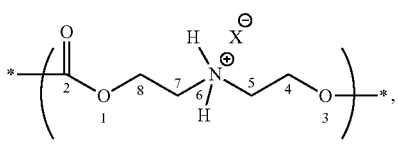
(N-11)

wherein X$^\ominus$ is a negative-charged counterion.

Also disclosed is a compound of formula (N-12):

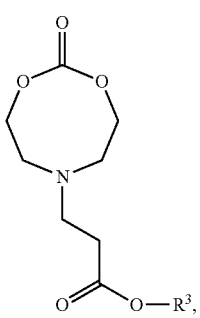
(N-12)

wherein R$^3$ is a hydrocarbyl group comprising 1 to 10 carbons.

Also disclosed is a polymer, comprising: a carbonate repeat unit of formula (N-13):

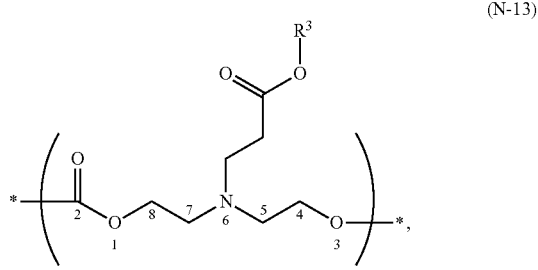
(N-13)

wherein R$^3$ is a hydrocarbyl group comprising 1 to 10 carbons.

The above-described and other features and advantages of the present invention will be appreciated and understood by those skilled in the art from the following detailed description, drawings, and appended claims.

BRIEF DESCRIPTION OF THE SEVERAL VIEWS OF THE DRAWINGS

Part I. Brief Description of Drawings

Part II. Brief Description of Drawings

Figure 1:
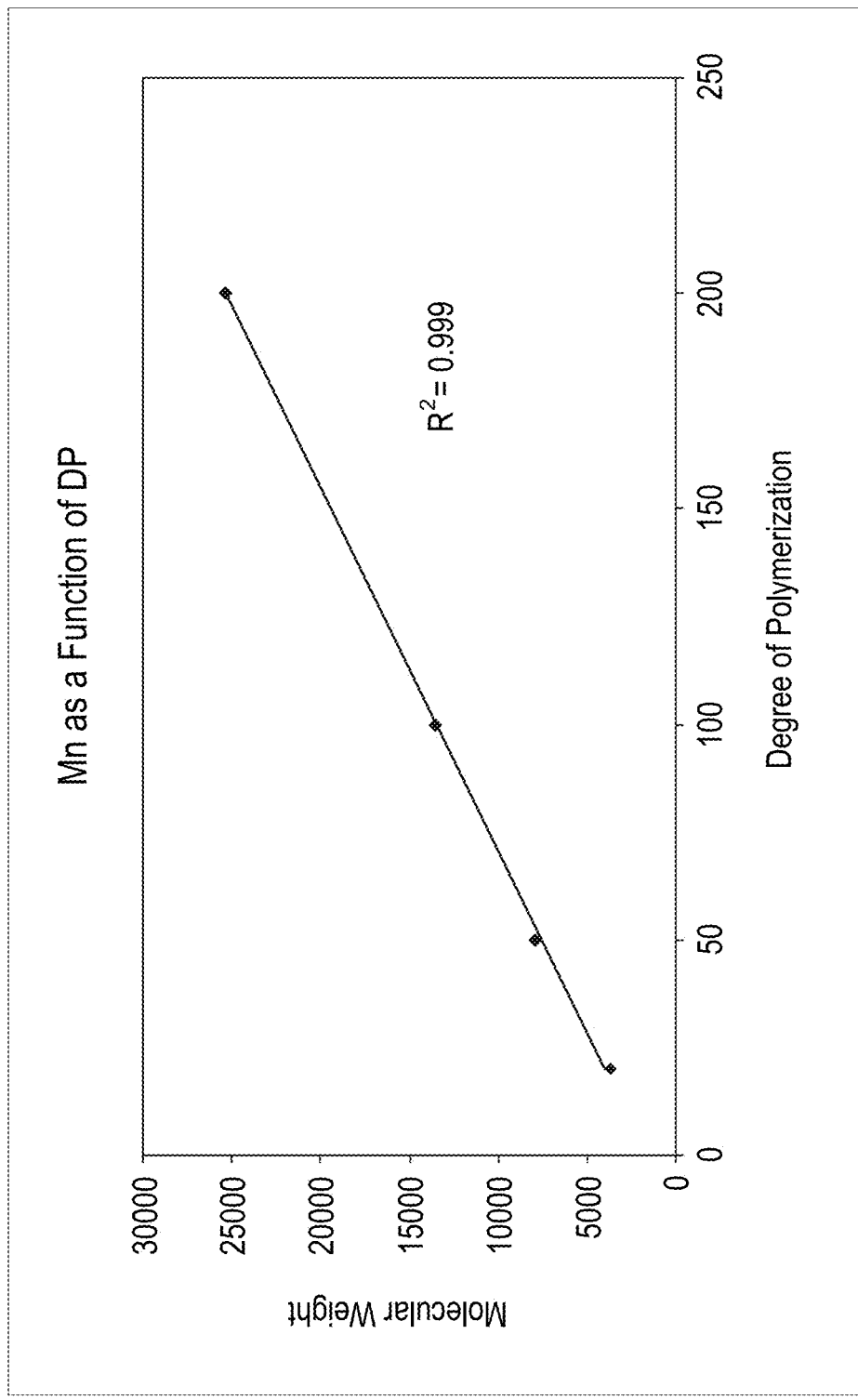
FIG. 1 is a graph of number average molecular weight versus average degree of polymerization of polymers P-1 to P-4 (before quaternization).

There are no additional figures for this section.

DETAILED DESCRIPTION

The following detailed description has two parts. Part I contains the parent detailed description and examples. Part II, contains the continuation-in-part detailed description and examples, and can be found following the examples section of Part I.

Part I. Detailed Description

Disclosed are 1,3,6-dioxazocan-2-ones, hereinafter referred to as "first cyclic monomers," that undergo organo-catalyzed ring opening polymerization (ROP), thereby forming an initial polymer comprising a tertiary nitrogen in the polymer backbone. Treating the initial polymer with a suitable quaternizing agent produces a cationic polymer comprising a positive charged quaternary nitrogen in the cationic polymer backbone. The cationic polymers can be potent antimicrobial agents against Gram-negative microbes, Gram-positive microbes, yeast, fungi, and combinations thereof.

The initial polymer comprises a basic repeat unit. The basic repeat unit comprises a backbone portion (i.e., a portion of the initial polymer backbone) and a side chain portion. The backbone portion of the basic repeat unit comprises a carbonate group and a tertiary nitrogen linked to three carbons. The side chain portion has a structure *—CH$_2$—Y', wherein the starred bond is linked to the tertiary nitrogen and Y' is selected from the group consisting of hydrogen and groups comprising 1 or more carbons.

The initial polymer can be a homopolymer, random copolymer, or block copolymer comprising the basic repeat unit. The initial polymer can include one or more polymer chain segments comprising the basic repeat unit. At least one of the polymer chain segments comprises the basic repeat unit. For example, each block of a block copolymer is a polymer chain segment that can be a homopolymer or copolymer. At least one block of the block copolymer comprises the basic repeat unit. The initial polymer can comprise the one or more polymer chain segments in a linear or branched arrangement of repeat units. Branched structures can include star polymers, graft polymers, brush polymers, mikto-arm polymers and dendritic polymers.

The cationic polymer comprises a cationic repeat unit. The cationic repeat unit comprises a backbone portion (i.e., a portion of the cationic polymer backbone), a first side chain portion and a second side chain portion. The backbone portion of the cationic repeat unit comprises a backbone carbonate group and a backbone positive-charged quaternary nitrogen, which is covalently bonded to four carbons. The quaternary nitrogen of the backbone is not covalently bonded to any hydrogen. The positive-charged quaternary nitrogen is linked to a carbon of the first side chain portion and to a carbon of the second side chain portion. The first side chain portion has a structure *—CH$_2$—Y', wherein the starred bond is linked to the quaternary nitrogen. The second side chain portion is a moiety comprising at least one carbon.

The cationic polymer can be a homopolymer, random copolymer, or block copolymer comprising the basic repeat unit. The cationic polymer can include one or more polymer chain segments, wherein at least one of the polymer chain segments comprises the cationic repeat unit. For example, each block of the block copolymer can be a homopolymer or a copolymer, wherein at least one block comprises the cationic repeat unit. The cationic polymer can comprise the one or more polymer chain segments in a linear or branched arrangement of repeat units. Branched structures can include star polymers, graft polymers, brush polymers, dendritic polymers, mikto-arm polymers and the like.

More specifically, the first cyclic monomers have a structure according to formula (1):

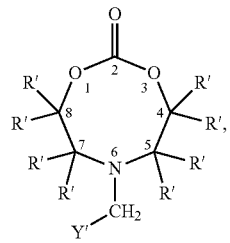

(1)

wherein
ring positions are numbered 1 to 8,
each R' is an independent monovalent radical selected from the group consisting of hydrogen and groups comprising 1 to 10 carbons, and
Y' is a monovalent radical selected from the group consisting of hydrogen and groups comprising 1 or more carbons.

The tertiary nitrogen at ring position 6 is bonded to three carbons as shown in formula (1). In an embodiment, each R' is hydrogen.

Non-limiting examples of Y' include hydrogen, methyl, ethyl, propyl, phenyl, and substituted phenyl. Y' can include additional functionality such as, for example, ester, amide, carbamate, thioester, ketone, ether, amine, nitrogen-containing heterocycle, oxygen-containing heterocycle, olefin, acetylene, nitrile, bicyclic rings, and combinations thereof.

Non-limiting examples of *—CH$_2$Y' groups include methyl, ethyl, propyl, butyl, benzyl, and substituted benzyl.

The first cyclic monomers can be prepared from amine-diols of formula (2):

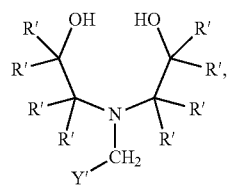

(2)

wherein
each R' is an independent monovalent radical selected from the group consisting of hydrogen and groups comprising 1 to 10 carbons, and
Y' is a monovalent radical selected from the group consisting of hydrogen and groups comprising 1 or more carbons.

The first cyclic monomers can be prepared by treating an amine-diol of formula (2) with a carbonate forming compound. Although a base catalyst is not essential; the reaction is preferably conducted using a base (e.g., triethylamine).

Non-limiting carbonate forming compounds include phosgene, triphosgene, ethylchloroformate, diphenylcarbonate, bis-(pentafluorophenyl)carbonate, bis-(pentachlorophenyl)carbonate, and the like.

The first cyclic monomers undergo organocatalyzed ring opening polymerization (ROP) to form the initial polymer. The ROP can include other cyclic carbonyl monomers, including cyclic carbonates and/or cyclic esters that can serve as diluents (comonomers) for the first cyclic monomers. As non-limiting examples, a polymer chain segment of the initial polymer can be a polycarbonate copolymer comprising two or more different carbonate repeat units, or a polyestercarbonate copolymer, comprising at least one carbonate repeat unit and one ester repeat unit.

The first cyclic monomer can be stereospecific or non-stereospecific.

Initial Polymers

The initial polymer can have a structure according to formula (3):

$$I'\text{-}[\text{-}P'\text{-}E']_{n'} \quad (3),$$

wherein n' is an positive integer greater than or equal to 1, each P' is a divalent polymer chain comprising one or more polymer chain segments, a terminal backbone carbonyl group, and a terminal backbone oxygen, wherein at least one of the polymer chain segments comprises a basic carbonate repeat unit, I' is a radical having a valency of 1 or more, wherein I' comprises 1 or more carbons, the backbone carbonyl group of each P' is linked to a respective independent heteroatom of I' selected from the group consisting of oxygen, nitrogen, and sulfur;

the basic carbonate repeat unit comprises a backbone portion and a first side chain portion, the backbone portion comprising a backbone carbonate group and a backbone tertiary nitrogen, the first side chain portion having a structure *—$CH_2$—Y', wherein the starred bond is linked to the backbone tertiary nitrogen and Y' is selected from the group consisting of hydrogen and groups comprising 1 or more carbons, E' is a monovalent second end group selected from the group consisting of hydrogen and moieties comprising 1 to 50 carbons, and the terminal backbone oxygen of each P' is linked to a respective E'.

I' can be a residue of a nucleophilic initiator for an organocatalyzed ROP of the first cyclic monomers, wherein the nucleophilic initiator comprises n nucleophilic sites capable of initiating the ROP, and n' polymer chains P' are formed by the ROP.

Each P' can be a homopolymer, random copolymer, or block copolymer comprising the basic repeat unit. Each P' can have an average degree of polymerization (DP) of more than 1 to about 200. In an embodiment, n'=1 and the initial polymer comprises one polymer chain P' having an average DP of about 20 to about 100.

The initial polymer can comprise basic repeat units singularly or in combination. P' can further comprise repeat units derived from cyclic carbonate and/or cyclic ester monomers other than the first cyclic monomers.

Each P' preferably has a linear arrangement of repeat units (i.e., each P' is a linear polymer chain comprising one polymer branch as opposed to intersecting polymer branches). When P' contains two or more polymer chain segments (e.g., as a diblock copolymer chain), the different chain segments are linked by their respective chain ends, no more than two polymer chain ends are linked together by a given linking group, and the respective polymer chain segments are not linked together in the form of a cyclic polymer structure.

I' can be a residue of a nucleophilic initiator for the organocatalyzed ring opening polymerization used to form P', or a derivative of the residue. Preferably, I' comprises n' number of independent heteroatoms selected from the group consisting of an oxygen, nitrogen, and sulfur, wherein each of the heteroatoms is linked in the form of a carbonate, carbamate or thiocarbonate group to a respective P' terminal backbone carbonyl group' (i.e., to the "carbonyl end" of P').

I' can comprise a biologically active moiety such as, for example a steroid group and/or a vitamin. I' can comprise a polymer such as, for example a poly(ethylene oxide) chain segment. In an embodiment, I' is a residue of a mono-endcapped mono-nucleophilic polyethylene oxide initiator (e.g., mono-methylated polyethylene glycol (mPEG)). In another embodiment, I' comprises 1 to 50 carbons. In yet another embodiment, I' is an alkoxy or aryloxy group comprising 1 to 10 carbons.

Each E' is preferably linked to a terminal backbone oxygen at the opposing end of a respective polymer chain P', referred to herein as the "oxy end" of P'. When E' is hydrogen, P' has a terminal hydroxy group (i.e., a living chain end capable of initiating another ring opening polymerization). When E' is not hydrogen, E' can be any suitable end group comprising 1 to 50 carbons. In an embodiment, E' is an acyl group comprising 1 to 15 carbons (e.g., acetyl group).

The basic repeat unit of the initial polymer has a structure according to formula (4):

$$\text{(4)}$$

[Chemical structure of formula (4) with backbone atoms numbered 1 to 8, showing: *—C(=O)—O—C(R')(R')—C(R')(R')—N(—CH_2—Y')—C(R')(R')—C(R')(R')—O—*]

wherein backbone atoms of the basic repeat unit are numbered 1 to 8, the starred bonds represent attachment points to other repeat units and/or end groups of the initial polymer, each R' is an independent monovalent radical selected from the group consisting of hydrogen and groups comprising 1 to 10 carbons,

*—$CH_2$—Y' is a first side chain, wherein Y' is a monovalent radical selected from the group consisting of hydrogen, and groups comprising 1 or more carbons.

The tertiary nitrogen of formula (4) is bonded to two backbone carbons labeled 5 and 7 and to the methylene carbon of the first side chain *—$CH_2$—Y'. In an embodiment, each R' is hydrogen.

In an embodiment, n'=1. A non-limiting example of an initial polymer of formula (3) wherein n'=1 is the polycarbonate A-1:

(A-1)

[Chemical structure showing I' (benzyl group), Carbonyl End, backbone atoms numbered 1,2,8,7,6,5,4,3, Oxy End, and E' (H), with P' bracket encompassing the polymer chain, subscript a']

In this example, the initial polymer A-1 has one polymer chain P' which has one polymer chain segment. In this example, P' is a polycarbonate homopolymer of the basic repeat unit shown in parentheses. A-1 has a linear polymer arrangement of the basic repeat units, which are linked in a head-to-tail arrangement, wherein carbon 2 represents the head, and oxygen 3 represents the tail. Polymer chain P' of A-1 has two polymer chain ends linked to respective end groups I' and E'. The carbonyl end and oxy end of P' are indicated by arrows. The basic repeat unit of A-1 has a structure according to formula (4) wherein each R' is H and Y' is phenyl. The first end group I' is benzyloxy, and the second end group E' is hydrogen. Subscript a' represents the degree of polymerization, and has an average value of 2 to 200. A-1 has a living end containing a primary alcohol, which can potentially initiate a ring opening polymerization.

Another more specific initial polymer comprises two polymer chains P' (n'=2 in formula (4)). In this instance, the initial polymer can have a structure in accordance with formula (5):

$$E^a\text{---}P^a\text{---}I^a\text{---}P^b\text{---}E^b \qquad (5),$$

wherein $P^a$ is a first divalent polymer chain comprising one or more polymer chain segments, wherein at least one of the polymer chain segments comprises a basic repeat unit, $P^b$ is a second divalent polymer chain comprising one or more polymer chain segments, wherein at least one of the polymer chain segments comprises a basic carbonate repeat unit, the basic carbonate repeat unit comprises a backbone portion and a first side chain portion, the backbone portion comprising a backbone carbonate group and a backbone tertiary nitrogen, the first side chain portion having a structure *—$CH_2$—Y', wherein the starred bond is linked to the backbone tertiary nitrogen and Y' is selected from the group consisting of hydrogen and groups comprising 1 or more carbons, $I^a$ is a divalent linking group covalently bound to the respective carbonyl ends of $P^a$ and $P^b$, $E^a$ is a monovalent first end group selected from the group consisting of hydrogen and moieties comprising 1 to 50 carbons, wherein $E^a$ is linked to the oxy end of $P^a$, and $E^b$ is a monovalent second end group selected from the group consisting of hydrogen and moieties comprising 1 to 50 carbons, wherein $E^b$ is linked to the oxy end of $P^b$.

$P^a$ can have an average degree of polymerization of more than 1 to about 200. $P^a$ can be a homopolymer, random copolymer, or block copolymer comprising the basic repeat unit.

$P^b$ can have an average degree of polymerization of more than 1 to about 200. $P^b$ can be a homopolymer, random copolymer, or block copolymer comprising the basic repeat unit.

In an embodiment, $I^a$ is a residue of a di-nucleophilic initiator for the organocatalyzed ring opening polymerization used to prepare $E^a$-$P^a$—$I^a$—$P^b$-$E^b$. In this instance, $I^a$ comprises two heteroatoms independently selected from oxygen, nitrogen, and sulfur, wherein the two heteroatoms are independently linked in the form of carbonate, carbamate, or thiocarbonate groups to respective carbonyl ends of $P^a$ and $P^b$. $I^a$ can be a derivative of the residue of the di-nucleophilic initiator for the ROP.

$I^a$ can comprise a polymer such as, for example, a divalent poly(ethylene oxide) chain. $I^a$ can comprise a biologically active group such as a steroid and/or a vitamin. In an embodiment, $I^a$ is a residue of a di-nucleophilic polyethylene glycol initiator for the ROP. In another embodiment, $I^a$ comprises 1 to 50 carbons. In another embodiment, $I^a$ is a residue of an ester of 2,2-dimethylol propionic acid.

$E^a$ is linked to the oxy end of $P^a$. When $E^a$ is hydrogen, $P^a$ has a terminal hydroxy group (i.e., a living chain end potentially capable of initiating another ring opening polymerization). When $E^a$ is not hydrogen, $E^a$ can be any suitable end group comprising 1 to 50 carbons. In an embodiment, $E^a$ is an acyl group comprising 1 to 10 carbons.

$E^b$ is linked to the oxy end of $P^b$. When $E^b$ is hydrogen, $P^b$ has a terminal hydroxy group (i.e., a living chain end potentially capable of initiating another ring opening polymerization). When $E^b$ is not hydrogen, $E^b$ can be any suitable end group comprising 1 to 50 carbons. In an embodiment, $E^b$ is an acyl group comprising 1 to 10 carbons.

A non-limiting example of an initial polymer of formula (5) is A-2:

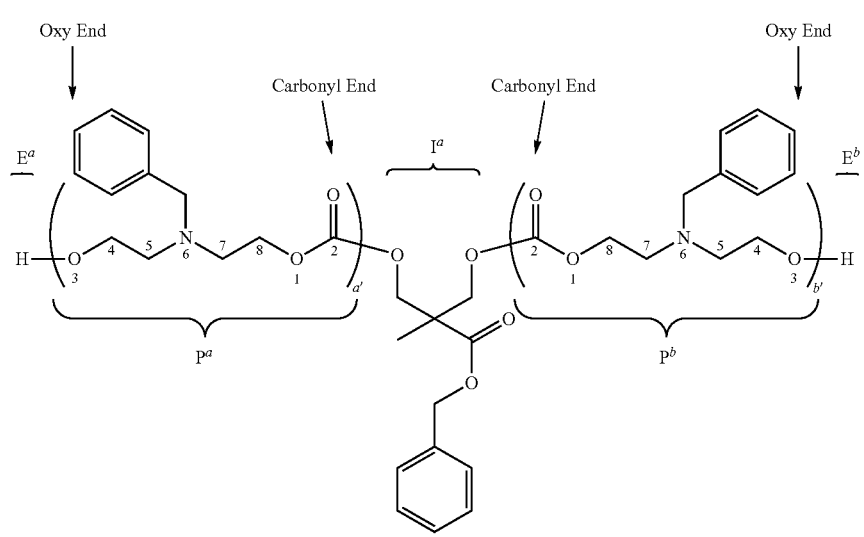

The initial polymer A-2 is a linear polymer containing two polymer chains linked by respective chain ends to divalent linking group I$^a$. Each polymer chain P$^a$ and P$^b$ of A-2 is a polycarbonate homopolymer of the basic repeat unit in parentheses. The carbonyl ends and oxy ends of each polymer chain P$^a$ and P$^b$ are labeled in A-2. The basic repeat unit of each polymer chain has a structure according to formula (4), wherein each R' is H and Y' is phenyl. I$^a$ is benzyl 2,2-bis(oxymethylene)propionate, E$^a$ is hydrogen, and E$^b$ is hydrogen. Subscripts a' and b' represent degree of polymerization and independently have average values of more than 1 to about 200. The initial polymer A-2 has two living ends containing primary alcohols, each potentially capable of initiating a ring opening polymerization.

The initial polymers can be stereospecific or non-stereospecific.

Cationic Polymers

When treated with a suitable amine quaternizing agent, the initial polymers form cationic polymers comprising cationic repeat units. The cationic repeat units comprise a positive-charged backbone quaternary nitrogen linked to 4 carbons.

Quaternization of initial polymers of structure I'—[P'-E']$_{n'}$ produces cationic polymers having a structure in accordance with formula (6):

I"—[Q'—E"]$_{n'}$ (6), wherein n' is a positive integer greater than or equal to 1, each Q' is an independent divalent polymer chain comprising a cationic repeat unit, wherein the cationic repeat unit comprises i) a backbone portion comprising a backbone carbonate group, ii) a positive-charged backbone quaternary nitrogen linked to 4 carbons, iii) a first side chain portion having a structure *—CH$_2$—Y', wherein the starred bond is linked to the backbone quaternary nitrogen, and Y' is selected from the group consisting of hydrogen and groups comprising 1 or more carbons, and iv) a second side chain portion comprising 1 or more carbons, wherein one carbon of the second side chain portion is linked to the quaternary nitrogen, I" has a valency of n', I" comprises 1 or more carbons, and I" comprises n' heteroatoms independently selected from the group consisting of oxygen, nitrogen, and sulfur, wherein the heteroatoms are linked to respective Q' terminal backbone carbonyl groups, each E" is a monovalent second end group selected from the group consisting of hydrogen and moieties comprising 1 to 50 carbons, wherein each E" is linked to a respective Q' terminal backbone oxygen.

Each Q' can have an average degree of polymerization of more than one to about 200. Each Q' can be a homopolymer, random copolymer, or block copolymer comprising the cationic repeat unit.

The cationic polymer can comprise the cationic repeat units singularly or in combination. Each Q' can further comprise additional repeat units derived from cyclic carbonate and/or cyclic ester comonomers, which can act as diluents for the cationic repeat unit.

Each Q' preferably has a linear arrangement of repeat units (i.e., each Q' is a linear polymer chain comprising one polymer branch as opposed to intersecting polymer branches). When Q' contains two or more polymer chain segments (e.g., as a diblock copolymer chain), the different chain segments are linked by their respective chain ends, no more than two polymer chain ends are linked together by a given linking group, and the respective polymer chain segments are not linked together in the form of a cyclic polymer structure.

I" can be a residue of a nucleophilic initiator for the ring opening polymerization used to form the basic initial polymer, I'—[P'—E']$_{n'}$, which serves as a precursor to the cationic polymer. I" can be a derivative of the residue of a nucleophilic initiator. Each of the above-described heteroatoms of I" is linked in the form of carbonate, carbamate or thiocarbonate group to a respective Q' terminal backbone carbonyl group' (i.e., the carbonyl end of a Q').

I" can comprise a biologically active moiety such as, for example, a steroid group and/or a vitamin. I" can comprise a polymer such as, for example a poly(ethylene oxide) chain segment. In an embodiment, I" is a residue of a mono-endcapped mono-nucleophilic polyethylene oxide initiator (e.g., mono-methylated polyethylene glycol (mPEG)). In another embodiment, I" comprises 1 to 50 carbons. In another embodiment, I" is an alkoxy or aryloxy group comprising 1 to 10 carbons. In another embodiment, I" is the same as I'.

Each E" is linked to a terminal backbone oxygen at the opposing end of a respective polymer chain Q' (i.e., to the oxy end of Q'). When E" is hydrogen, Q' has a terminal hydroxy group (i.e., a living chain end capable of initiating another ring opening polymerization). When E" is not hydrogen, E" can be any suitable end group comprising 1 to 50 carbons. In an embodiment, E" is an acyl group comprising 1 to 15 carbons. In another embodiment, E" is the same as E'.

The cationic repeat unit of the cationic polymer has a structure according to formula (7):

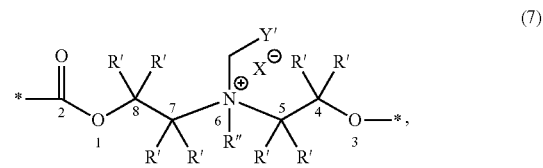

wherein cationic polymer backbone atoms are numbered 1 to 8, the starred bonds represent attachment points to other repeat units and/or end groups of the cationic polymer, each R' is an independent monovalent radical selected from the group consisting of hydrogen and groups comprising 1 to 10 carbons, R" is a group comprising 1 or more carbons, wherein one carbon of R" is bonded to the positive charged nitrogen labeled 6, Y' is a monovalent radical selected from the group consisting of hydrogen, and groups comprising 1 or more carbons, and X$^\ominus$ is a negative-charged counterion.

The quaternary nitrogen of formula (7) is bonded to 4 carbons: carbons labeled 5 and 7, the methylene carbon of side chain *—CH$_2$—Y', and one carbon of R". In an embodiment, each R' is hydrogen.

X$^\ominus$ can be any suitable negative-charged counterion. In an embodiment, X$^\ominus$ is selected from the group consisting of chloride, bromide, and iodide. X$^\ominus$ counterions can be presented singularly or in combination.

In an embodiment, n'=1. A non-limiting example of a cationic polymer of formula (6) wherein n'=1 is the polycarbonate A-3:

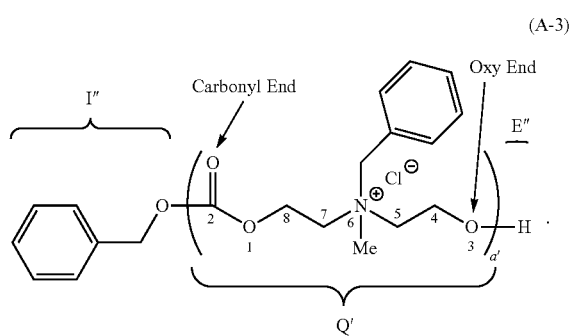

(A-3)

A-3 has one polymer chain Q' comprising one polymer chain segment. In this example, Q' is a polycarbonate homopolymer of the cationic repeat unit shown in parentheses. A-3 has a linear polymer structure. Polymer chain Q' of A-1 has two polymer chain ends linked to respective end groups I" and E". The carbonyl end and oxy end of Q' are indicated by arrows. The cationic repeat unit of A-3 has a structure according to formula (7), wherein each R' is H, R" is methyl, $X^{\ominus}$ is chloride ion, and Y' is phenyl. The first end group I" is benzyloxy, and the second end group E" is hydrogen. Subscript a' represents the degree of polymerization and has an average value of 2 to 200. A-3 has a living end containing a primary alcohol, which can potentially initiate a ring opening polymerization.

linked to the backbone quaternary nitrogen, and Y' is selected from the group consisting of hydrogen and groups comprising 1 or more carbons, and iv) a second side chain portion comprising 1 or more carbons, wherein one carbon of the second side chain portion is linked to the quaternary nitrogen, I" is a divalent radical comprising 1 or more carbons, and I" comprises 2 heteroatoms independently selected from the group consisting of oxygen, nitrogen, and sulfur, wherein each of the heteroatoms is linked to a respective Q' terminal backbone carbonyl group, each E" is an independent monovalent second end group selected from the group consisting of hydrogen and moieties comprising 1 to 50 carbons, wherein each E" is linked to a respective Q' terminal backbone oxygen.

Each Q' of formula (8) can have an average degree of polymerization of more than 1 to about 200. Each Q' can be a homopolymer, random copolymer, or block copolymer comprising the cationic repeat unit.

I" can comprise a polymer such as, for example, a divalent poly(ethylene oxide) chain. I" can comprise a biologically active group such as a steroid and/or a vitamin. In an embodiment, I" is a residue of a di-nucleophilic polyethylene glycol (PEG) initiator for the ROP. In another embodiment, I" comprises 1 to 50 carbons. In another embodiment, I" is a residue of an ester of 2,2-dimethylol propionic acid. In another embodiment, I" is the same as $I^a$.

Each E" is linked to the oxy end of a respective Q'.

A non-limiting example of a cationic polymer of formula (8) is A-4:

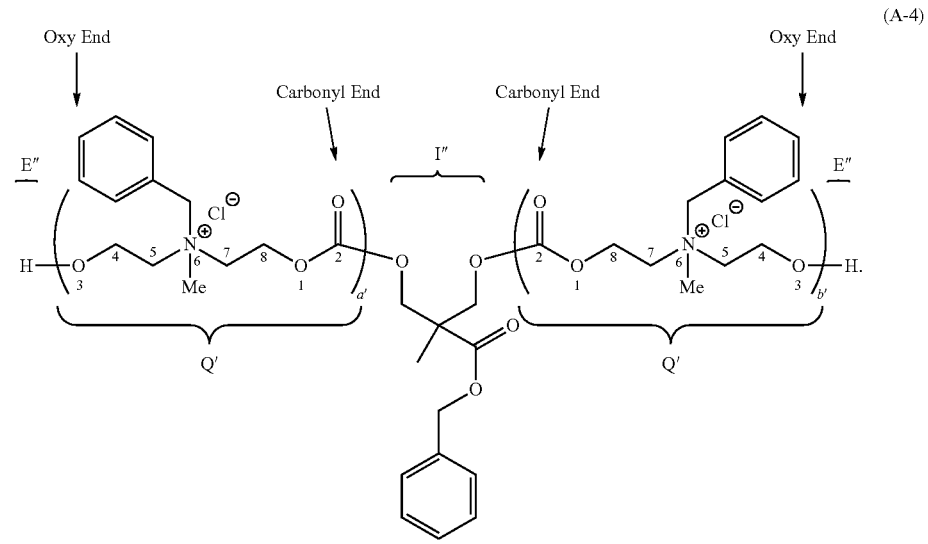

(A-4)

Another more specific cationic polymer comprises two polymer chains Q' (n'=2 in formula (6)). In this instance, the cationic polymer can have a structure in accordance with formula (8):

$$E''—Q'—I''—Q'—E'' \quad (8),$$

wherein each Q' is an independent divalent polymer chain comprising a cationic repeat unit, wherein the cationic repeat unit comprises i) a backbone portion comprising a backbone carbonate group, ii) a positive-charged backbone quaternary nitrogen linked to 4 carbons, iii) a first side chain portion having a structure *—CH$_2$—Y', wherein the starred bond is The cationic polymer A-4 is a linear polymer containing two polymer chains Q' linked by respective carbonyl ends to divalent linking group I". Each polymer chain Q' is a polycarbonate homopolymer of the cationic repeat unit in parentheses. The carbonyl ends and oxy ends of each polymer chain are labeled in A-4. The cationic repeat unit of each Q' has a structure according to formula (7) wherein each R' is H, Y' is phenyl, R" is methyl, and $X^{\ominus}$ is chloride. In this example, I" is benzyl 2,2-bis(oxymethylene)propionate, and each E" is hydrogen. Subscripts a' and b' represent degree of polymerization and have average values of more than 1 to about 200. The cationic polymer A-4 has two living ends containing primary alcohol groups, which are potentially capable of initiating a ring opening polymerization.

The cationic polymers can be stereospecific or non-stereospecific.

Biologically Active Compounds

E', E", I', and/or I" can comprise a covalently bound form of a biologically active compound, referred to herein as a biologically active moiety. Biologically active compounds include steroids and vitamins. In an embodiment, the biologically active compound is selected from the group consisting of cholesterol, alpha-tocopherol (a vitamin E compound), ergocalciferol (vitamin D2), and combinations thereof.

As a non-limiting example, I' of the initial polymer of formula (3) can have a structure S'-L'-* wherein S' is a steroid group (e.g., a cholesteryl group) and L' is a single bond or any suitable divalent linking group comprising 1 to about 10 carbons. In this instance, L' links S' to the carbonyl end of P'. The steroid group can enhance biocompatibility of the cationic polymer.

The steroid group S' can originate from a naturally occurring human steroid, non-human steroid, and/or a synthetic steroid compound. Herein, a steroid group comprises a tetracyclic ring structure:

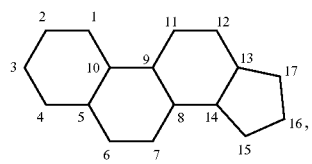

wherein the 17 carbons of the ring system are numbered as shown. The steroid group can comprise one or more additional substituents attached to one or more of the numbered ring positions. Each ring of the tetracyclic ring structure can independently comprise one or more double bonds.

Exemplary steroid groups include cholesteryl, from cholesterol, shown below without stereochemistry:

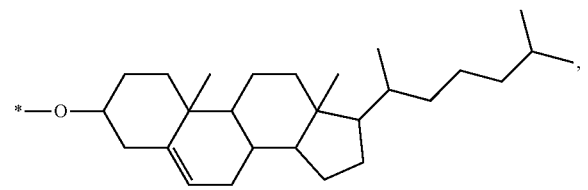 [SMILES: *OC1CCC2(C)C(=CCC3C2CCC2(C)C(C(C)CCCC(C)C)CCC32)C1]

Non-limiting stereospecific structures of cholesteryl include

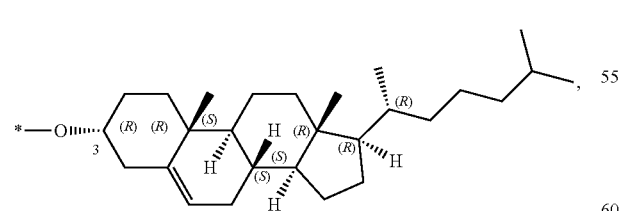

and/or

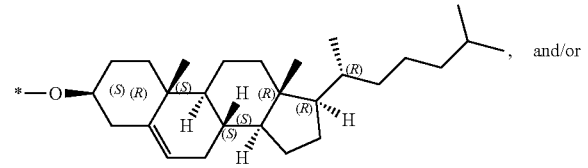

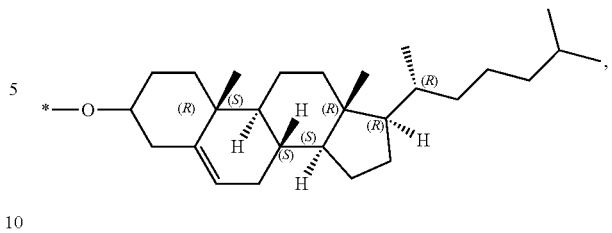

where the R,S stereoconfiguration of each stereospecific asymmetric center is labeled.

Additional non-limiting steroid groups include

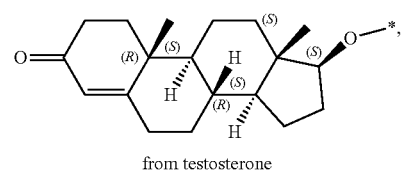

from testosterone

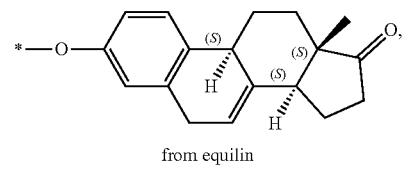

from equilin

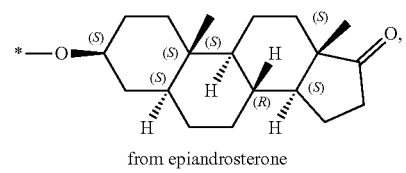

from epiandrosterone

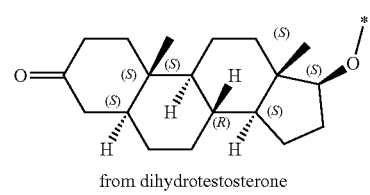

from dihydrotestosterone

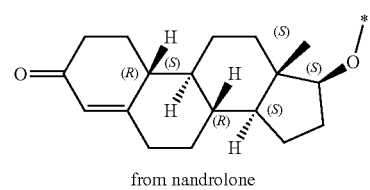

from nandrolone

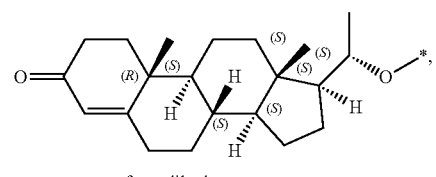

from dihydroprogesterone

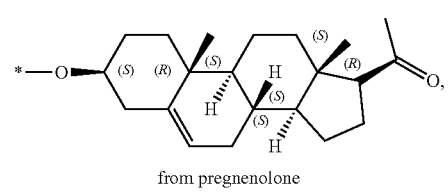

from pregnenolone

-continued

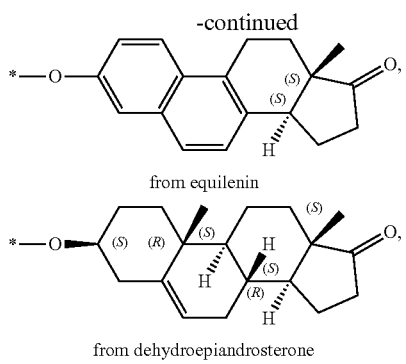

from equilenin from dehydroepiandrosterone

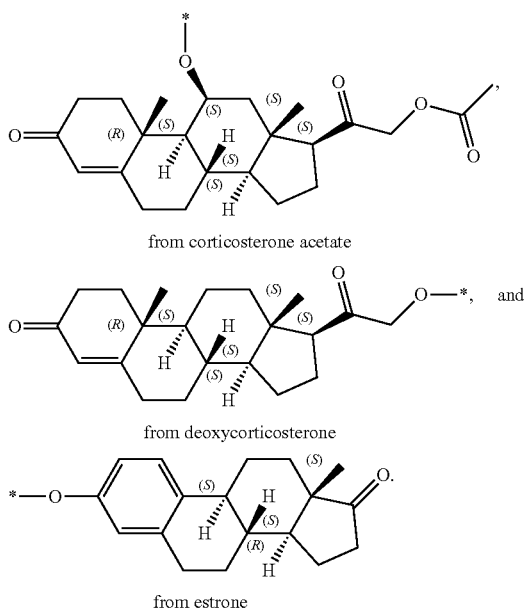

from corticosterone acetate from deoxycorticosterone from estrone

The starred bonds represent attachment points. For example, the starred bond of each of the above steroid groups can be linked to a terminal carbonyl group of the initial polymer backbone and/or the cationic polymer backbone by way of a divalent linking group L'. Alternatively, the starred bond of the steroid group can be directly linked to a terminal carbonyl group of the initial polymer backbone and/or cationic polymer backbone (i.e., L' can be a single bond).

Each asymmetric center of a steroid group can be present as the R stereoisomer, S stereoisomer, or as a mixture of R and S stereoisomers. Additional steroid groups S' include the various stereoisomers of the above structures. The cationic polymer can comprise a steroid group as a single stereoisomer or as a mixture of stereoisomers.

In an embodiment, S' is cholesteryl group, wherein the cholesteryl group is a mixture of isomers

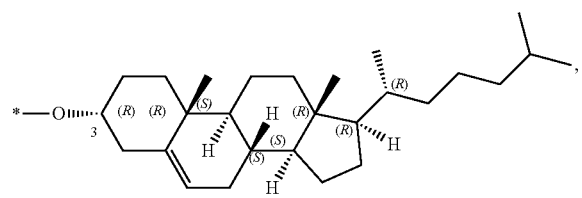

-continued

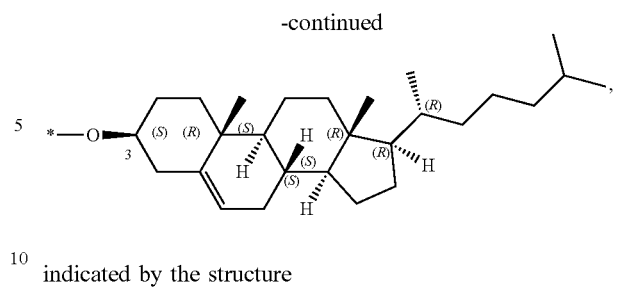

indicated by the structure

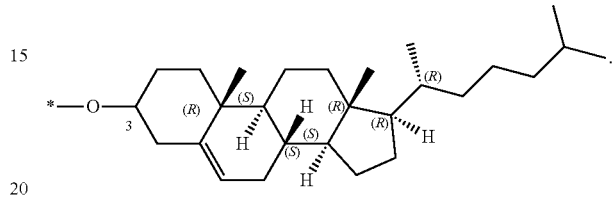

When L' is a single bond, S' is linked directly to the terminal carbonyl group of the polycarbonate backbone. In an embodiment, L' is a divalent linking group comprising an alkylene oxide selected from the group consisting of ethylene oxide (*—CH$_2$CH$_2$O—*), propylene oxide *—CH$_2$CH$_2$CH$_2$O—*, and/or tri(ethylene oxide) (*—CH$_2$CH$_2$OCH$_2$CH$_2$OCH$_2$CH$_2$O—*), wherein the starred bond of the oxygen is linked to the terminal carbonyl group of the initial polymer backbone and/or cationic polymer backbone and the starred bond of the carbon is linked to S'.

Ring Opening Polymerization

A preferred method of preparing the disclosed cationic polymers comprises agitating a first mixture comprising a first cyclic monomer of formula (1), a nucleophilic initiator, an organocatalyst, an optional accelerator, and a solvent, thereby forming an initial polymer by a ring opening polymerization, wherein the initial polymer comprises a basic repeat unit of formula (4). Optionally, the first mixture can include a cyclic carbonyl comonomer selected from cyclic carbonates, cyclic esters, and combinations thereof. Treating the initial polymer with a suitable tertiary amine quaternizing agent forms a cationic polymer comprising a cationic repeat unit of formula (7).

The ring-opening polymerization can be performed at a temperature that is about ambient temperature or higher, more specifically 15° C. to 200° C., and even more specifically 20° C. to 80° C. Preferably, the ROP is performed at ambient temperature. Reaction times vary with solvent, temperature, agitation rate, pressure, and equipment, but in general the polymerizations are complete within 1 to 100 hours.

The ROP polymerization is conducted under an inert dry atmosphere, such as nitrogen or argon, and at a pressure of 100 MPa to 500 MPa (1 atm to 5 atm), more typically at a pressure of 100 MPa to 200 MPa (1 atm to 2 atm). At the completion of the reaction, the solvent can be removed using reduced pressure.

Solvents

The ROP reaction can be performed with or without a solvent. Preferably, the ROP is performed using a solvent. Non-limiting solvents include dichloromethane, chloroform, benzene, toluene, xylene, chlorobenzene, dichlorobenzene, benzotrifluoride, petroleum ether, acetonitrile, pentane, hexane, heptane, 2,2,4-trimethylpentane, cyclohexane, diethyl ether, t-butyl methyl ether, diisopropyl ether, dioxane, tetrahydrofuran, or a combination comprising one of the foregoing solvents. A suitable monomer concentration is about 0.1 to 5 moles per liter, and more particularly about 0.2 to 4 moles per liter.

Comonomers

Non-limiting examples of cyclic carbonate comonomers include the compounds of Table 1. These can be used, for example, to form random copolymers or block copolymers with the first cyclic monomer(s).

TABLE 1

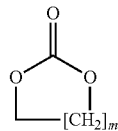

m = 1, Trimethylene carbonate (TMC)
m = 2, Tetramethylene carbonate (TEMC)
m = 3, Pentamethylene carbonate (PMC)

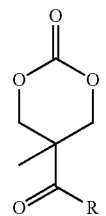

R = hydrogen (MTCOH)
R = methyl (MTCOMe)
R = t-butyl (MTCO$^t$Bu)
R = ethyl (MTCOEt)

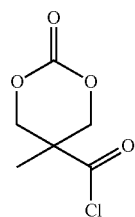

(MTCCl)

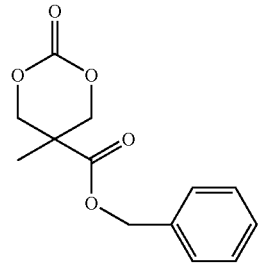

(MTCOBn)

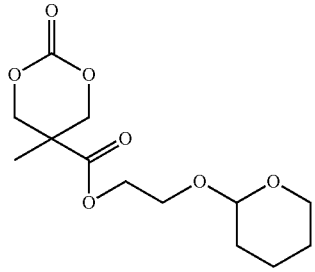 [SMILES: CC1(C(=O)OCCOC2CCCCO2)COC(=O)OC1]

TABLE 1-continued
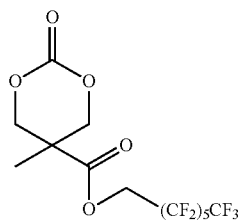
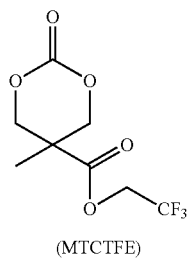 [SMILES: CC1(C(=O)OCC(F)(F)F)COC(=O)OC1]
(MTCTFE)
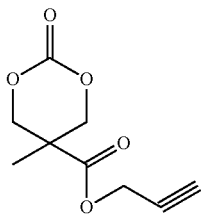
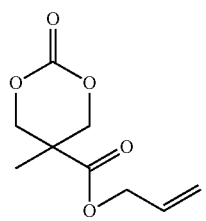
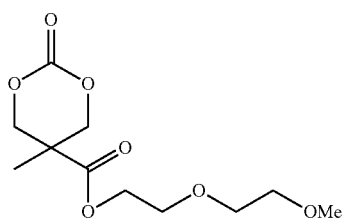 [SMILES: COCCOCCOC(=O)C1(C)COC(=O)OC1]
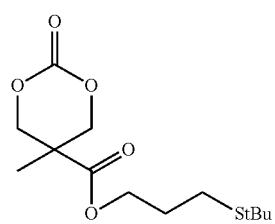
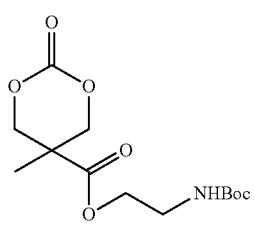 [SMILES: CC(C)(C)OC(=O)NCCOC(=O)C1(C)COC(=O)OC1]

TABLE 1-continued
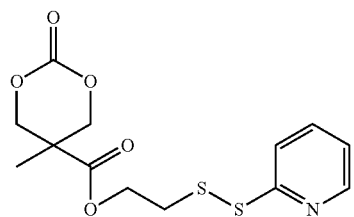 [SMILES: CC1(C(=O)OCCSSc2ccccn2)COC(=O)OC1]
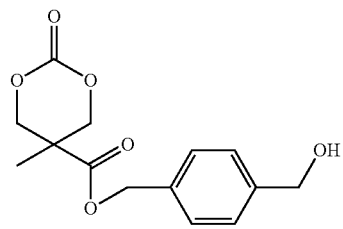 [SMILES: CC1(C(=O)OCc2ccc(CO)cc2)COC(=O)OC1]
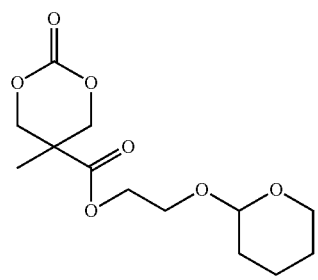 [SMILES: CC1(C(=O)OCCOC2CCCCO2)COC(=O)OC1]
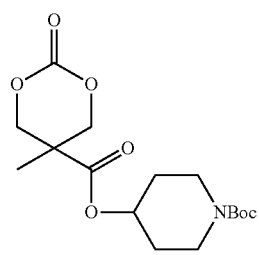 [SMILES: CC(C)(C)OC(=O)N1CCC(OC(=O)C2(C)COC(=O)OC2)CC1]
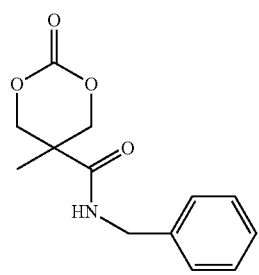 [SMILES: CC1(C(=O)NCc2ccccc2)COC(=O)OC1]
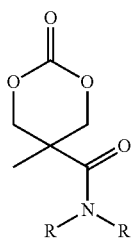
R = methyl
R = iso-propyl TABLE 1-continued
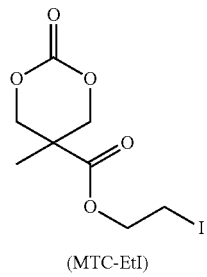
(MTC-EtI)
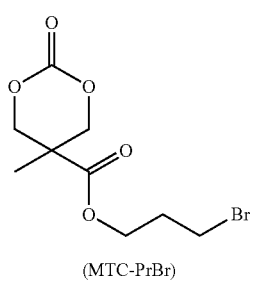
(MTC-PrBr)
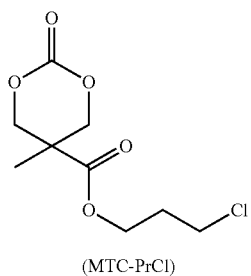
(MTC-PrCl)
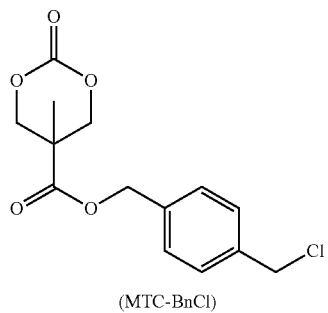
(MTC-BnCl)
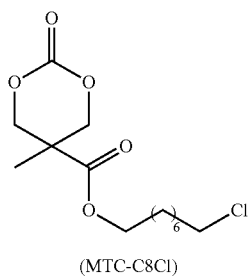
(MTC-C8Cl)

TABLE 1-continued
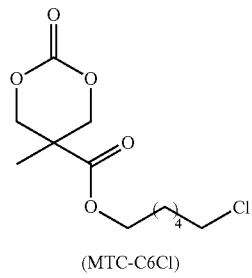
(MTC-C6Cl)
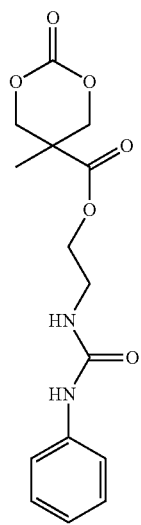
MTCU
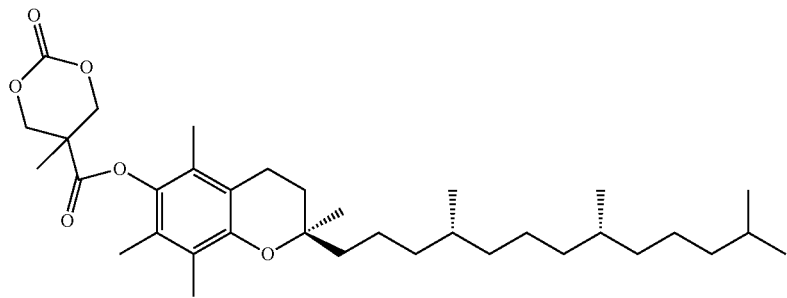
(MTC-VitE)
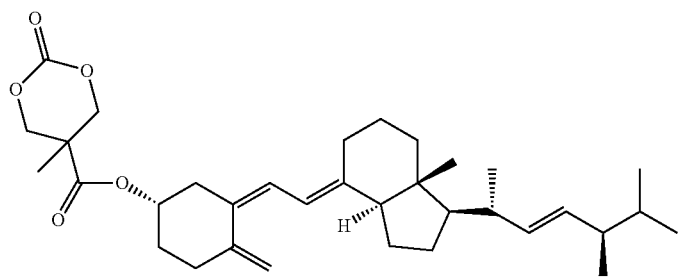
(MTC-VitD2)

TABLE 1-continued

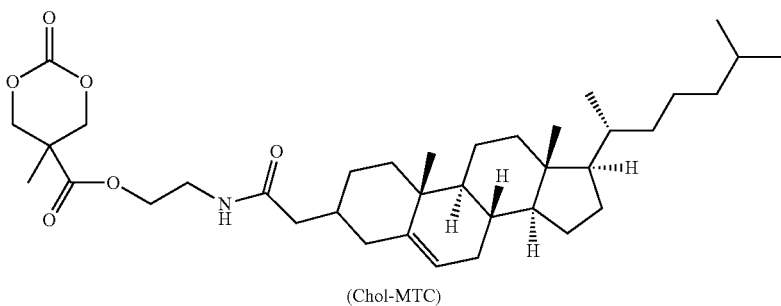

(Chol-MTC)

Non-limiting examples of cyclic ester comonomers include the compounds of Table 2.

TABLE 2

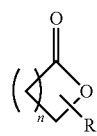

R = H; n = 1: beta-Propiolactone (b-PL)
R = H; n = 2: gamma-Butyrolactone (g-BL)
R = H; n = 3: delta-Valerolactone (d-VL)
R = H; n = 4: epsilon-Caprolactone (e-CL)
R = $CH_3$; n = 1: beta-Butyrolactone (b-BL)
R = $CH_3$; n = 2: gamma-Valerolactone (g-VL)

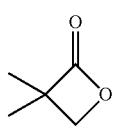

Pivalolactone
(PVL)

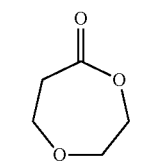

1,5-Dioxepan-2-one
(DXO)

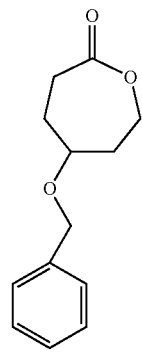

5-(Benzyloxy)oxepan-2-one
(BXO)

TABLE 2-continued

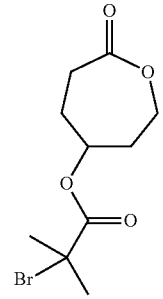

7-Oxooxepan-4-yl 2-bromo-2-methylpropanoate
(BMP-XO)

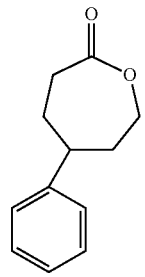

5-Phenyloxepan-2-one
(PXO)

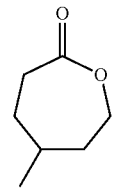

5-Methyloxepan-2-one
(MXO)

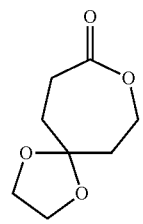

1,4,8-Trioxa(4,6)spiro-9-undecane
(TOSUO)

TABLE 2-continued

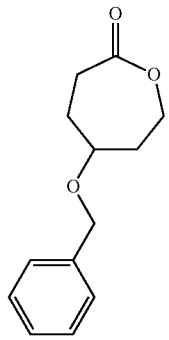

5-(Benzyloxymethyl)oxepan-2-one
(BOMXO)

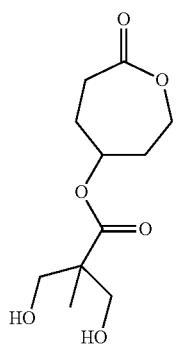

7-Oxooxepan-4-yl 3-hydroxy-2-
(hydroxymethyl)-2-methylpropanoate
(OX-BHMP)

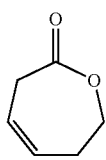

(Z)-6,7-Dihydrooxepin-2(3H)-one
(DHXO)

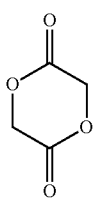

Glycolide
(GLY)

TABLE 2-continued

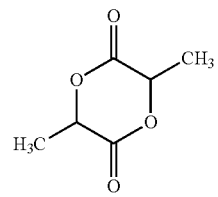

D-Lactide (DLA),
L-Lactide (LLA), or
racemic Lactide, 1:1 D:L forms (DLLA)

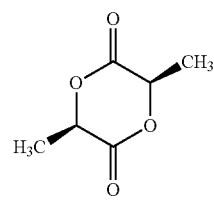

meso-Lactide (MLA)
(two opposite centers of asymmetry,
R and S)

Initiators for the ROP

Initiators for the ROP generally include alcohols, amines, and/or thiols. The initiator can comprise one or more nucleophilic groups capable of initiating a ring opening polymerization of the first cyclic monomer.

For the above described cationic polymers having one cationic polymer chain, the ROP initiator can be a mono-nucleophilic initiator comprising 1 to 50 carbons (e.g., ethanol, n-butanol, benzyl alcohol). The ROP initiator can be a biologically active compound selected from the group consisting of steroids, vitamins, and combinations thereof. For example, mono-nucleophilic ROP initiators include cholesterol, alpha-tocopherol, and ergocalciferol.

Other mono-nucleophilic ROP initiators comprise a covalently bound form of a biologically active compound. For example, the initiator can have a structure according to formula (I-1):

$$S'—L^e \qquad (I-1),$$

wherein S' is a steroid moiety or vitamin moiety, and $L^e$ is a monovalent group comprising i) 1 to about 10 carbons and ii) a nucleophilic initiating group for the ROP. Non-limiting examples of ROP initiators of formula (I-1) include Chol-OPrOH:

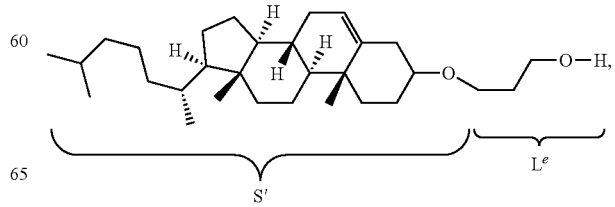

and Chol-OTEG-OH:

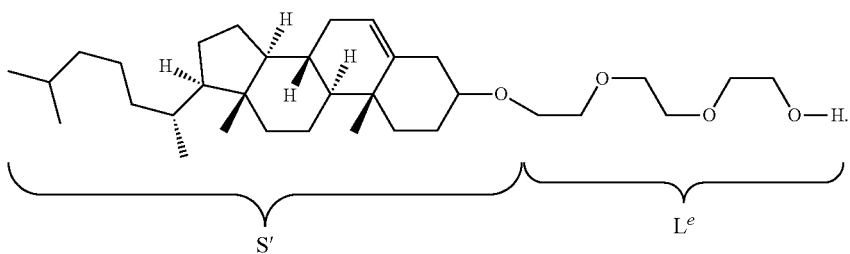

In the above examples, S' is a cholesteryl group.

The residue of the ROP initiator S'-$L^e$ initiator is denoted by S'-L'-*, which is linked to the carbonyl end of the initial polymer backbone. The S'-L'-* residue of Chol-OPrOH has the structure:

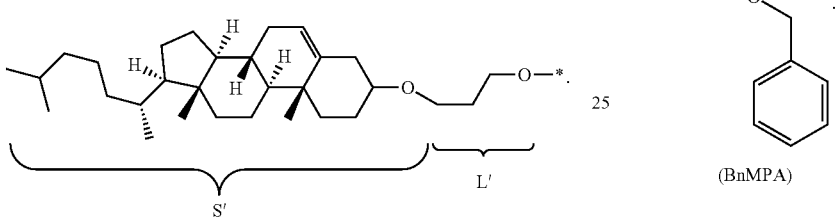

The S'-L'-* residue of Chol-OTEG-OH has the structure:

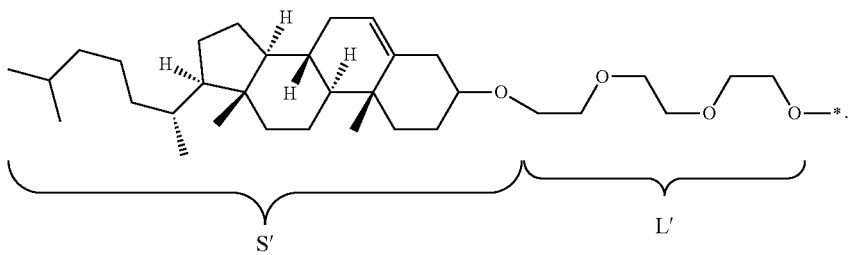

The initiator can be a mono-nucleophilic polyether initiator. Exemplary mono-nucleophilic polyether initiators include mono-endcapped poly(ethylene glycols) (e.g., mono-methyl poly(ethylene glycol) (mPEG-OH)) and mono-endcapped poly(propylene glycols). The polymeric initiator can comprise a nucleophilic chain end group independently selected from the group consisting alcohols, primary amines, secondary amines, and thiols.

The number average molecular weight (Mn) of the polyether initiator can be from 100 to 10000, and even more specifically, 1000 to 5000.

The ROP initiator can be used singularly or in combination with a different ROP initiator (e.g., initiators having different steroid groups and/or different $L^e$ groups.) The ROP initiator can be stereospecific or non-stereospecific.

The ROP initiator used to form cationic polymers having two polymer chains is a di-nucleophilic initiator. Exemplary di-nucleophilic ROP initiators include ethylene glycol, butanediol, 1,4-benzenedimethanol, and BnMPA:

(BnMPA)

An exemplary di-nucleophilic ROP initiator comprising a steroid group is Chol-MPA:

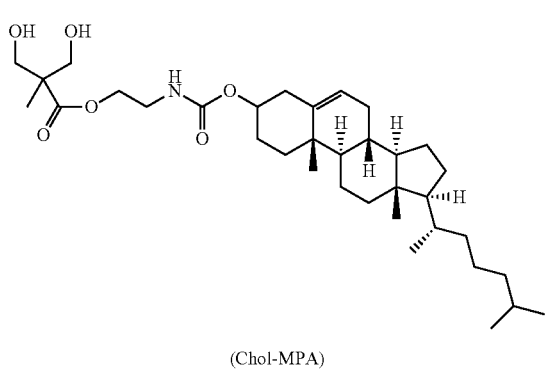

(Chol-MPA)

Exemplary di-nucleophilic polyether ROP initiators include poly(ethylene glycol) (referred to as PEG or HO-PEG-OH) having the structure HO—$[CH_2CH_2O]_n$—H and poly(propylene glycol) (referred to as PPG or HO-PPG-OH) having the structure HO—$[CH_2C(H)(CH_3)O]_n$—H, and copolyethers comprising ethylene oxide and propylene oxide repeat units. The number average molecular weight (Mn) of the dinucleophilic polyether initiator can be from 100 to 10000, and even more specifically, 1000 to 5000.

Initiators comprising 3 or more nucleophilic groups can be used to generate star polymers, graft polymers, and the like, which comprise 3 or more polymer chains Q'.

Endcap Agents

The living end (oxy end) of the initial polymer formed by the ROP has a reactive hydroxy group (second end group E'=H), which is capable of initiating another ROP. The living end can be treated with an endcap agent, thereby forming a different end group E', which is capable of preventing further chain growth and/or stabilizing the polymer against unwanted side reactions such as chain scission. The polymerization and endcapping can occur in the same pot without isolating the initial polymer. Endcap agents include, for example, materials for converting terminal hydroxy groups to esters, such as carboxylic acid anhydrides, carboxylic acid chlorides, and reactive esters (e.g., p-nitrophenyl esters). In an embodiment, the endcap agent is an acylating agent, and the second end group E' is an acyl group. In another embodiment the acylating agent is acetic anhydride, and the end group E' is an acetyl group. In another embodiment, the endcap agent comprises a covalently bound form of a steroid group, a vitamin, or a combination thereof.

Quaternizing Agents

No restriction is placed on the quaternizing agent. Exemplary non-limiting quaternizing agents include alkyl halides, alkyl sulfonates, and the like. The quaternizing agent can include a covalently bound form of a biologically active compound such as, for example a steroid, vitamin, and/or drug.

ROP Catalysts

Less preferred catalysts for a ROP polymerization include metal oxides such as tetramethoxy zirconium, tetra-iso-propoxy zirconium, tetra-iso-butoxy zirconium, tetra-n-butoxy zirconium, tetra-t-butoxy zirconium, triethoxy aluminum, tri-n-propoxy aluminum, tri-iso-propoxy aluminum, tri-n-butoxy aluminum, tri-iso-butoxy aluminum, tri-sec-butoxy aluminum, mono-sec-butoxy-di-iso-propoxy aluminum, ethyl acetoacetate aluminum diisopropylate, aluminum tris(ethyl acetoacetate), tetraethoxy titanium, tetra-iso-propoxy titanium, tetra-n-propoxy titanium, tetra-n-butoxy titanium, tetra-sec-butoxy titanium, tetra-t-butoxy titanium, tri-iso-propoxy gallium, tri-iso-propoxy antimony, tri-iso-butoxy antimony, trimethoxy boron, triethoxy boron, tri-iso-propoxy boron, tri-n-propoxy boron, tri-iso-butoxy boron, tri-n-butoxy boron, tri-sec-butoxy boron, tri-t-butoxy boron, tetramethoxy germanium, tetraethoxy germanium, tetra-iso-propoxy germanium, tetra-n-propoxy germanium, tetra-iso-butoxy germanium, tetra-n-butoxy germanium, tetra-sec-butoxy germanium and tetra-t-butoxy germanium; halogenated compounds such as antimony pentachloride, zinc chloride, lithium bromide, tin(IV) chloride, cadmium chloride and boron trifluoride diethyl ether; alkyl aluminum such as trimethyl aluminum, triethyl aluminum, diethyl aluminum chloride, ethyl aluminum dichloride and tri-iso-butyl aluminum; alkyl zinc such as dimethyl zinc, diethyl zinc and diisopropyl zinc; heteropolyacids such as phosphotungstic acid, phosphomolybdic acid, silicotungstic acid and alkali metal salts thereof; zirconium compounds such as zirconium acid chloride, zirconium octanoate, zirconium stearate, and zirconium nitrate.

Preferably, the chemical formula of the catalyst used for the ring opening polymerization does not include an ionic or nonionic form of a metal selected from the group consisting of beryllium, magnesium, calcium, strontium, barium, radium, aluminum, gallium, indium, thallium, germanium, tin, lead, arsenic, antimony, bismuth, tellurium, polonium, and metals of Groups 3 to 12 of the Periodic Table. Metals of Groups 3 to 12 of the Periodic Table include scandium, titanium, vanadium, chromium, manganese, iron, cobalt, nickel, copper, zinc, yttrium, zirconium, niobium, molybdenum, technetium, ruthenium, rhodium, palladium, silver, cadmium, lanthanum, cerium, praseodymium, neodymium, promethium, samarium, europium, gadolinium, terbium, dysprosium, holmium, erbium, thulium, ytterbium, lutetium, hafnium, tantalum, tungsten, rhenium, osmium, iridium, platinum, gold, mercury, actinium, thorium, protactinium, uranium, neptunium, plutonium, americium, curium, berkelium, californium, einsteinium, fermium, mendelevium, nobelium, lawrencium, rutherfordium, dubnium, seaborgium, bohrium, hassium, meitnerium, darmstadtium, roentgenium, and copernicium.

Preferred catalysts are organocatalysts whose chemical formulas contain none of the above metals. Examples of organocatalysts for ring opening polymerizations include tertiary amines such as triallylamine, triethylamine, tri-n-octylamine and benzyldimethylamine 4-dimethylaminopyridine, phosphines, N-heterocyclic carbenes (NHC), bifunctional aminothioureas, phosphazenes, amidines, and guanidines.

A more specific organocatalyst is N-bis(3,5-trifluoromethyl)phenyl-N'-cyclohexylthiourea (TU):

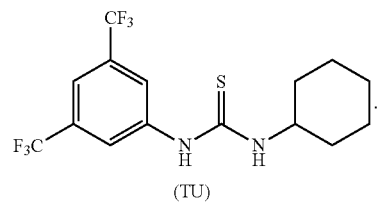

(TU)

Other ROP organocatalysts comprise at least one 1,1,1,3,3,3-hexafluoropropan-2-ol-2-yl (HFP) group. Singly-donating hydrogen bond catalysts have the formula (28):

$$R^2-C(CF_3)_2OH \qquad (C-1),$$

wherein $R^2$ represents a hydrogen or a monovalent radical having 1 to 20 carbons, for example an alkyl group, substituted alkyl group, cycloalkyl group, substituted cycloalkyl group, heterocycloalkyl group, substituted heterocycloalkyl group, aryl group, substituted aryl group, or a combination thereof. Exemplary singly-donating hydrogen bonding catalysts are listed in Table 3.

TABLE 3

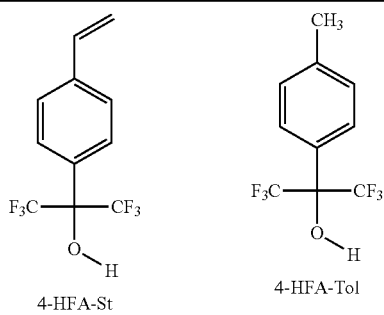

TABLE 3-continued

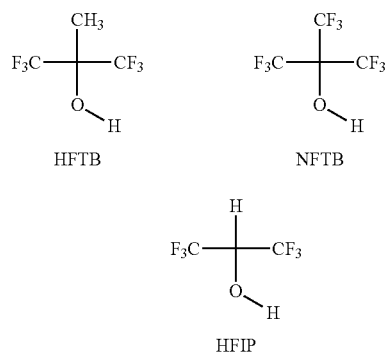

HFTB NFTB HFIP

Doubly-donating hydrogen bonding catalysts have two HFP groups, represented by the formula (29):

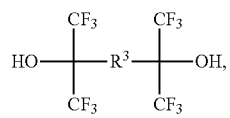
(C-2)

wherein $R^3$ is a divalent radical bridging group comprising 1 to 20 carbons, such as an alkylene group, a substituted alkylene group, a cycloalkylene group, substituted cycloalkylene group, a heterocycloalkylene group, substituted heterocycloalkylene group, an arylene group, a substituted arylene group, and a combination thereof. Representative double hydrogen bonding catalysts of formula (C-2) include those listed in Table 4. In a specific embodiment, $R^2$ is an arylene or substituted arylene group, and the HFP groups occupy positions meta to each other on the aromatic ring.

TABLE 4

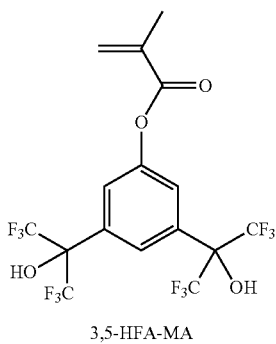 [SMILES: C=C(C)C(=O)Oc1cc(C(O)(C(F)(F)F)C(F)(F)F)cc(C(O)(C(F)(F)F)C(F)(F)F)c1]

3,5-HFA-MA 3,5-HFA-St

TABLE 4-continued

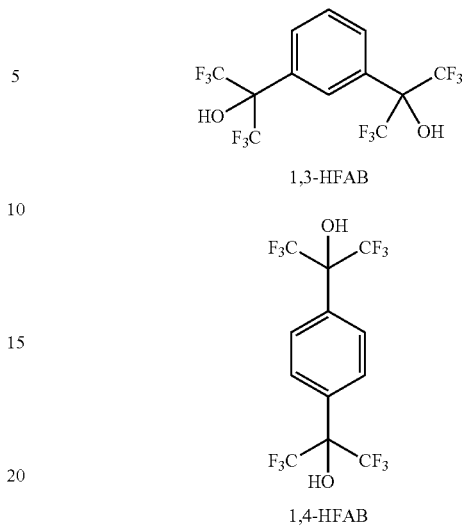

1,3-HFAB 1,4-HFAB

In one embodiment, the catalyst is selected from the group consisting of 4-HFA-St, 4-HFA-Tol, HFTB, NFTB, HPIP, 3,5-HFA-MA, 3,5-HFA-St, 1,3-HFAB, 1,4-HFAB, and combinations thereof.

Also contemplated are catalysts comprising HFP-containing groups bound to a support. In one embodiment, the support comprises a polymer, a crosslinked polymer bead, an inorganic particle, or a metallic particle. HFP-containing polymers can be formed by known methods including direct polymerization of an HFP-containing monomer (for example, the methacrylate monomer 3,5-HFA-MA or the styryl monomer 3,5-HFA-St). Functional groups in HFP-containing monomers that can undergo direct polymerization (or polymerization with a comonomer) include acrylate, methacrylate, alpha, alpha, alpha-trifluoromethacrylate, alpha-halomethacrylate, acrylamido, methacrylamido, norbornene, vinyl, vinyl ether, and other groups known in the art. Examples of linking groups include $C_1$-$C_{12}$ alkyl, a $C_1$-$C_{12}$ heteroalkyl, ether group, thioether group, amino group, ester group, amide group, or a combination thereof. Also contemplated are catalysts comprising charged HFP-containing groups bound by ionic association to oppositely charged sites on a polymer or a support surface.

The ROP reaction mixture comprises at least one organocatalyst and, when appropriate, several organocatalysts together. The ROP catalyst is added in a proportion of 1/20 to 1/40,000 moles relative to the cyclic carbonyl monomers, and preferably in a proportion of 1/1,000 to 1/20,000 moles relative to the cyclic carbonyl monomers.

ROP Accelerators

The ROP polymerization can be conducted in the presence of an optional accelerator, in particular a nitrogen base. Exemplary nitrogen base accelerators are listed below and include pyridine (Py), N,N-dimethylaminocyclohexane (Me$_2$NCy), 4-N,N-dimethylaminopyridine (DMAP), trans 1,2-bis(dimethylamino)cyclohexane (TMCHD), 1,8-diazabicyclo[5.4.0]undec-7-ene (DBU), 1,5,7-triazabicyclo[4.4.0]dec-5-ene (TBD), 7-methyl-1,5,7-triazabicyclo[4.4.0]dec-5-ene (MTBD), (-)-sparteine, (Sp) 1,3-bis(2-propyl)-4,5-dimethylimidazol-2-ylidene (Im-1), 1,3-bis(2,4,6-trimethylphenyl)imidazol-2-ylidene (Im-2), 1,3-bis(2,6-di-i-propylphenyl)imidazol-2-ylidene (Im-3), 1,3-bis(1-adamantyl)imidazol-2-ylidene (Im-4), 1,3-di-i- propylimidazol-2-ylidene (Im-5), 1,3-di-t-butylimidazol-2-ylidene (Im-6), 1,3-bis(2,4,6-trimethylphenyl)-4,5-dihydroimidazol-2-ylidene (Im-7), 1,3-bis(2,6-di-i-propylphenyl)-4,5-dihydroimidazol-2-ylidene, 1,3-bis(2,6-di-i-propylphenyl)-4,5-dihydroimidazol-2-ylidene (Im-8) or a combination thereof, shown in Table 5.

TABLE 5

Pyridine
(Py)

N,N-Dimethylaminocyclohexane
(Me₂NCy)

4-N,N-Dimethylaminopyridine
(DMAP)

trans 1,2-Bis(dimethylamino)cyclohexane
(TMCHD)

1,8-Diazabicyclo[5.4.0]undec-7-ene
(DBU)

7-Methyl-1,5,7-triazabicyclo[4.4.0]dec-5-ene
(MTBD)

1,5,7-Triazabicyclo[4.4.0]dec-5-ene
(TBD)

TABLE 5-continued

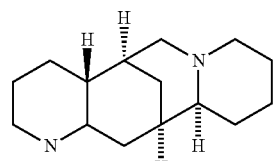

(-)-Sparteine
(Sp)

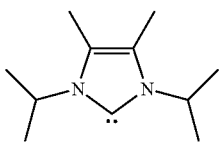

1,3-Bis(2-propyl)-4,5-dimethylimidazol-2-ylidene
(Im-1)

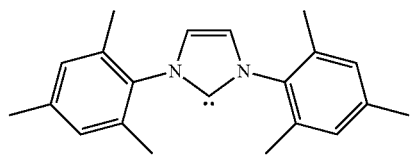

1,3-Bis(2,4,6-trimethylphenyl)imidazol-2-ylidene
(Im-2)

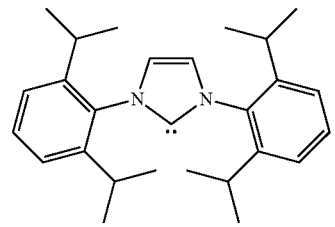

1,3-Bis(2,6-di-i-propylphenyl)imidazol-2-ylidene
(Im-3)

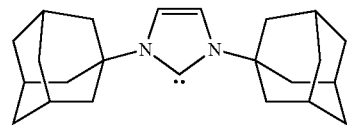

1,3-Bis(1-adamantyl)imidazol-2-yliden)
(Im-4)

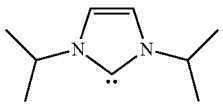

1,3-Di-i-propylimidazol-2-ylidene
(Im-5)

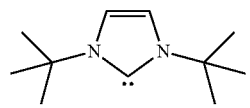

1,3-Di-i-butylimidazol-2-ylidene
(Im-6)

TABLE 5-continued

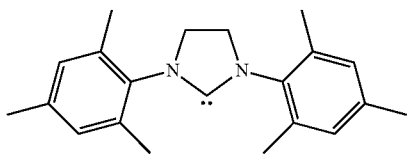

1,3-Bis(2,4,6-trimethylphenyl)-4,5-dihydroimidazol-2-ylidene
(Im-7)

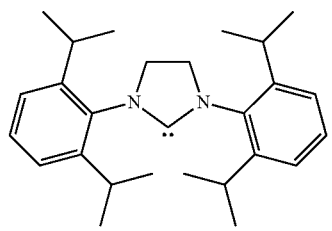

1,3-Bis(2,6-di-i-propylphenyl)-4,5-dihydroimidazol-2-ylidene
(Im-8)

In an embodiment, the accelerator has two or three nitrogens, each capable of participating as a Lewis base, as for example in the structure (-)-sparteine. Stronger bases generally improve the polymerization rate.

The catalyst and the accelerator can be the same material. For example, some ring opening polymerizations can be conducted using 1,8-diazabicyclo[5.4.0]undec-7-ene (DBU) alone, with no another catalyst or accelerator present.

The catalyst is preferably present in an amount of about 0.2 to 20 mol %, 0.5 to 10 mol %, 1 to 5 mol %, or 1 to 2.5 mol %, based on total moles of cyclic carbonyl monomer.

The nitrogen base accelerator, when used, is preferably present in an amount of 0.1 to 5.0 mol %, 0.1 to 2.5 mol %, 0.1 to 1.0 mol %, or 0.2 to 0.5 mol %, based on total moles of cyclic carbonyl monomer. As stated above, in some instances the catalyst and the nitrogen base accelerator can be the same compound, depending on the particular cyclic carbonyl monomer.

The initiator groups are preferably present in an amount of 0.001 to 10.0 mol %, 0.1 to 2.5 mol %, 0.1 to 1.0 mol %, or 0.2 to 0.5 mol %, based on total moles of cyclic carbonyl monomer.

In a specific embodiment, the catalyst is present in an amount of about 0.2 to 20 mol %, the nitrogen base accelerator is present in an amount of 0.1 to 5.0 mol %, and the nucleophilic initiator groups of the initiator are present in an amount of 0.1 to 5.0 mol % based on total moles of cyclic carbonate monomer.

The catalysts can be removed by selective precipitation or, in the case of the solid supported catalysts, by filtration. The catalyst can be present in an amount of 0 wt % (weight percent) to about 20 wt %, preferably 0 wt % (weight percent) to about 0.5 wt % based on the total weight of the cationic polymer and the residual catalyst. The cationic polymer preferably comprises no residual catalyst.

Average Molecular Weight

The cationic polymers have a number average molecular weight (Mn) as determined by size exclusion chromatography of about 1500 to about 50,000, more specifically about 1500 to about 30,000. The precursor polymer to the cationic polymer and/or the cationic polymer preferably has a poly-dispersity index (PDI) of 1.01 to about 1.5, more particularly 1.01 to 1.30, and even more particularly 1.01 to 1.25.

In some instances, the cationic polymers can self-assemble into nanoparticulate micelles in de-ionized water. The cationic polymers can have a critical micelle concentration (CMC) of about 15 mg/L to about 500 mg/L.

Utility

The micelles can have a minimum inhibitory concentration (MIC) for microbial growth of about 7 mg/L to about 500 mg/L. The MIC can be below the CMC, meaning the antimicrobial activity is not dependent on self-assembly of the cationic polymers. In an embodiment, the cationic polymer comprises a homopolymer of the cationic repeat.

Further disclosed is a method of treating a microbe, comprising contacting a microbe with a disclosed cationic polymer, thereby killing the microbe.

For the examples below, the following definitions are applicable.

HC50 is defined as the concentration (in mg/L) of cationic polymer that causes 50% of mammalian red blood cells to undergo hemolysis. HC50 values of 500 mg/L or higher are desirable.

HC20 is defined as the concentration (in mg/L) of cationic polymer that causes 20% of mammalian red blood cells to undergo hemolysis. HC20 values of 500 mg/L or higher are desirable.

Minimum inhibitory concentration (MIC) is defined as the minimum concentration (in mg/L) of cationic polymer required to inhibit growth of a given microbe for an eighteen hour period. A MIC less than 500 mg/L is desirable. Even more desirable is a MIC of 250 mg/L or less. A lower MIC indicates higher antimicrobial activity.

Minimum bactericidal concentration (MBC) is defined as the minimum concentration (in mg/L) of cationic polymer required to kill a given microbe at >99.9% efficiency over 18 hours. A lower MBC indicates higher antimicrobial activity.

HC50 selectivity is defined as the ratio of HC50/MIC. An HC50 selectivity of 3 or more is desirable. Higher HC50 selectivity values indicate more activity against microbial cells and less toxicity to mammalian cells. Likewise, HC20 selectivity is defined as the ratio of HC20/MIC. An HC20 selectivity of 3 or more is desirable.

Non-limiting microbes include Gram-positive *Staphylococcus epidermidis* (*S. epidermidis*), Gram-positive *Staphylococcus aureus* (*S. aureus*), Gram-negative *Escherichia coli* (*E. coli*), Gram-negative *Pseudomonas aeruginosa* (*P. aeruginosa*), fungus *Candida albicans* (*C. albicans*), Gram-positive Methicillin-resistant *Staphylococcus aureus* (MRSA), Gram-positive Vancomycin-resistant *Enterococcus* (VRE), Gram-negative *Acinetobacter baumannii* (*A. baumannii*), yeast *Cryptococcus neoformans* (*C. neoformans*), and Gram-negative *Klebsiella pneumoniae* (*K. pneumoniae*).

The cationic polymers are generally non-hemolytic up to 1000 mg/L (1000 ppm). The cationic polymers can also be non-cytotoxic at concentrations up to 1000 micrograms per milliliter. In some cases, cell viability of human fibroblast cells incubated with the cationic polymers was more than 90%. The cationic polymers can also inhibit or eradicate a biofilm.

The biodegradability, low average mass, high antimicrobial activity, and low cytotoxicity make these cationic polymers highly attractive for a wide range of medical and household uses, including wound treatments, treatment of infections, antibiotic drugs, and disinfectants for household and hospital surfaces and medical instruments. In an embodiment, a medical composition comprises one or more of the disclosed cationic polymers. The medical composition can comprise water, and the concentration of the cationic polymer can be below the critical micelle concentration of the cationic polymer. The medical composition can be a drug. The drug can be a solution, gel, powder, pill, paste, or ointment. The drug can be delivered orally, by injection, by spray, by inhalant, by dermal patch, and/or as a topically applied ointment.

The following examples demonstrate the preparation and properties of the cationic polymers.

EXAMPLES

Materials used in the following examples are listed in Table 6.

TABLE 6

| ABBREVIATION | DESCRIPTION | SUPPLIER |
|---|---|---|
| Me-DEA | N-methyl Diethanolamine | Sigma-Aldrich |
| Bu-DEA | N-Butyl Diethanolamine | Sigma-Aldrich |
| Bn-DEA | N-Benzyl Diethanolamine | Sigma-Aldrich |
| tBu-DEA | N-tert-Butyl Diethanolamine | Sigma-Aldrich |
| Ph-DEA | N-Phenyl Diethanolamine | Sigma-Aldrich |
| Ac-DEA | N-Acetyl Diethanolamine | prepared below |
| BOC-DEA | N-BOC Diethanolamine | Sigma-Aldrich |
|  | Diethylene Glycol | Sigma-Aldrich |
|  | 2,2'-Thiodiethanol | Sigma-Aldrich |
|  | 1,5-Pentanediol | Sigma-Aldrich |
| DBU | 1,8-Diazabicyclo[5,4,0]undec-7-ene | Sigma-Aldrich |
|  | p-Chloromethyl Benzyl Alcohol | Sigma-Aldrich |
| TMA | Trimethylamine | Sigma-Aldrich |
| DCM | Dichloromethane | Sigma-Aldrich |

Herein, Mn is the number average molecular weight, Mw is the weight average molecular weight, and MW is the molecular weight of one molecule.

N-(3,5-trifluoromethyl)phenyl-N'-cyclohexyl-thiourea (TU) was prepared as reported by R. C. Pratt, B. G. G. Lohmeijer, D. A. Long, P. N. P. Lundberg, A. Dove, H. Li, C. G. Wade, R. M. Waymouth, and J. L. Hedrick, Macromolecules, 2006, 39 (23), 7863-7871, and dried by stirring in dry THF over $CaH_2$, filtering, and removing solvent under vacuum.

Monomer Synthesis

N-Acetyl diethanolamine was prepared according to the following procedure. A flask was charged with diethanolamine (10 g, 95.1 mmol), triethylamine (13.3 mL, 95.1 mmol) and methanol (75 mL). The reaction mixture was cooled to 0° C. and acetic anhydride (9.2 g, 90.0 mmol) was added dropwise. The mixture was stirred 2 hours, warmed to room temperature, and allowed to stir overnight. Volatiles were removed, the crude product was dissolved in ethyl acetate (100 mL) and washed with 10% HCl (3×), saturated potassium carbonate (3×) and brine. The solvent was removed yielding 9.2 g (66%) yellow oil.

BnMPA has the following structure:

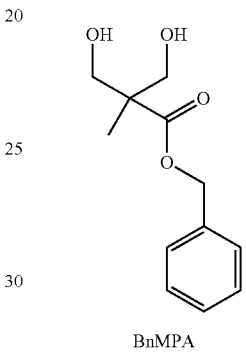

BnMPA

BnMPA and other cyclic carbonate monomers can be prepared from 2,2-bis(methylol)propionic (BisMPA) according to Scheme 1.

Scheme I.

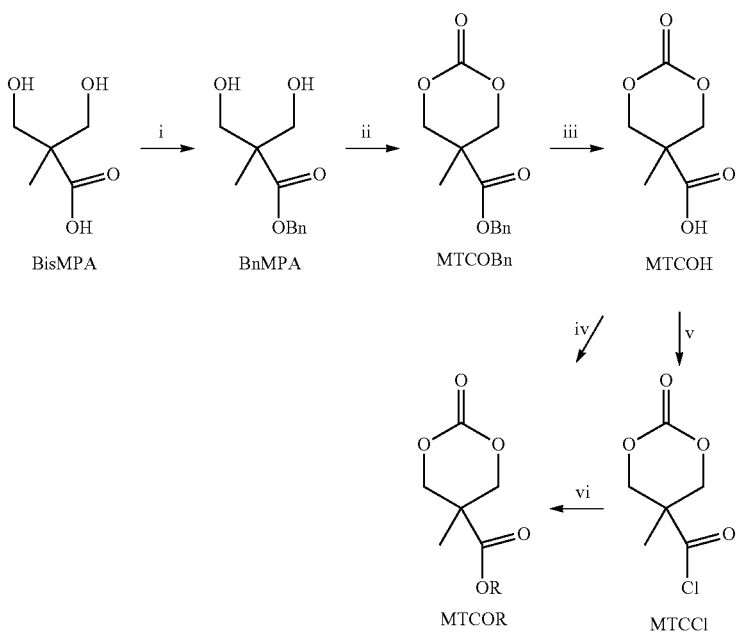

BisMPA can be converted (i) to the benzyl ester BnMPA using known methods. Reaction of BnMPA with triphosgene (ii) produces cyclic carbonyl monomer, MTCOBn. Debenzylation of MTCOBn (iii) produces 5-methyl-5-carboxyl-1,3-dioxan-2-one (MTCOH). Two pathways are shown for forming an ester from MTCOH. In the first pathway, (iv), MTCOH is treated with a suitable carboxy activating agent, such as dicyclohexylcarbodiimide (DCC), which reacts with ROH to form MTCOR in a single step. Alternatively, MTCOH can be converted first (v) to the acid chloride MTCCl followed by treatment (vi) of MTCCl with ROH in the presence of a base to form MTCOR. Both pathways are illustrative and are not meant to be limiting. The following conditions are typical for the reactions shown in Scheme 1: (i) Benzylbromide (BnBr), KOH, DMF, 100° C., 15 hours, 62% yield of BnMPA; (ii) triphosgene, pyridine, $CH_2Cl_2$, 78° C. to 0° C., 95% yield of MTCOBn; (iii) Pd/C (10%), $H_2$ (3 atm), EtOAc, room temperature, 24 hours, 99% yield of MTCOH; (iv) ROH, DCC, THF, room temperature, 1 to 24 hours; (v) $(COCl)_2$, THF, room temperature, 1 hour, 99% yield of MTCCl; (vi) ROH, $NEt_3$, room temperature, 3 hours yields MTCOR.

Example 1. Preparation of
6-Methyl-1,3,6-Dioxazocan-2-One (DXA-Me)

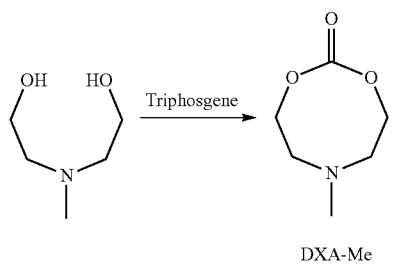

DXA-Me

A round bottom flask was charged with N-methyl diethanolamine (10.0 g, 83.9 mmol), triethylamine (24.0 mL, 167.8 mmol), dry tetrahydrofuran (THF) (600 mL) and stirbar. The reaction flask was cooled to −20° C. under a nitrogen atmosphere. Separately, triphosgene (8.3 g, 28.8 mmol) was dissolved in dry THF (100 mL) and added slowly to the reaction mixture. A white precipitate formed instantly and stirring was continued for another 2 hours maintaining a reaction temperature less than 10° C. Diethyl ether (800 mL) was added to further precipitate any remaining HCl salts followed by filtration of the heterogeneous solution. The filtrate was concentrated yielding a yellow/brown oil product (10.4 g, 85%).

Example 2. Preparation of
6-Butyl-1,3,6-Dioxazocan-2-One (DXA-Bu)

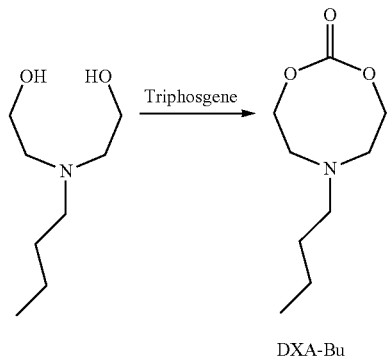

DXA-Bu

The procedure of Example 1 was followed using N-butyl diethanolamine (13.5 g, 83.9 mmol), triethylamine (24.0 mL, 167.8 mmol), dry THF (600 mL) and triphosgene (8.3 g, 28.8 mmol). The filtrate was concentrated yielding a yellow/brown oil product (12.9 g, 82%).

Example 3. Preparation of
6-Benzyl-1,3,6-Dioxazocan-2-One (DXA-Bn)

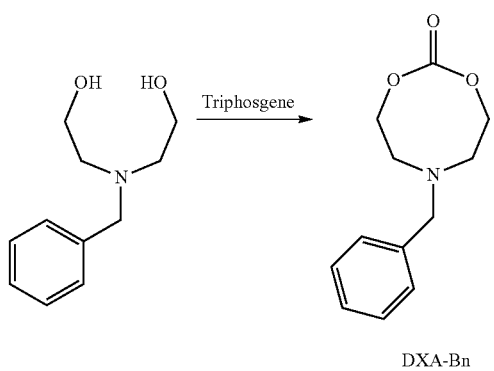

DXA-Bn

The procedure of Example 1 was followed using N-benzyl diethanolamine (16.4 g, 83.9 mmol), triethylamine (24.0 mL, 167.8 mmol), dry THF (600 mL) and triphosgene (8.3 g, 28.8 mmol). The filtrate was concentrated yielding a yellow oil product (14.5 g, 78%).

Comparative Example 4. Preparation of 6-Tert-Butyl-1,3,6-Dioxazocan-2-One (DXA-tBu)

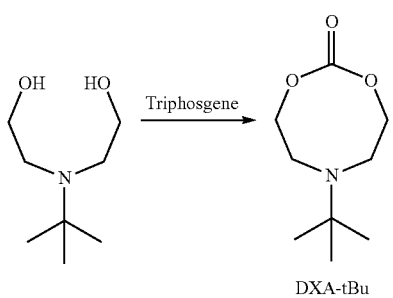

The procedure of Example 1 was followed using N-tert-butyl diethanolamine (16.4 g, 83.9 mmol), triethylamine (24.0 mL, 167.8 mmol), dry THF (600 mL) and triphosgene (8.3 g, 28.8 mmol). The filtrate was concentrated yielding a clear oil containing a non-isolable amount of product within a mixture of oligomeric diethanolamines.

Example 5. Preparation of 6-Phenyl-1,3,6-Dioxazocan-2-One (DXA-Ph)

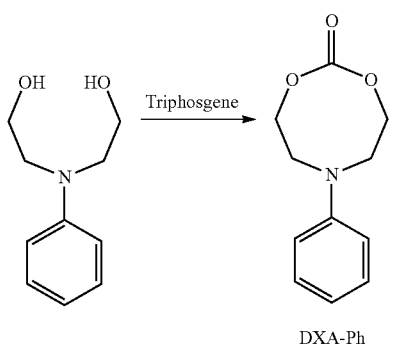

The procedure of Example 1 was followed using N-phenyldiethanolamine (15.2 g, 83.9 mmol), triethylamine (24.0 mL, 167.8 mmol), dry THF (600 mL) and triphosgene (8.3 g, 28.8 mmol). The filtrate was concentrated yielding a clear oil containing a mixture of products. The product was purified using a column chromatography EtOAc:Hexanes (3:1) yielding 3.3 g (19%) of a clear oil which turned brown over time.

Comparative Example 6. Attempted Preparation of 6-Acetyl-1,3,6-Dioxazocan-2-One (DXA-Ac)

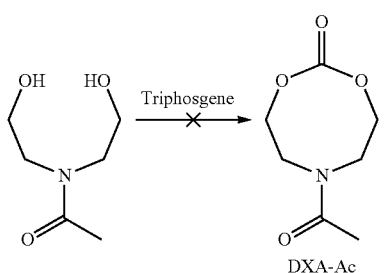

The procedure of Example 1 was followed using N-acetyl diethanolamine (12.3 g, 83.9 mmol), triethylamine (24.0 mL, 167.8 mmol), dry THF (600 mL) and triphosgene (8.3 g, 28.8 mmol). The filtrate was concentrated yielding only oligomeric compounds.

Comparative Example 7. Attempted Preparation of 6-Boc-1,3,6-Dioxazocan-2-One (DXA-Boc)

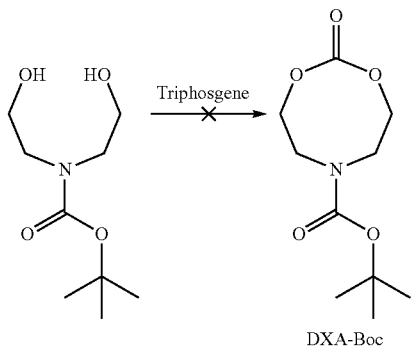

The procedure of Example 1 was followed using N-boc diethanolamine (3 g, 14.6 mmol), triethylamine (4.1 mL, 29.2 mmol), dry dichloromethane (100 mL) and triphosgene (1.4 g, 4.9 mmol). The filtrate was concentrated yielding only oligomeric compounds.

Comparative Example 8. Attempted Preparation of 1,3,6-Trioxocan-2-One (TXA)

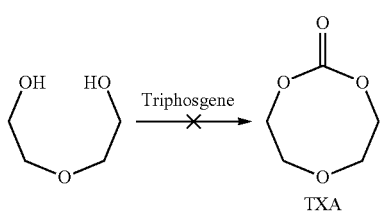

The procedure of Example 1 was followed using diethylene glycol (8.9 g, 83.9 mmol), triethylamine (24.0 mL, 167.8 mmol), dry THF (600 mL) and triphosgene (8.3 g, 28.8 mmol). The filtrate was concentrated yielding only oligomeric compounds.

Comparative Example 9. Attempted Preparation of 1,3,6-Dioxathiocan-2-One (DXT)

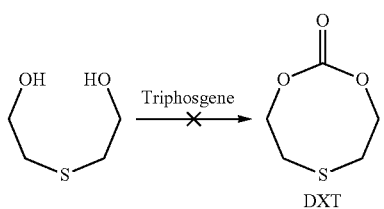

The procedure of Example 1 was followed using 2,2'-thiodiethanol (10.2 g, 83.9 mmol), triethylamine (24.0 mL, 167.8 mmol), dry THF (600 mL) and triphosgene (8.3 g, 28.8 mmol). The filtrate was concentrated yielding only oligomeric compounds.

Comparative Example 10. Attempted Preparation of Pentamethylene Carbonate (PMC)

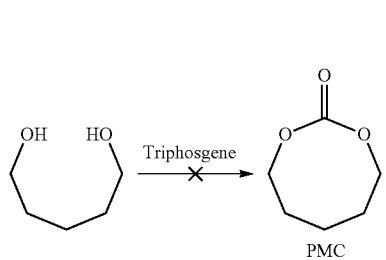

The procedure of Example 1 was followed using 1,5-pentanediol (1 g, 9.6 mmol), triethylamine (2.8 mL, 20.2 mmol), dry THF (100 mL) and triphosgene (0.96 g, 3.24 mmol). The filtrate was concentrated yielding only oligomeric compounds.

Cyclizations of the above diols were also attempted using ethyl chloroformate, and bis(pentafluorophenyl) carbonate (PFC). Table 7 summarizes the results.

Using the following structure as a guide,

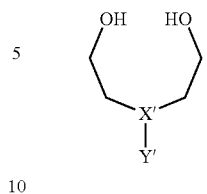

the results in Table 7 indicate that cyclization to form 8-membered cyclic carbonates using triphosgene, bis(pentafluorophenyl) carbonate, and ethyl chloroformate is favored when X' is nitrogen and Y' is a methyl group or a group comprising a methylene group linked directly to X'.

Ring Opening Polymerizations

Examples 11-14 Preparation of P-4, Example 14 is Representative

TABLE 7

| | | | Cyclization Yield (%) | | | |
|---|---|---|---|---|---|---|
| Example | Diol | Cyclization Product | Triphosgene | Ethyl Chloroformate | PFC | Cyclic Product Polymerizable? |
| 1 | N-Methyl diethanolamine | DXA-Me | 85 | >95 | >95 | yes |
| 2 | N-Butyl diethanolamine | DXA-Bu | 82 | n/a | n/a | yes |
| 3 | N-Benzyl diethanolamine | DXA-Bn | 78 | n/a | n/a | yes |
| 4 | N-tert-Butyl diethanolamine | DXA-tBu | 0 | 0 | 0 | n/a |
| 5 | N-Phenyl diethanolamine | DXA-Ph | 19[a] | 0 | 0 | yes |
| 6 | N-Acetyl diethanolamine | DXA-Ac | 0 | 0 | 0 | n/a |
| 7 | N-Boc-diethanolamine | DXA-Boc | 0 | 0 | 0 | n/a |
| 8 | Diethylene Glycol | TXA | 0 | 0 | 0 | n/a |
| 9 | Thiodiethanol | DXT | 0 | 0 | 0 | n/a |
| 10 | 1,5-pentanediol | PMC | 0 | 0 | 0 | n/a |

[a]multiple derivatives reported
[b]n/a = not attempted

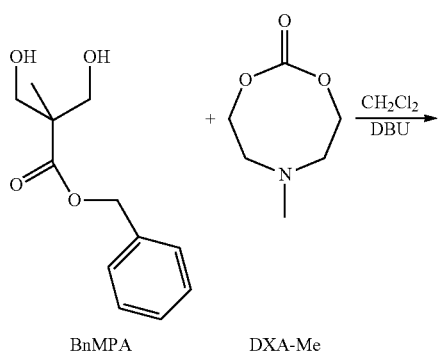

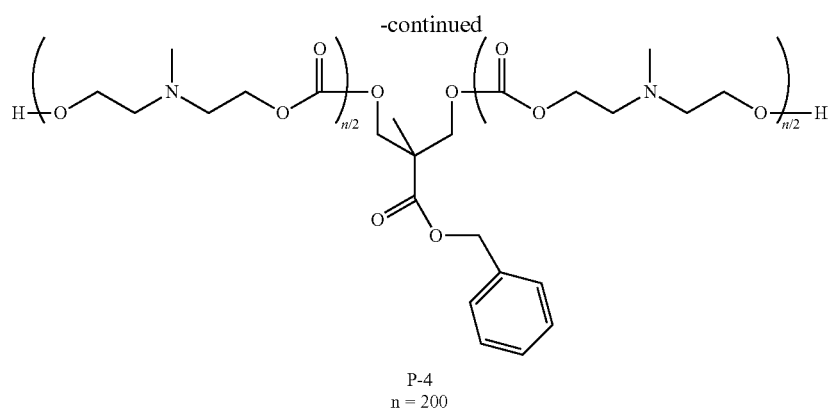

P-4
n = 200

In a nitrogen filled glove box a vial was charged with BnMPA (0.0039 g, 0.0172 mmol), 6-methyl-1,3,6-dioxazocan-2-one (0.5 g, 3.44 mmol), dichloromethane (1.5 g) and a stirbar. The polymerization was initiated via addition of DBU (0.016 mL, 0.1 mmol). After complete monomer conversion (~18 hours) the reaction mixture was precipitated into diethyl ether and collected by centrifugation yielding 0.48 g (96%) white amorphous polymer (Mn 20 kDa; PDI 1.14, n=200).

Using the above procedure, a molecular weight series was generated by varying the amount of initiator BnMPA with respect to the cyclic carbonate monomer DXA-Me, summarized in Table 8 below. FIG. 1 is a graph of Mn as a function of average degree of polymerization (DP) for polymers P-1 to P-4.

Example 15. Preparation of P-5

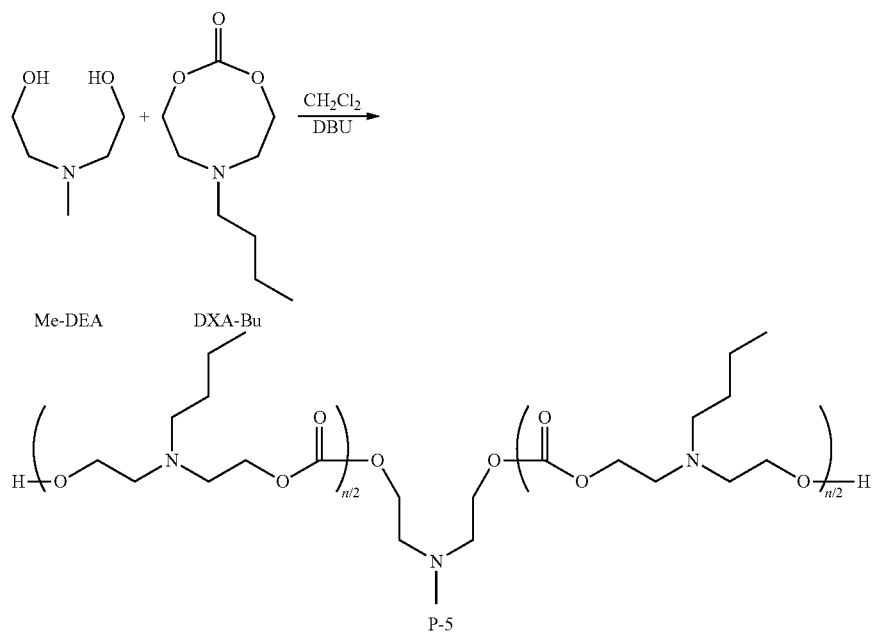

P-5

Polymer P-5 was prepared using DXA-Bu and Me-DEA as the dinucleophilic initiator. In a nitrogen filled glovebox a vial was charged with Me-DEA (0.0032 g, 0.026 mmol), DXA-Bu (1.0 g, 5.34 mmol) and DCM (1.5 g). The polymerization was initiated by the addition of DBU (0.080 mL, 0.53 mmol). The reaction mixture was stirred until complete monomer consumption followed by immediate precipitation into ether, yielding 0.91 g (90%) of off-white polymer; Mn=30.0 kDa, PDI-1.22, n=200.

Example 16. Preparation of P-6

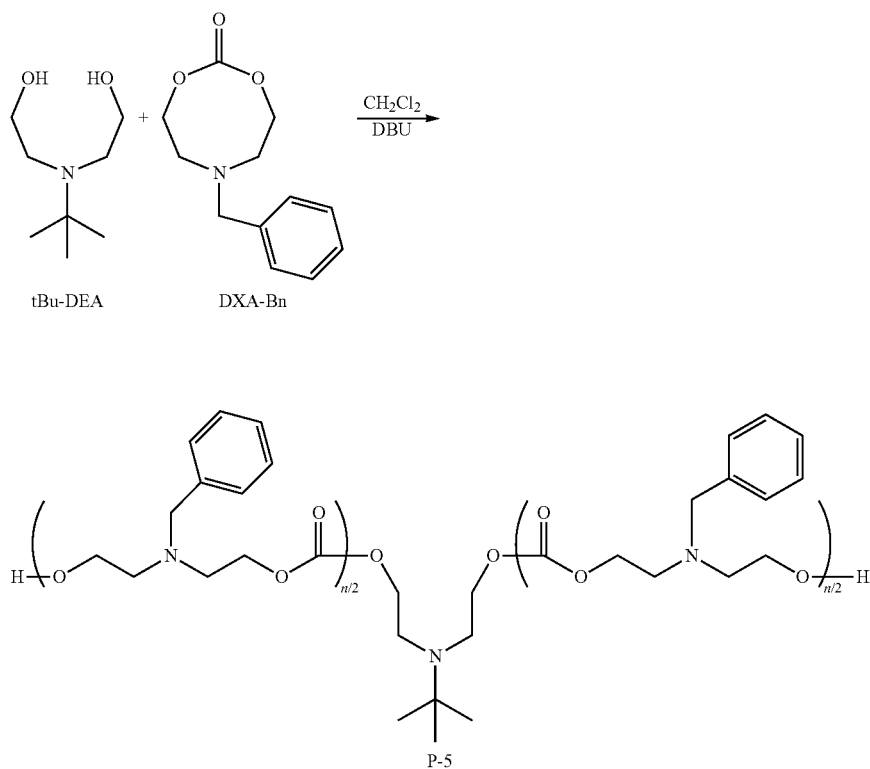

Polymer P-6 was prepared using DXA-Bn and tBu-DEA as the dinucleophilic initiator. In a nitrogen filled glovebox a vial was charged with tBu-DEA (0.0044 g, 0.027 mmol), DXA-Bn (0.30 g, 1.35 mmol) and DCM (0.65 g). The polymerization was initiated by the addition of DBU (0.021 mL, 0.135 mmol). The reaction mixture was stirred until complete monomer consumption followed by immediate precipitation into ether, yielding 0.28 g (93%) of off-white polymer; Mn=17.5 kDa, PDI-1.36, n=50.

Table 8 summarizes polymers P-1 to P-6. DP is the average degree of polymerization, Mn is the number average molecular weight, PDI is polydispersity (Mw/Mn).

TABLE 8

| Example | Name | Monomer | Monomer (mmol) | Initiator | Initiator (mmol) | Yield (%) | DP (n) | Mn | PDI |
|---|---|---|---|---|---|---|---|---|---|
| 11 | P-1 | DXA-Me | 3.44 | BnMPA | 0.0172 | 93 | 20 | 3646 | 1.09 |
| 12 | P-2 | DXA-Me | 3.44 | BnMPA | 0.0172 | 95 | 50 | 7924 | 1.09 |
| 13 | P-3 | DXA-Me | 3.44 | BnMPA | 0.0172 | 95 | 100 | 13544 | 1.11 |
| 14 | P-4 | DXA-Me | 3.44 | BnMPA | 0.0172 | 92 | 200 | 25300 | 1.17 |
| 15 | P-5 | DXA-Bu | 3.44 | Me-DEA | 0.0172 | 90 | 50 | 11600 | 1.22 |
| 16 | P-6 | DXA-Bn | 3.44 | tBu-DEA | 0.0172 | 93 | 50 | 17500 | 1.36 |

Quaternization

Examples 17-19

The following procedure to form quaternary polymer Q-3 from P-4 (Example 19) is representative.

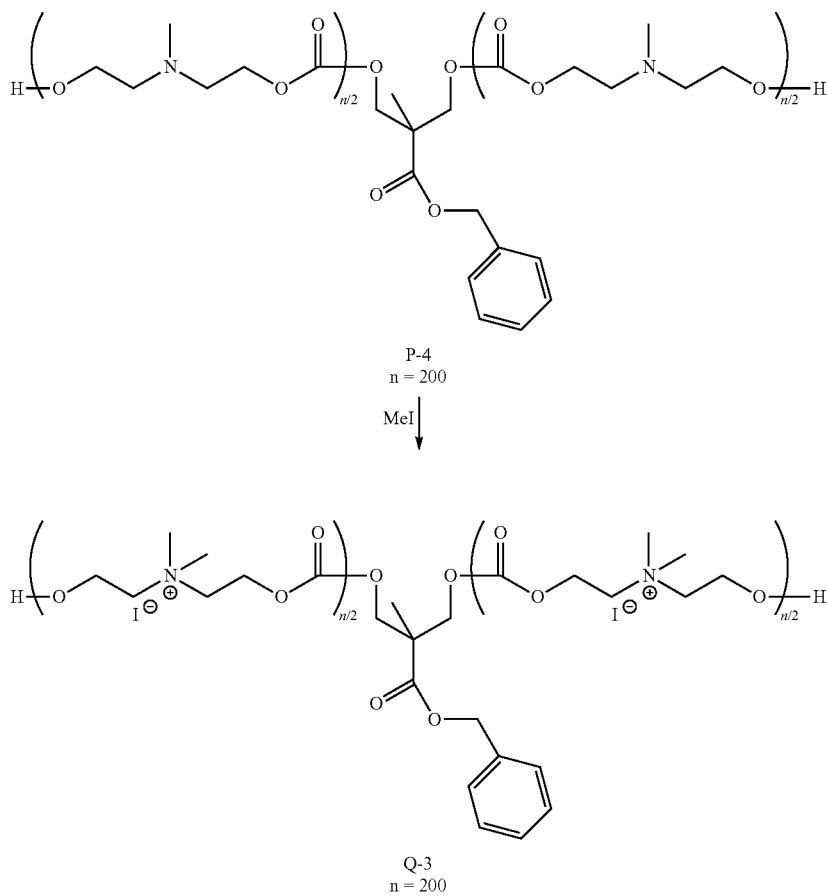

P-4
n = 200

Q-3
n = 200

A vial was charged with P-4 (1 g, 8.4 mmol eq.), DMF (10 mL) and a stirbar. Excess methyl iodide (2.4 g, 16.8 mmol) was added and the reaction mixture stirred for 6 hours under ambient conditions. The mixture was then slowly added to stirred THF causing the polymer to precipitate as an off-white amorphous solid, which was dried under vacuum (2.3 g, 95%).

Using the above procedure, polymers P-2 and P-3 were also quaternized with methyl iodide (MeI) to form polymers Q-1 and Q-2, respectively. Table 9 summarizes the quaternary polymers formed.

TABLE 9

| Example | Name | Initial Polymer | DP (n) | MeI (equiv) | Quaternization (%) |
|---------|------|-----------------|--------|-------------|--------------------|
| 17 | Q-1 | P-2 | 50 | 2 | 99 |
| 18 | Q-2 | P-3 | 100 | 2 | 99 |
| 19 | Q-3 | P-4 | 200 | 2 | 99 |

Biological Measurements
Minimal Inhibitory Concentration (MIC)

Gram-positive *Staphylococcus aureus* (*S. aureus*, ATCC No. 29737), Gram-negative *Escherichia coli* (*E. coli*, ATCC No. 25922), Gram-negative *Pseudomonas aeruginosa* (*P. aeruginosa*, ATCC No. 9027), and *Candida albicans* (*C. albicans*, a fungus, (ATCC No. 10231) were re-constituted from the lyophilized form. Bacterial samples were cultured in tryptic soy broth (TSB) at 37° C. under constant shaking of 300 rpm. The MICs of the polymers were measured using the broth microdilution method. 100 microliters of tryptic soy broth (TSB) containing a polymer at various concentrations was placed into each well of a 96-well tissue culture plate. An equal volume of bacterial suspension ($3 \times 10^5$ CFU/ml), where CFU means colony forming units, was added into each well. Prior to mixing, the bacterial sample was first inoculated overnight to enter its log growth phase. The concentration of bacterial solution was adjusted to give an initial optical density (O.D.) reading of approximately 0.07 at 600 nm wavelength on microplate reader (TECAN, Switzerland), which corresponds to the concentration of McFarland 1 solution ($3 \times 10^8$ CFU/ml). The bacterial solution was further diluted by 1000 times to achieve an initial loading of $3 \times 10^5$ CFU/ml. The 96-well plate was kept in an incubator at 37° C. under constant shaking of 300 rpm for 18 hours. The MIC was taken as the concentration of the antimicrobial polymer at which no microbial growth was observed with unaided eyes and microplate reader (TECAN, Switzerland) at the end of 18 hours incubation. Broth containing microbial cells alone was used as negative control, and each test was carried out in 6 replicates.

Table 10 lists the MIC (mg/L), HC50 (mg/L), and HC selectivity values for the cationic polymers Q-1 to Q-3 (Examples 17-19) against *S. aureus, E. coli, P. aeruginosa*, and *C. albicans*.

TABLE 10

| Example | Name | DP (n) | MIC (mg/L) | | | | HC$_{50}$ | Hemolysis selectivity (HC$_{50}$/MIC) |
|---|---|---|---|---|---|---|---|---|
| | | | S. aureus | E. coli | P. aeruginosa | C. albicans | | |
| 12 | P-2 | 50 | >1000 | >1000 | >1000 | >1000 | >1000 | ND |
| 13 | P-3 | 100 | >1000 | >1000 | >1000 | >1000 | >1000 | ND |
| 14 | P-4 | 200 | >1000 | >1000 | >1000 | >1000 | >1000 | ND |
| 17 | Q-1 | 50 | 31 | 250 | 250 | 63 | >1000 | >4.0 to >32.3 |
| 18 | Q-2 | 100 | 31 | 63 | 250 | 63 | >1000 | >4.0 to >32.3 |
| 19 | Q-3 | 200 | 31 | 63 | 125 | 63 | >1000 | >8.0 to >32.3 |

ND = not determined

Lower MIC (500 mg/L or less) and higher HC50 (500 mg/L or more) represent preferred performance. An HC selectivity (HC50/MIC) value of 3 or more is also preferred. Each of the polymers was active against each of the four microbes, with Q-3 being the most active based on relative performance against *P. aeruginosa*.

Hemolytic Activity Testing of Cationic Polymers

Fresh rat blood cells were subjected to 25× dilution with phosphate buffered saline (PBS) to obtain an approximate 4% v/v suspension for use in this experiment. Red blood cell suspension (300 microliters) was added to each tube containing an equal volume (300 microliters) of polymer solution in PBS (with final polymer concentrations ranging from 3.9 mg/L to 1000 mg/L). The tubes were then incubated at 37° C. for 1 hour before they were centrifuged at 1000×g (g=relative centrifugal force) for 5 minutes. Aliquots (100 microliters) of supernatant were transferred to each well of a 96-well plate and analyzed for hemoglobin release at 576 nm using a microplate reader (TECAN, Switzerland). Red blood cells suspension incubated with PBS was used as negative control. Absorbance of red blood cells lyzed with 0.1% v/v Triton X-100 was used as the positive control and taken to be 100% hemolytic. Percentage of hemolysis was calculated using the following formula:

Hemolysis (%)=[(O.D.$_{576\ nm}$ of treated sample O.D.$_{576\ nm}$ of negative control)/(O.D.$_{576\ nm}$ of positive control O.D.$_{576\ nm}$ of negative control)]×100.

Data are expressed as mean±standard deviations of 4 replicates.

Figure 2:
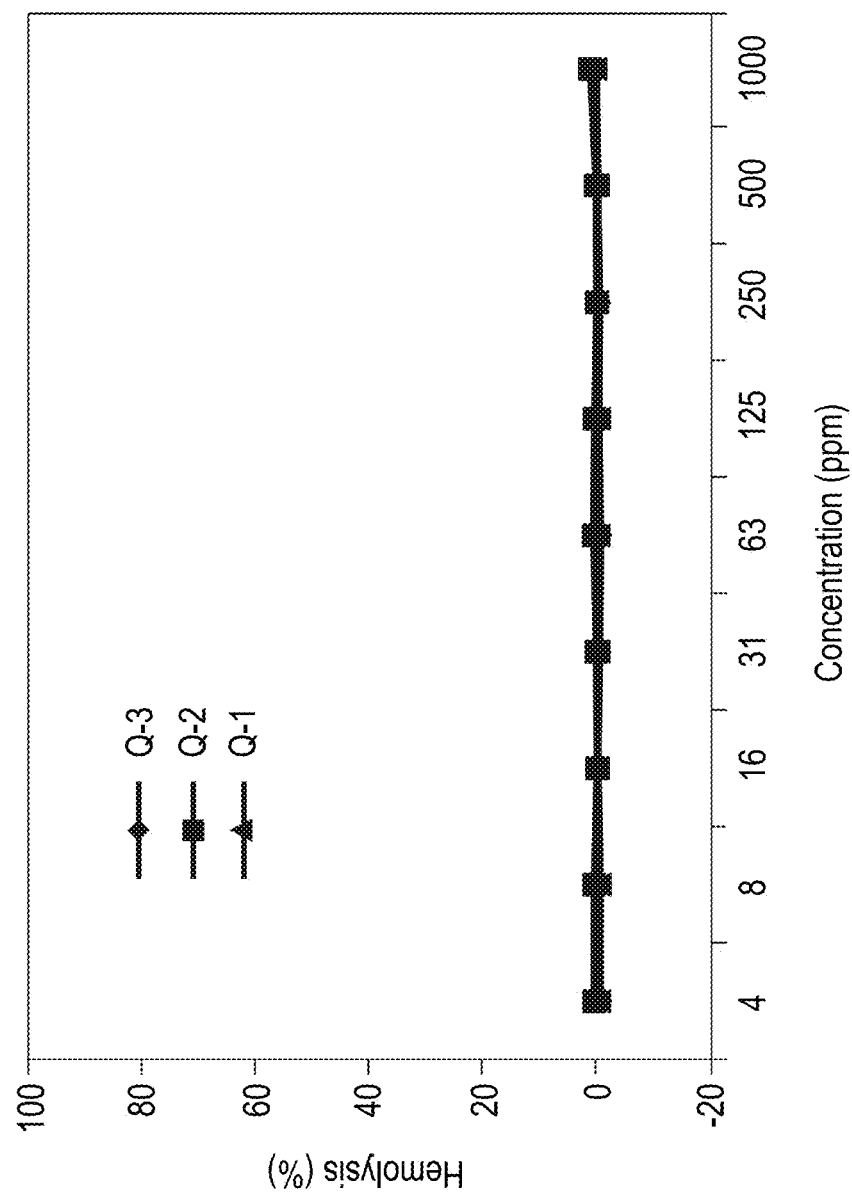
FIG. 2 is a graph showing the % hemolysis of rat red blood cells as a function of concentration (mg/L) of cationic polymer Examples 21 to 23 (Q-1 to Q-3).

FIG. 2 is a graph showing the % hemolysis of rat red blood cells as a function of concentration (mg/L) of cationic polymer Examples 21-23 (Q-1 to Q-3). About 0% hemolysis was observed for each of these polymers up to the highest concentration of 1000 ppm.

Cytotoxicity Testing of Cationic Polymers

Human dermal fibroblast (HDF) cells or human embryonic kidney (HEK293) cells were maintained in DMEM growth medium supplemented with 10% fetal bovine serum (FBS), sodium pyruvate, 100 U/mL penicillin and 100 mg/mL streptomycin and cultured at 37° C. under an atmosphere of 5% CO$_2$ and 95% humidified air. The cytotoxicity of polymers Q-1 to Q-3 against each cell line was studied using the standard 3-(4,5-dimethylthiazol-2-yl)-2,5-diphenyltetrazolium bromide (MTT) assay protocol. HDF cells (or HEK293) were seeded onto 96-well plates at a density of 1×10$^4$ cells per well and allowed to adhere overnight. The polymers were first dissolved in high pressure liquid chromatography (HPLC) grade water and serially diluted using Dulbecco's Modified Eagle Medium (DMEM) growth medium to achieve polymer concentrations ranging from 3.9 mg/L to 1000 mg/L with water concentration fixed at 10% v/v for each condition. Polymer solution (100 microliters) was added to the cells in each well, and the plate was allowed to incubate for 48 hours at 37° C. Subsequently, 100 microliters of growth media and 10 microliters of MTT solution (5 mg/ml in PBS) were added to each well and the cells were incubated for 4 hours at 37° C. according to the manufacturer's directions. Resultant formazan crystals formed in each well were solubilized using 150 microliters of dimethylsulfoxide (DMSO) upon removal of growth media, and the absorbance was determined using a microplate spectrophotometer at wavelengths of 550 nm and 690 nm. Relative cell viability was expressed as [(A$_{550}$−A$_{690}$)$_{sample}$/(A$_{550}$−A$_{690}$)$_{control}$]×100%. Data are expressed as mean±standard deviations of 3 to 4 replicates per polymer concentration.

Figure 3:
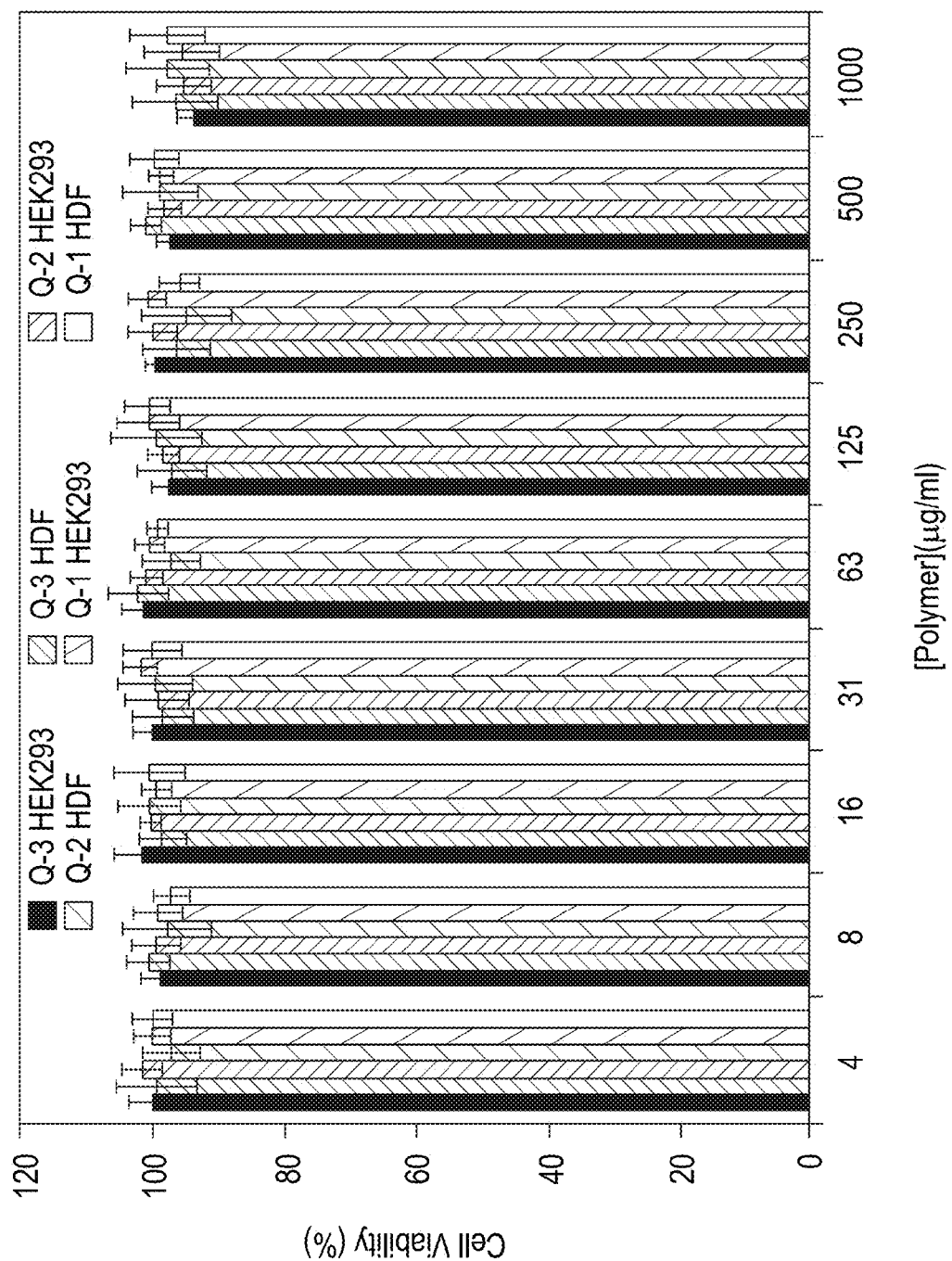
FIG. 3 is a bar graph showing the percent cell viability of HDF and HEK293 cells as a function of cationic polymer concentration.
Figure 4:
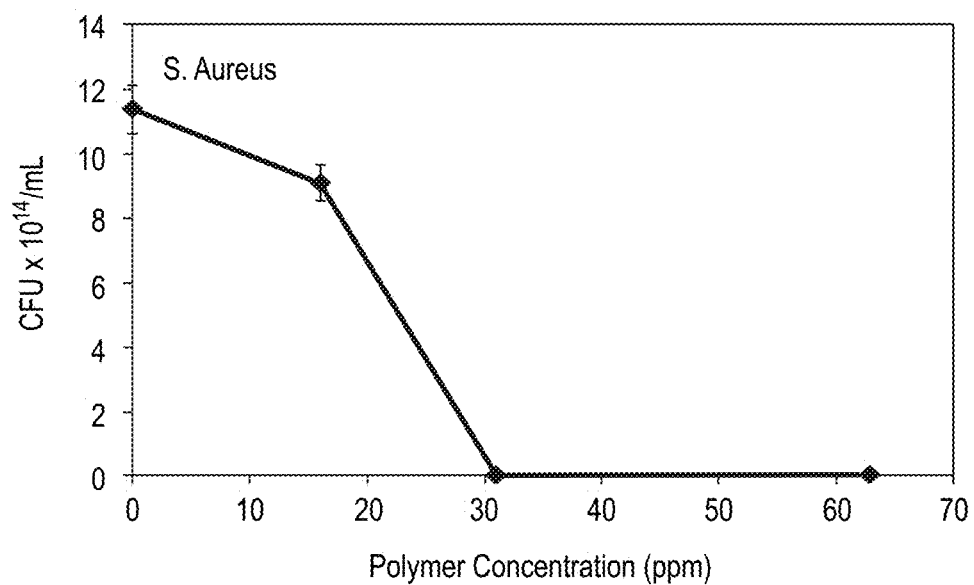
FIG. 4 is a graph showing colony forming units/mL of *Staphylococcus aureus* (*S. aureus*) as a function of Q-3 concentration.
Figure 5:
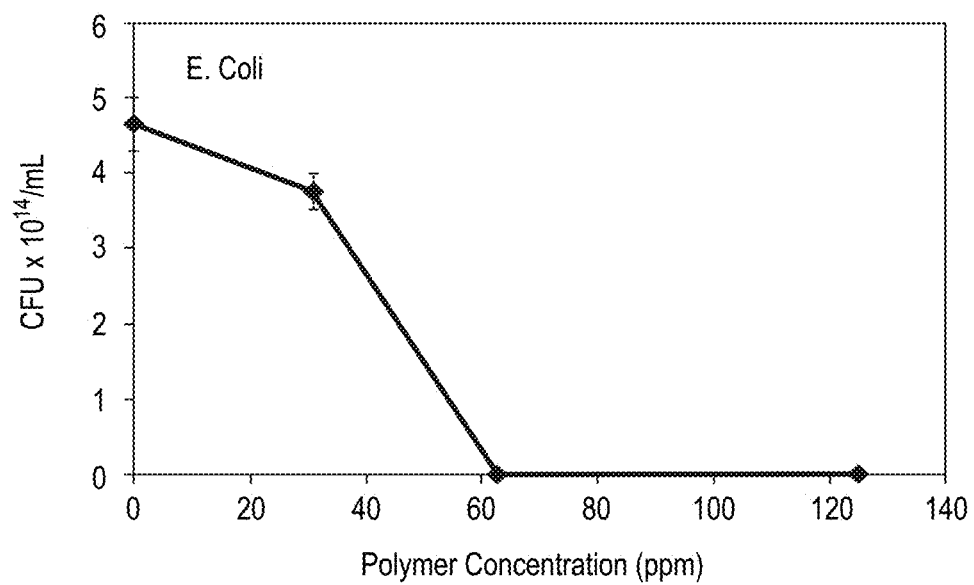
FIG. 5 is a graph showing colony forming units/mL of *Escherichia coli* (*E. coli*) as a function of Q-3 concentration.
Figure 6:
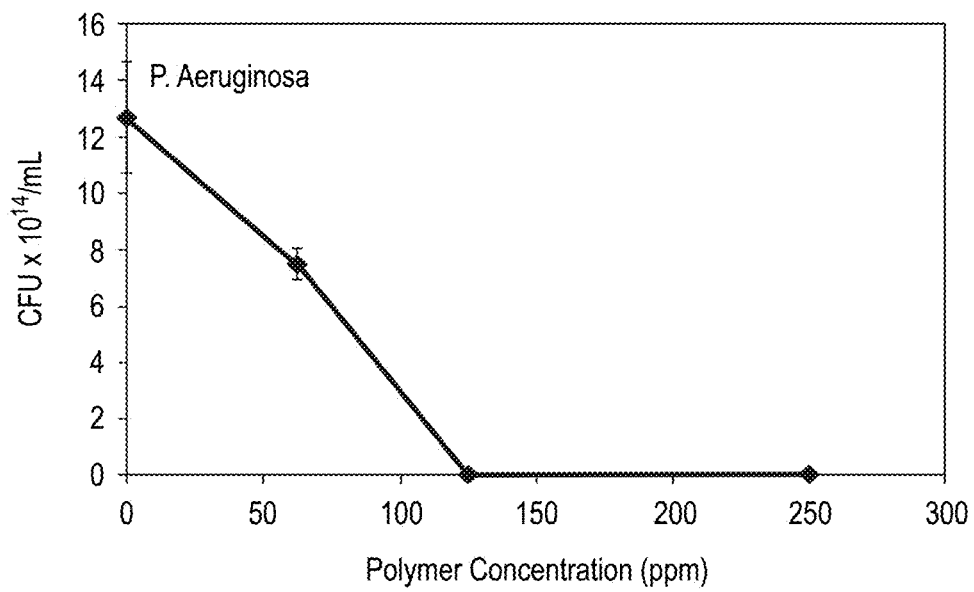
FIG. 6 is a graph showing colony forming units/mL of *Pseudomonas aeruginosa* (*P. aeruginosa*) as a function of Q-3 concentration.
Figure 7:
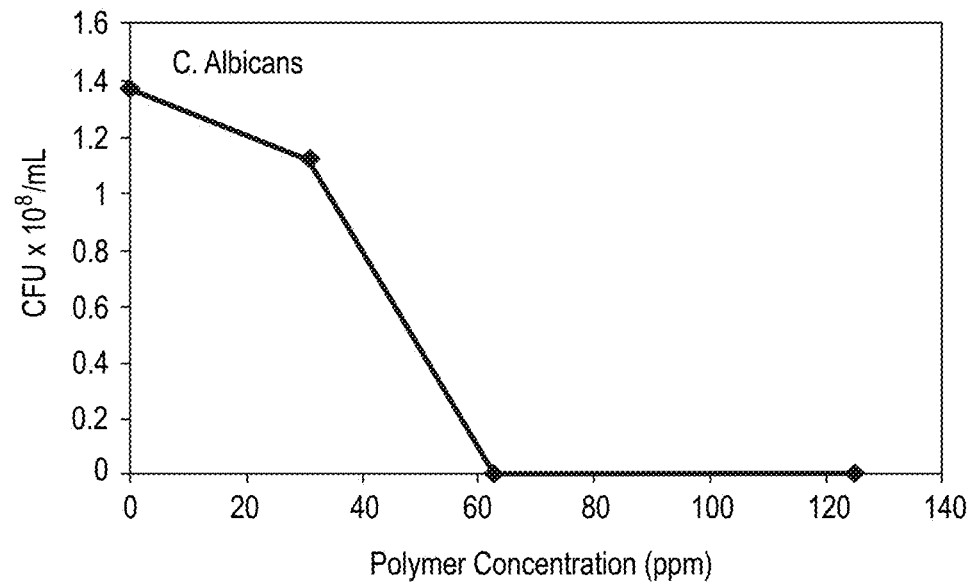
FIG. 7 is a graph showing colony forming units/mL of *Candida albicans* (*C. albicans*) as a function of Q-3 concentration.

FIG. 3 is a bar graph showing the percent cell viability of HDF and HEK293 cells as a function of cationic polymer concentration. Higher percent cell viability values are desirable at a given concentration. Each of Q-1 to Q-3 was non-toxic to both cell lines at all concentrations up to 1000 micrograms per milliliter.

Killing Efficiency of Cationic Polymers

Similar to MIC testing, 100 microliters of TSB containing a polymer at various concentrations (0, MIC and 2.0MIC) were placed into each well of a 96-well tissue culture plate. An equal volume of bacterial suspension (3×10$^5$ CFU/ml), where CFU means colony forming units, was added into each well. Prior to mixing, the bacterial sample was first inoculated overnight to enter its log growth phase. The concentration of bacterial solution was adjusted to give an initial optical density (O.D.) reading of approximately 0.07 at 600 nm wavelength on a microplate reader (TECAN, Switzerland), which corresponds to the concentration of McFarland 1 solution (3×10$^8$ CFU/ml). The bacterial solution was further diluted by 1000 times to achieve an initial loading of 3×10$^5$ CFU/ml. The 96-well plate was kept in an incubator at 37° C. under constant shaking of 300 rpm for 18 hours. The respective samples were then subjected to a series of ten-fold dilutions and plated onto lysogeny broth (LB) agar plates. The plates were then incubated overnight and counted for colony-forming units. A sample containing microbes treated with broth containing 10% v/v water was used as a control.

FIGS. 4 to 7 are graphs showing the relationship between colony forming units/mL of *S. aureus, E. coli, P. aeruginosa*, and *C. albicans* as a function of Q-3 concentration, respectively. For each microbe, the CFU count was zero at a cationic polymer concentration of 1×MIC. Thus, Q-3 achieved 99.999% killing efficiency at 1×MIC (i.e., the MBC is equal to the MIC).

Time-Kill Studies

Figure 8:
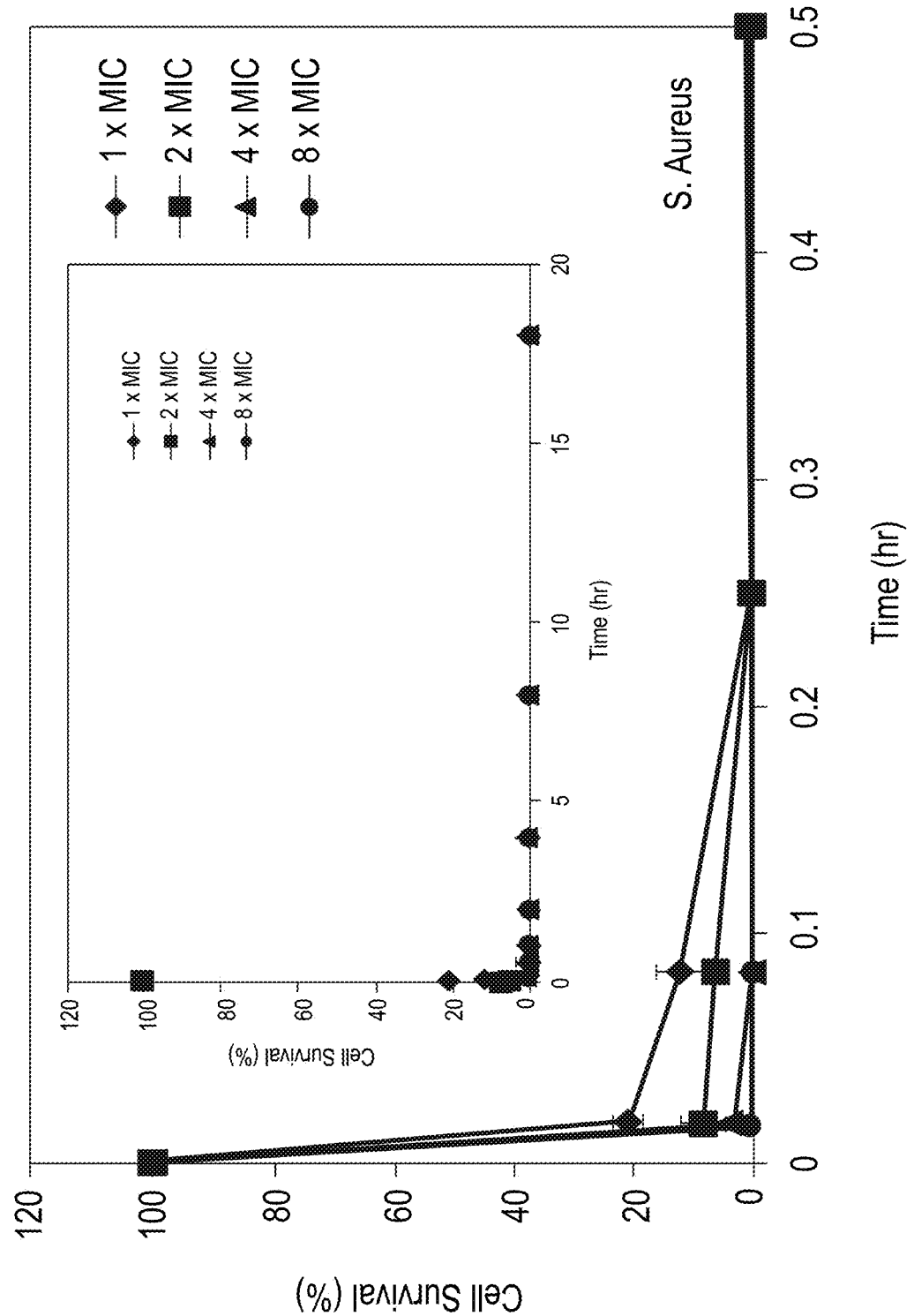
FIG. 8 is a bar graph showing the killing efficiency of Q-3 against *S. aureus*.
Figure 9:
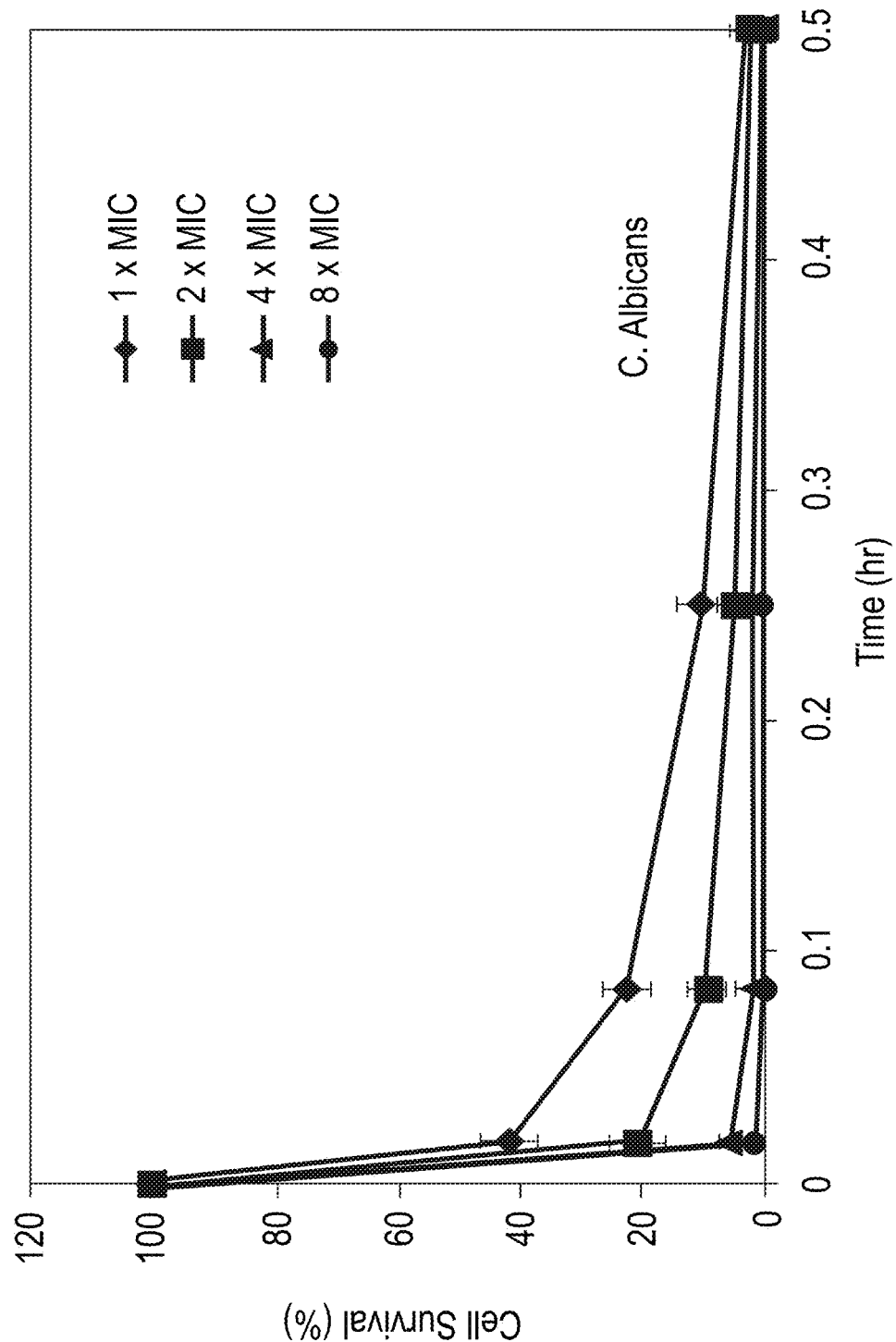
FIG. 9 is a bar graph showing the killing efficiency of Q-3 against *C. albicans*.
Figure 10:
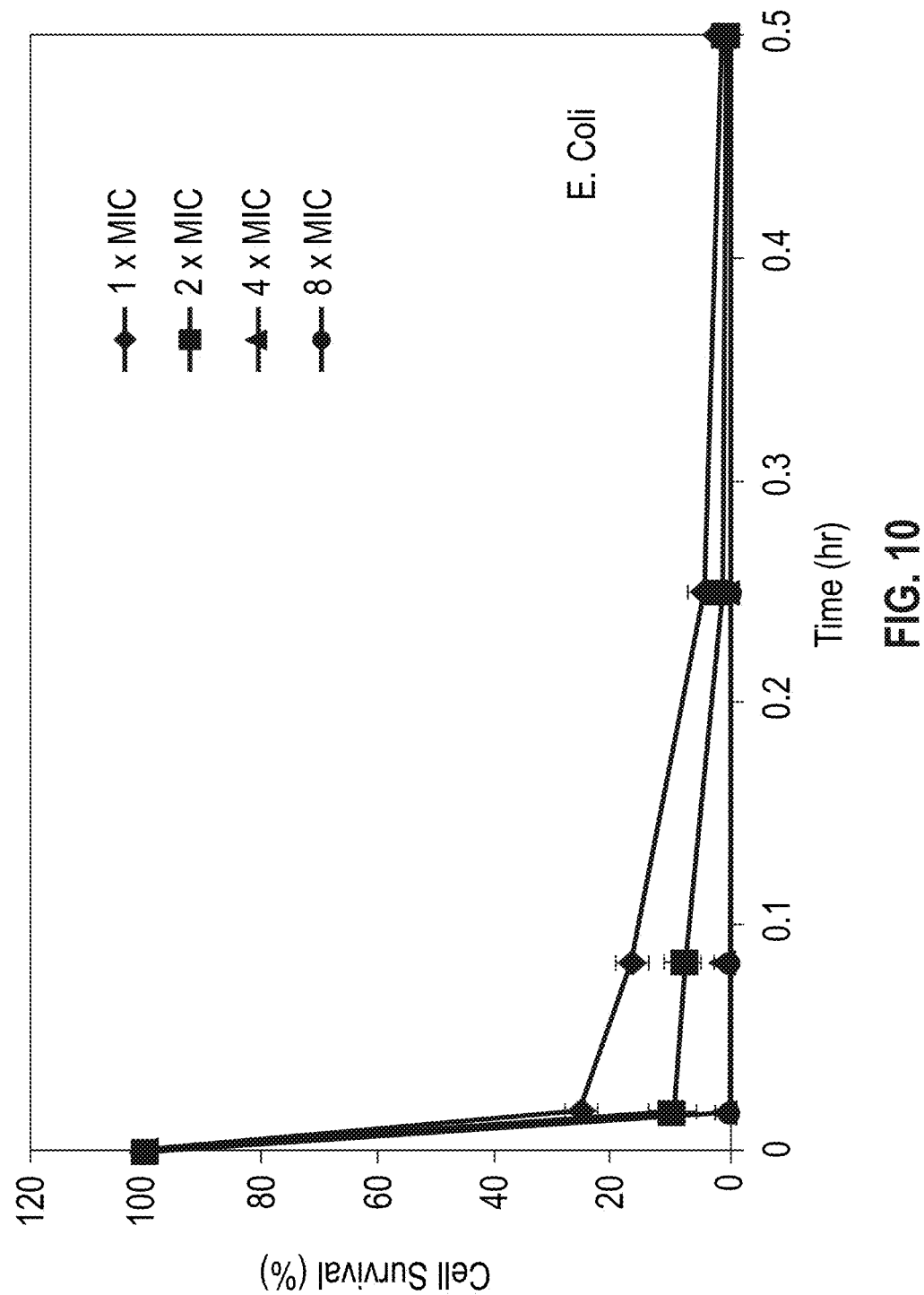
FIG. 10 is a bar graph showing the killing efficiency of Q-3 against *E. coli*.

*S. aureus, C. albicans*, and *E. coli* were treated with Q-3 at 1, 2, 4, and 8×MIC for up to 18 hours. The bar charts of FIGS. 8 to 10 show that Q-3 achieved 99.9% killing efficiency at 8×MIC and 1 minute. No growth was observed for *S. aureus* out to 18 hours (inset of FIG. 8).

Figure 11:
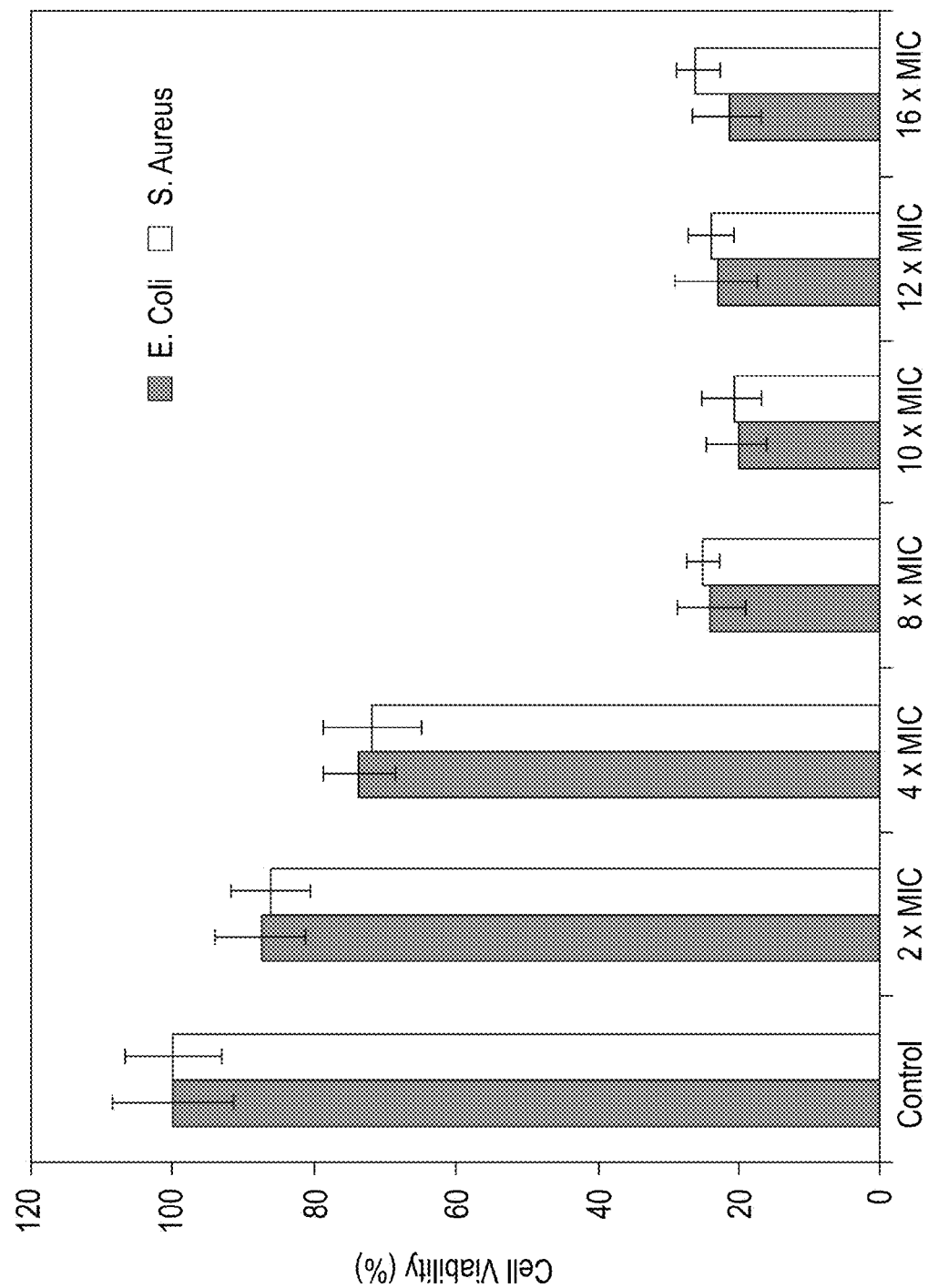
FIG. 11 is a bar graph showing the biomass of biofilms formed with *E. coli* and *S. aureus* as a function of Q-3 concentration (2, 4, 8, 10, 12, and 16xMIC).
Figure 12:
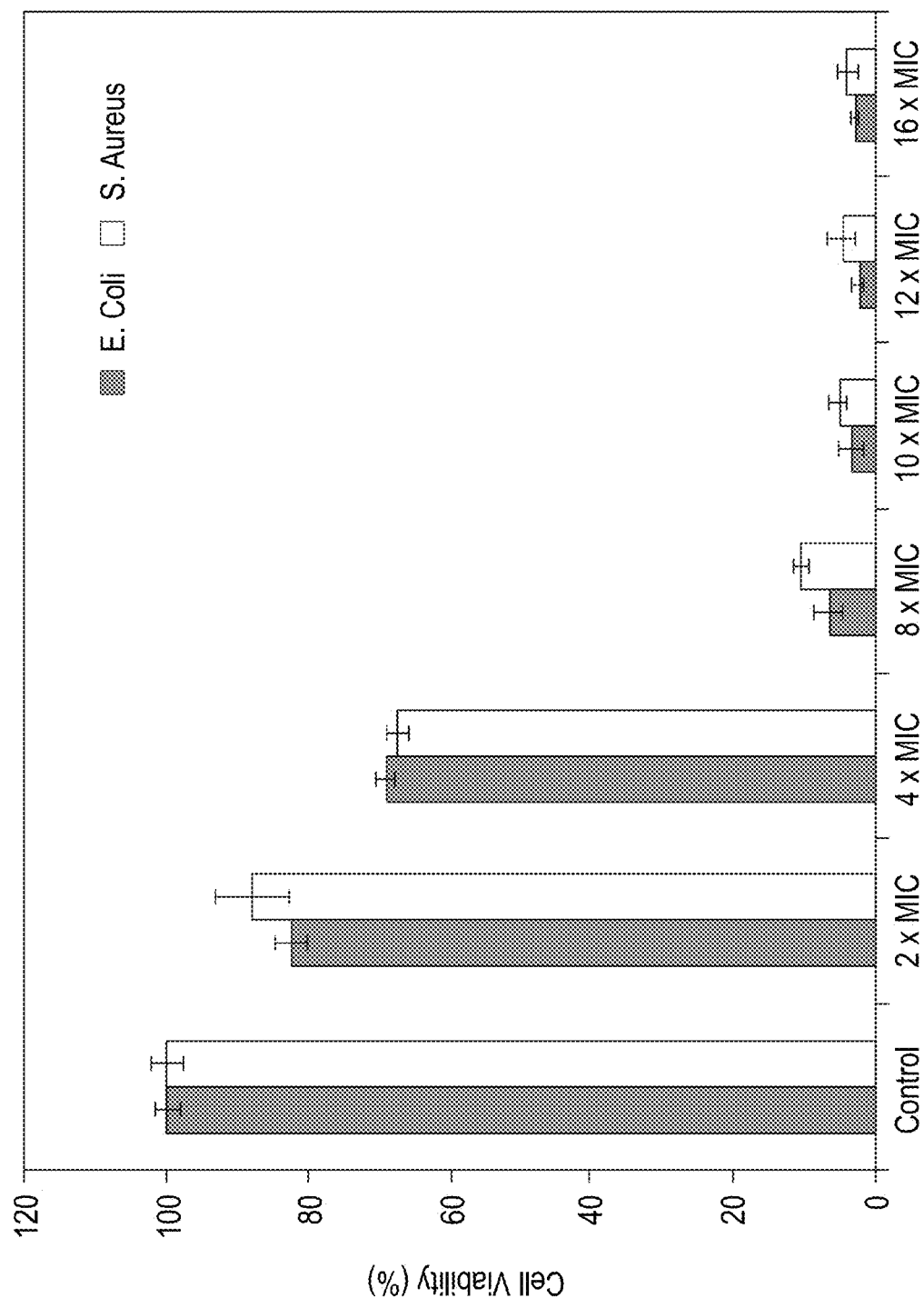
FIG. 12 is a bar graph showing the cell viability of *E. coli* and *S. aureus* as a function of Q-3 concentration (2, 4, 8, 10, 12, and 16xMIC).

FIG. 11 is a bar graph showing the biomass of biofilm of E. coli and S. aureus as a function of Q-3 concentration (2, 4, 8, 10, 12, and 16×MIC). The percent cell viability of E. coli and S. aureus at each concentration are plotted in FIG. 12 for comparison. Q-3 lysed S. aureus and E. coli biofilms effectively at 8×MIC after a single treatment.

Mechanism of Antimicrobial Properties

Figure 13:
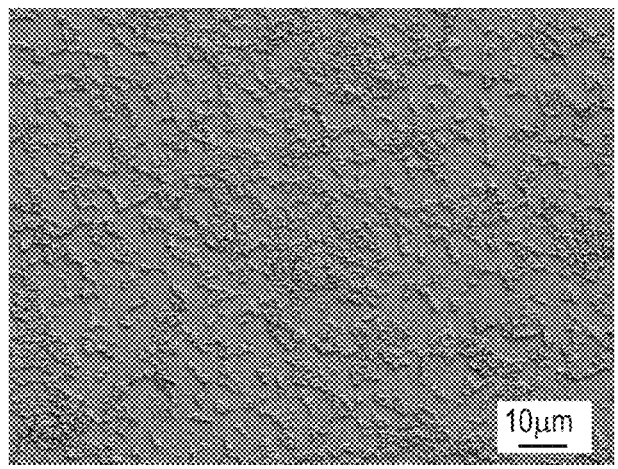
FIG. 13 is a magnification series of scanning electron micrograph (SEM) images of *S. aureus* cells after treatment for 2 hours with a lethal dose of Q-3.
Figure 13:
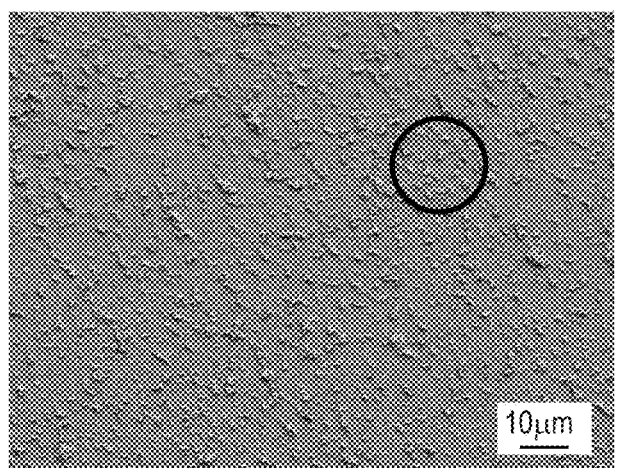
Figure 13:
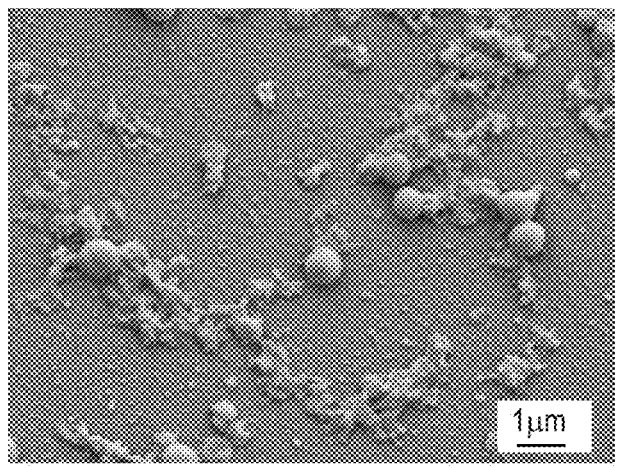
Figure 14:
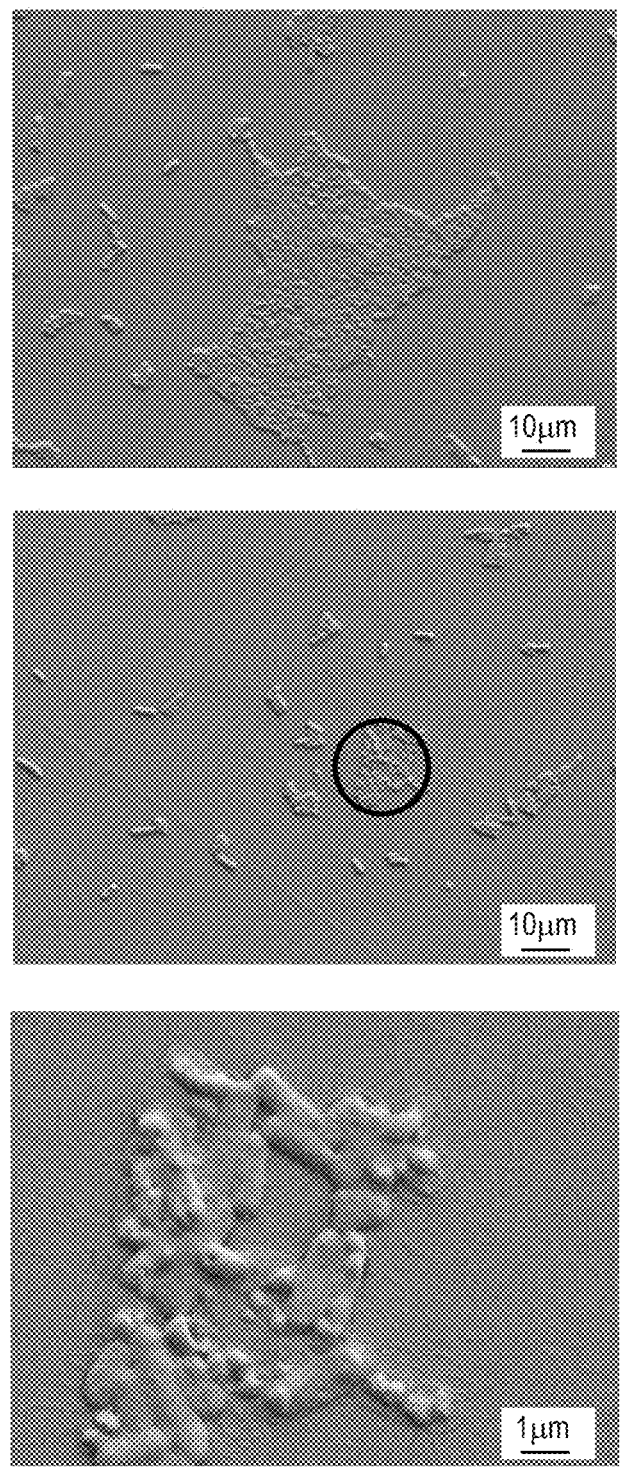
FIG. 14 is a magnification series of SEM images of *E. coli* cells after treatment for 2 hours with a lethal dose of Q-3.

The morphological changes of S. aureus and E. coli cells were observed by FE-SEM after treatment with the cationic polymer Q-3 for 2 hours. As can be seen in the magnification series of scanning electron microscope (SEM) images of FIG. 13, treatment of S. aureus with Q-3 at a lethal concentration (250 mg/L) for 2 hours results in significant membrane damage to S. aureus (right-most image). The SEM images of FIG. 14 show the treatment of E. coli with Q-3 at a lethal concentration (500 mg/L) for 2 hours also results in significant membrane damage to (right-most image). These results indicate that Q-3 interacts with the membrane of bacterial and yeast cells by forming pores and eventually leads to disruption of the bacterial and yeast membranes.

Conclusion

Biodegradable cationic polycarbonates having a main chain quaternary nitrogen were prepared and shown to be highly effective in killing Gram-positive and Gram-negative microbes. The cationic polymers are also effective in inhibiting or eradicating biofilms at low concentration. The cationic polymers can be non-hemolytic and non-cytotoxic.

Part II. Detailed Description

Further disclosed are cyclic carbonate monomers of formula (N-1), referred to below as "N-1 monomers":

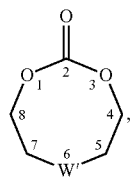
(N-1)

wherein

W' is a divalent radical selected from the group consisting of *—O—* and

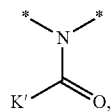

wherein K' is a monovalent radical selected from the group consisting of hydrogen, *—$R^1$, *—$OR^1$, and *—$NHR^1$, wherein $R^1$ is a $C_1$-$C_{10}$ monovalent hydrocarbyl group.

Non-limiting examples of $R^1$ include methyl, ethyl, n-propyl, iso-propyl, butyl, sec-butyl, t-butyl, phenyl, benzyl, and allyl. In an embodiment, $R^1$ is selected from the group consisting of t-butyl, ethyl, and allyl.

Non limiting examples of K' groups include methyl, ethyl, n-propyl, iso-propyl, n-butyl, sec-butyl, t-butyl, phenyl, benzyl, allyl, methoxy, ethoxy, n-propyloxy, iso-propyloxy, n-butoxy, sec-butoxy, t-butoxy, phenoxy, benzoxy, allyloxy, methylamino, ethylamino, n-propylamino, iso-propylamino, n-butylamino, sec-butylamino, t-butylamino, phenylamino, benzylamino, and allyl amino. In an embodiment, K' is selected from the group consisting of t-butoxy, ethoxy, and allyloxy.

It should be understood that the oxygen of *—O—* and the nitrogen of

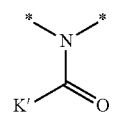

are bonded to carbons 5 and 7 of the ring in formula (N-1).

Non-limiting examples of N-1 monomers include those of Scheme 2.

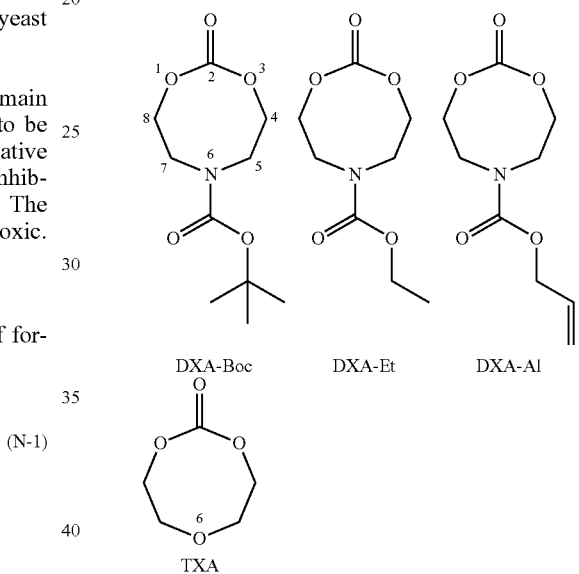

Scheme 2.

DXA-Boc    DXA-Et    DXA-Al

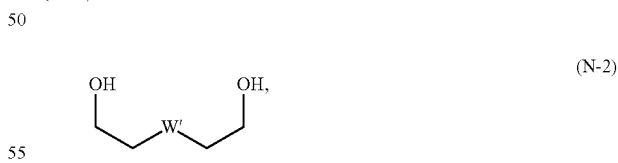

TXA

The ring positions are numbered 1-8 in DXA-Boc. Position 6 is occupied by the nitrogen, ether oxygen, and sulfur of the ring.

The N-1 monomers can be prepared from diols of formula (N-2):

OH    OH, (N-2)

W' wherein

W' is a divalent radical selected from the group consisting of *—O—* and

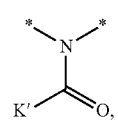

wherein K' is a monovalent radical selected from the group consisting of hydrogen, *—R$^1$, *—OR$^1$, and *—NHR$^1$, wherein R$^1$ is a C$_1$-C$_{10}$ monovalent hydrocarbyl group.

The N-1 monomers can be prepared by treating a diol of formula (N-2) with ethyl chloroformate, a base catalyst (e.g., triethylamine), and a solvent using the procedures described in the Examples section further below.

The N-1 monomers can undergo an organocatalyzed ring opening polymerization (ROP) to form a polycarbonate. A method comprises forming a mixture comprising an organocatalyst, a solvent, a nucleophilic initiator comprising one or more nucleophilic groups capable of initiating a ring opening polymerization, an optional accelerator, and a monomer of formula (N-1). Agitating the mixture produces an initial polymer by ring opening polymerization of the compound. In an embodiment, the monomer is selected from the group consisting of

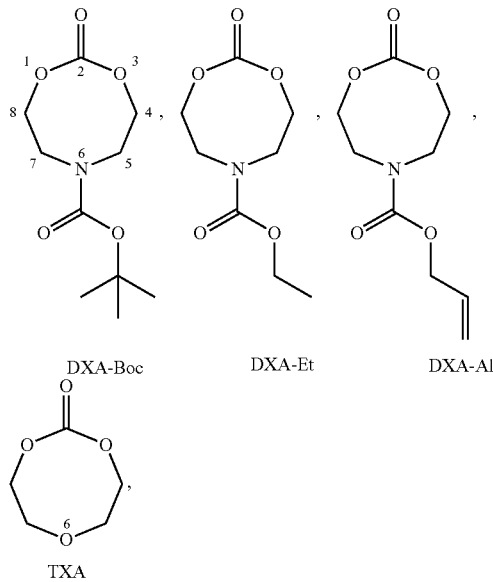

DXA-Boc    DXA-Et    DXA-Al

TXA and combinations thereof.

The initial polymer (polycarbonate) comprises a carbonate repeat unit of formula (N-3), also referred below to as an "N-3 repeat unit":

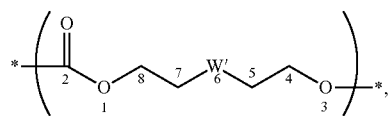 (N-3)

wherein

W' is a divalent radical selected from the group consisting of *—O—* and

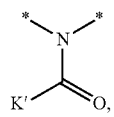

wherein K' is a monovalent radical selected from the group consisting of hydrogen, *—R$^1$, *—OR$^1$, and *—NHR$^1$, wherein R$^1$ is a C$_1$-C$_{10}$ monovalent hydrocarbyl group.

Non-limiting examples of N-3 repeat units include those of Scheme 3.

Scheme 3.

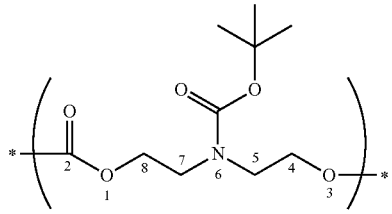

RU-1

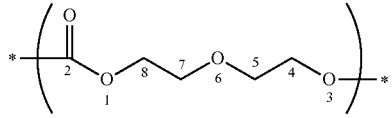

RU-2

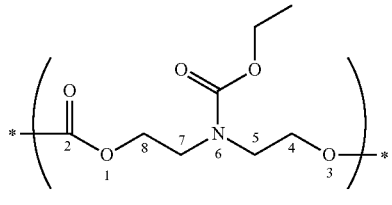

RU-3

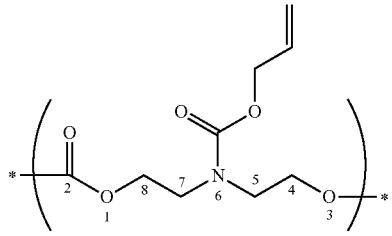

RU-5

The N-1 monomers can be used singularly or in combination in the polymerization. The ROP can include other cyclic carbonyl monomers, including cyclic carbonates and/or cyclic esters described further above, which can serve as diluents (comonomers) for the N-1 monomers.

More specific initial polymers formed with N-1 monomers can have a structure according to formula (N-4):

$$I^1 \!-\!\![\!-\!P^1\!-\!E^1]_{n'} \quad (N\text{-}4),$$

wherein
n' is a positive integer greater than or equal to 1,
each P$^1$ is a polymer chain comprising an N-3 repeat unit,
I$^1$ is a radical having a valency of n', wherein I$^1$ comprises 1 or more carbons,
a terminal backbone carbonyl group of each P$^1$ is linked to a respective independent heteroatom of I$^1$ selected from the group consisting of oxygen, nitrogen, and sulfur;
each E$^1$ is a monovalent end group selected from the group consisting of hydrogen and moieties comprising 1 to 50 carbons, and
a terminal backbone oxygen of each P$^1$ is linked to a respective E$^1$.

I$^1$ can be a residue of a nucleophilic initiator for an organocatalyzed ROP of the N-1 monomers. The nucleophilic initiator comprises n' nucleophilic sites capable of initiating the ROP, and n' polymer chains P$^1$ are formed by the ROP.

Each $P^1$ can be a homopolymer, random copolymer, or block copolymer comprising an N-3 repeat unit of formula (N-3). Each $P^1$ can have an average degree of polymerization (DP) of between 1 and about 200. In an embodiment, n'=1 and the initial polymer comprises one polymer chain $P^1$ having an average DP of about 20 to about 100.

The initial polymer can comprise N-3 repeat units singularly or in combination. $P^1$ can further comprise repeat units derived from cyclic carbonate and/or cyclic ester monomers described further above.

Each $P^1$ preferably has a linear arrangement of repeat units (i.e., each $P^1$ is a linear polymer chain comprising one polymer branch as opposed to intersecting polymer branches). When $P^1$ contains two or more polymer chain segments (e.g., as a diblock copolymer chain), the different chain segments are linked by their respective chain ends, no more than two polymer chain ends are linked together by a given linking group, and the respective polymer chain segments are not linked together in the form of a cyclic polymer structure.

$I^1$ can be a residue of a nucleophilic initiator an organocatalyzed ring opening polymerization used to form P', or $I^1$ can be a derivative of the residue of the nucleophilic initiator. Preferably, $I^1$ comprises n' number of independent heteroatoms selected from the group consisting of oxygen, nitrogen, and sulfur, wherein each of the heteroatoms is linked in the form of a carbonate, carbamate or thiocarbonate group to a respective $P^1$ terminal backbone carbonyl group (i.e., to the "carbonyl end" of $P^1$).

$I^1$ can comprise a biologically active moiety such as, for example, a steroid group and/or a vitamin. $I^1$ can comprise a polymer such as, for example a poly(ethylene oxide) chain segment. In an embodiment, $I^1$ is a residue of a mono-endcapped mono-nucleophilic polyethylene oxide initiator (e.g., mono-methylated polyethylene glycol (mPEG)). In another embodiment, $I^1$ comprises 1 to 50 carbons. In yet another embodiment, $I^1$ is an alkoxy or aryloxy group comprising 1 to 10 carbons.

Each $E^1$ is preferably linked to a terminal backbone oxygen at the opposing end of a respective polymer chain $P^1$, referred to herein as the "oxy end" of $P^1$. When $E^1$ is hydrogen, $P^1$ has a terminal hydroxy group (i.e., a living chain end capable of initiating another ring opening polymerization). When $E^1$ is not hydrogen, $E^1$ can be any suitable end group comprising 1 to 50 carbons. In an embodiment, $E^1$ is an acyl group comprising 1 to 15 carbons (e.g., acetyl group).

In an embodiment, n'=1. A non-limiting example of an initial polymer of formula (N-4) wherein n'=1 is the polycarbonate N-5:

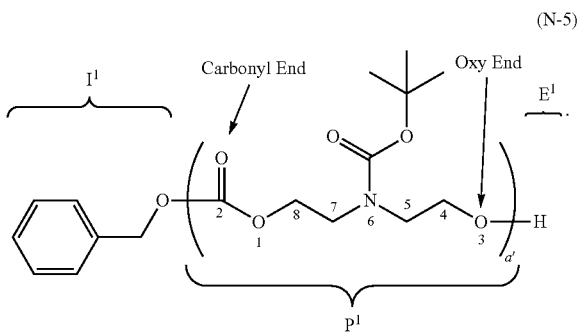

(N-5)

In this example, initial polymer N-5 has one polymer chain $P^1$ that has one polymer chain segment. $P^1$ of N-5 is a polycarbonate homopolymer of the carbonate repeat unit RU-1. That is, the carbonate repeat unit of N-5 has a structure according to formula (N-3) wherein each W' is

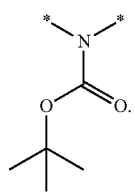

N-5 is a linear polymer in which the carbonate repeat units are linked in a head-to-tail arrangement. Carbon 2 represents the head, and oxygen 3 represents the tail of a given repeat unit. Polymer chain $P^1$ of N-5 has two polymer chain ends linked to respective end groups $I^1$ and $E^1$. The carbonyl end and oxy end of $P^1$ are indicated by arrows. (i.e., nitrogen 6 is linked to a Boc protecting group). The first end group $I^1$ is benzyloxy, and the second end group $E^1$ is hydrogen. Subscript a' represents the degree of polymerization, and has an average value of 2 to 200. N-5 has a living end containing a primary alcohol, which can potentially initiate a ring opening polymerization.

Another more specific initial polymer prepared with N-1 monomers comprises two polymer chains (n'=2 in formula (N-4)). In this instance, the initial polymer can have a structure in accordance with formula (N-6):

$$E^2-P^2-I^2-P^3-E^3 \qquad (N-6),$$

wherein $P^2$ is a first divalent polymer chain comprising one or more polymer chain segments, wherein at least one of the polymer chain segments comprises an N-3 repeat unit, $P^3$ is a second divalent polymer chain comprising one or more polymer chain segments, wherein at least one of the polymer chain segments comprises an N-3 repeat unit, $I^2$ is a divalent linking group covalently bound to the respective carbonyl ends of $P^2$ and $P^3$, $E^2$ is a monovalent first end group selected from the group consisting of hydrogen and moieties comprising 1 to 50 carbons, wherein $E^a$ is linked to the oxy end of $P^a$, and $E^3$ is a monovalent second end group selected from the group consisting of hydrogen and moieties comprising 1 to 50 carbons, wherein $E^3$ is linked to the oxy end of $P^b$.

$P^2$ can have an average degree of polymerization of more than 1 to about 200. $P^2$ can be a homopolymer, random copolymer, or block copolymer comprising an N-3 repeat unit.

$P^3$ can have an average degree of polymerization of more than 1 to about 200. $P^3$ can be a homopolymer, random copolymer, or block copolymer comprising an N-3 repeat unit.

In an embodiment, $I^2$ is a residue of a di-nucleophilic initiator for the organocatalyzed ring opening polymerization used to prepare $E^2$-$P^2$—$I^2$—$P^3$-$E^3$. In this instance, $I^2$ comprises two heteroatoms independently selected from oxygen, nitrogen, and sulfur, wherein the two heteroatoms are independently linked in the form of carbonate, carbamate, or thiocarbonate groups to respective carbonyl ends of $P^2$ and $P^3$. $I^2$ can be a derivative of the residue of the di-nucleophilic initiator for the ROP.

$I^2$ can comprise a polymer such as, for example, a divalent poly(ethylene oxide) chain. $I^2$ can comprise a biologically active group such as a steroid and/or a vitamin. In an embodiment, $I^2$ is a residue of a di-nucleophilic polyethylene glycol initiator for the ROP. In another embodiment, $I^2$ comprises 1 to 50 carbons. In another embodiment, $I^2$ is a residue of an ester of 2,2-dimethylol propionic acid (bis-MPA), which have the formula (N-7):

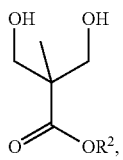
(N-7)

wherein $R^2$ is a group comprising 1 to 45 carbons. Non-limiting exemplary $R^2$ groups include hydrocarbyl groups (e.g., methyl, ethyl, iso-propyl, n-butyl, t-butyl, phenyl, benzyl, 4-methyl benzyl, and the like). Other $R^2$ groups include biologically active groups such as steroid groups (e.g., cholesteryl) and vitamin groups.

$E^2$ is linked to the oxy end of $P^2$. When $E^2$ is hydrogen, $P^2$ has a terminal hydroxy group (i.e., a living chain end potentially capable of initiating another ring opening polymerization). When $E^2$ is not hydrogen, $E^2$ can be any suitable end group comprising 1 to 50 carbons. In an embodiment, $E^2$ is an acyl group comprising 1 to 10 carbons (e.g., acetyl).

$E^3$ is linked to the oxy end of $P^3$. When $E^3$ is hydrogen, $P^3$ has a terminal hydroxy group (i.e., a living chain end potentially capable of initiating another ring opening polymerization). When $E^3$ is not hydrogen, $E^3$ can be any suitable end group comprising 1 to 50 carbons. In an embodiment, $E^3$ is an acyl group comprising 1 to 10 carbons (e.g., acetyl).

$E^2$ and $E^3$ can comprise an above-described biologically active moiety.

A non-limiting example of an initial polymer of formula (N-6) is polycarbonate N-8:

The initial polymer N-8 is a linear polymer containing two polymer chains linked by respective chain ends to divalent linking group $I^2$. Each polymer chain $P^2$ and $P^3$ of N-8 is a polycarbonate homopolymer of the carbonate repeat unit RU-1. That is, the carbonate repeat unit of each polymer chain of N-8 has a structure according to formula (N-3) wherein each W' is

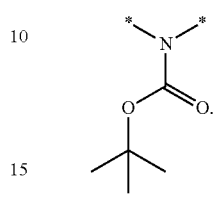

The carbonyl ends and oxy ends of each polymer chain $P^2$ and $P^3$ are labeled in N-8. In this example, $I^2$ is benzyl 2,2-bis(oxymethylene)propionate, $E^2$ is hydrogen, and $E^3$ is hydrogen. Subscripts a' and b' represent degree of polymerization and independently have average values of more than 1 to about 200. The initial polymer N-8 has two living ends containing primary alcohols, each potentially capable of initiating a ring opening polymerization.

The initial polymers can be stereospecific or non-stereospecific.

Cationic Polymers

When treated with a suitable acid, an initial polymer comprising the N-Boc repeat unit

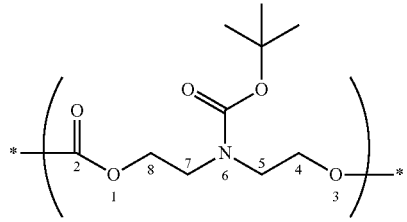

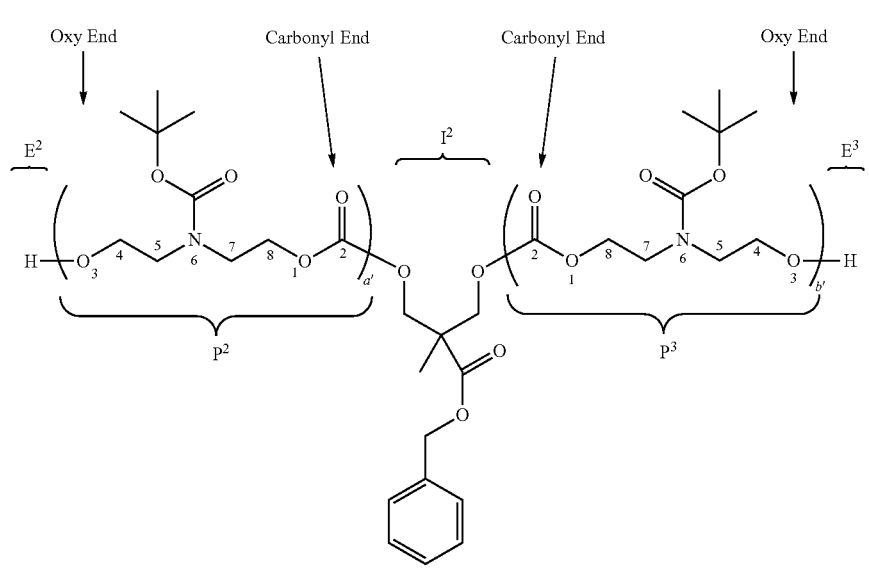
(N-8)

is converted to a cationic polymer comprising an ammonium repeat unit of formula (N-9):

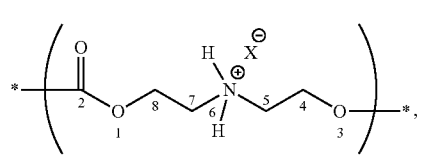

wherein $X^{\ominus}$ is a negative-charged counterion. The positive-charged nitrogen of formula (N-9) is a secondary ammonium nitrogen bonded to two carbons and two hydrogens, and ionically associated with $X^{\ominus}$. $X^{\ominus}$ can be any suitable negative-charged counterion. $X^{\ominus}$ counterions can be presented singularly or in combination. In an embodiment, the acid used to deprotect the N-Boc nitrogen is trifluoroacetic acid, and $X^{\ominus}$ is trifluoroacetate.

As a non-limiting example, treating polymer N-5 with trifluoroacetic acid can provide polymer N-10:

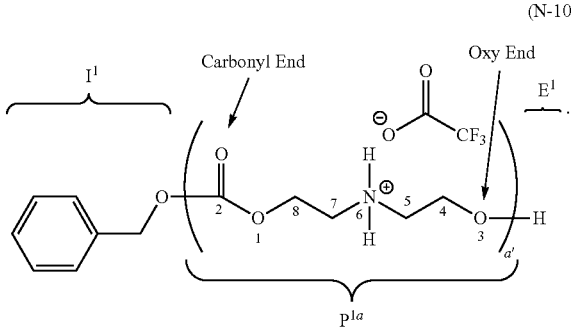

Polymer N-10 has one polymer chain $P^{1a}$ comprising one polymer chain segment. In this example, $P^{1a}$ is a polycarbonate homopolymer of the cationic repeat unit shown in parentheses. N-10 has a linear polymer structure. Polymer chain $P^{1a}$ has two polymer chain ends linked to respective end groups $I^1$ and $E^1$. The carbonyl end and oxy end of $P^{1a}$ are indicated by arrows. The first end group $I^1$ is benzyloxy, and the second end group $E^1$ is hydrogen. Subscript a' represents the degree of polymerization and has an average value of more than one to about 200. N-10 has a living end containing a primary alcohol, which can potentially initiate a ring opening polymerization.

As another non-limiting example, treating the polymer N-8 with trifluoroacetic acid can provide cationic polymer N-11:

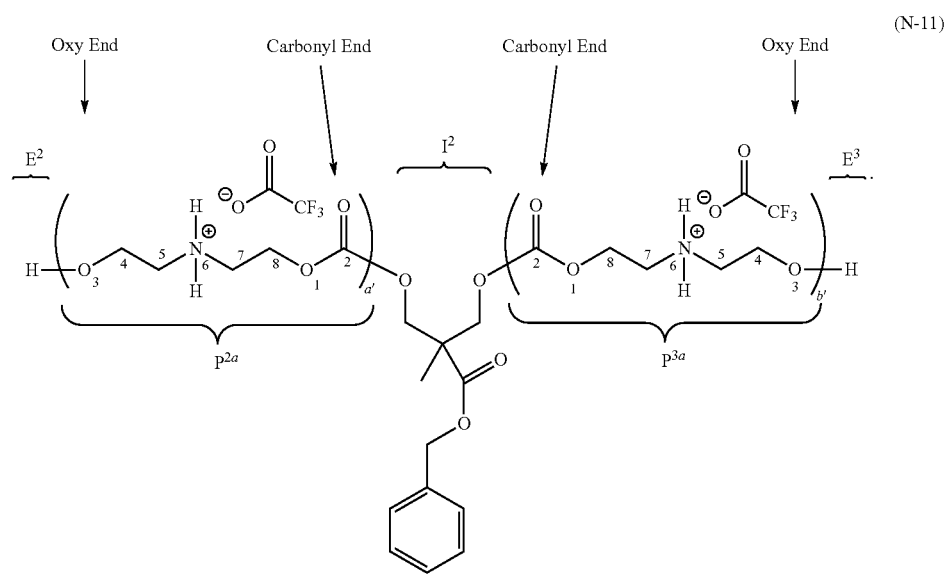

The cationic polymer N-11 is a linear polymer containing two polycarbonate chains $P^{2a}$ and $P^{3a}$ linked by respective carbonyl ends to divalent linking group $I^2$. Each of polymer chains $P^{2a}$ and $P^{3a}$ is a homopolymer of the secondary ammonium cationic repeat unit shown in parentheses. The carbonyl ends and oxy ends of $P^{2a}$ and $P^{3a}$ are labeled in N-11. In this example, $I^2$ is benzyl 2,2-bis(oxymethylene) propionate, and end groups $E^2$ and $E^3$ are hydrogen. Subscripts a' and b' represent degree of polymerization and have average values of more than 1 to about 200. The cationic polymer N-11 has two living ends containing primary alcohol groups, which are potentially capable of initiating a ring opening polymerization.

The cationic polymers can be stereospecific or non-stereospecific.

Repeat unit RU-1 introduces a backbone secondary amine group into the aliphatic polycarbonate, which increases hydrophilicity and buffering capability of the polymer while retaining biodegradability.

Repeat unit RU-2 increases backbone hydrophilicity compared to previous non-charged aliphatic polycarbonates (e.g., poly(trimethylene carbonate)) without introducing a charged group. Biodegradability is also preserved.

The ring opening polymers (ROP) of N-1 monomers can have narrow molecular weight distributions (1.1 PDI). As with previously reported cyclic carbonates these monomers are readily polymerized using organocatalysis allowing complete catalyst removal. The nitrogen heteroatom at the 6 position allows for a wide range of additional functionality.

Also disclosed are more specific compounds of formula (1) (see Part I), having a structure of formula (N-12):

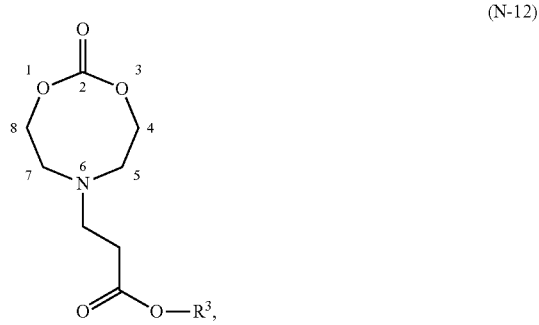

(N-12)

wherein R³ is a hydrocarbyl group comprising 1 to 10 carbons. In an embodiment, R³ is selected from the group consisting of methyl, ethyl, n-propyl, iso-propyl, butyl, sec-butyl, t-butyl, phenyl, benzyl, and allyl.

Compounds of formula (N-12) can be prepared by Michael addition of diethanolamine to an acrylate ester using known techniques, followed by ring closure of the Michael adduct using ethyl chloroformate as described below.

More specific compounds of formula (N-12) include DXA-tBuP and DXA-MeP.

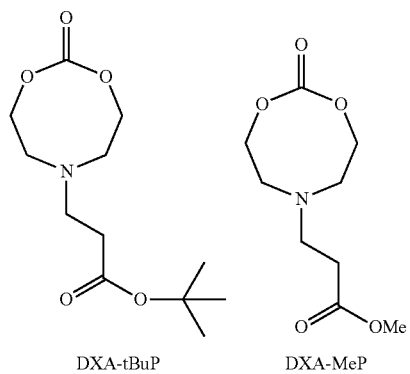 [SMILES: CC(C)(C)OC(=O)CCN1CCOC(=O)OCC1 ; COC(=O)CCN1CCOC(=O)OCC1]

DXA-tBuP    DXA-MeP

Compounds of formula (N-12) are cyclic carbonate monomers that undergo ring opening polymerization to form polymers (e.g., polycarbonates) having a carbonate repeat unit of formula (N-13):

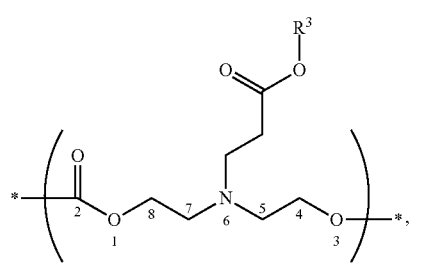

(N-13)

wherein R³ is a hydrocarbyl group comprising 1 to 10 carbons. In an embodiment, R³ is selected from the group consisting of methyl, ethyl, n-propyl, iso-propyl, butyl, sec-butyl, t-butyl, phenyl, benzyl, and allyl. The tertiary amine nitrogen at position labeled 6 is covalently bonded to 3 carbons. The tertiary amine nitrogen is an atom of the polymer backbone.

The following examples demonstrate preparations of N-1 and N-12 monomers, and polymers formed therefrom. The examples also include preparations of DXA-tBuP and DXA-MeP, and ring opened polymers therefrom.

EXAMPLES

N-bis(3,5-trifluoromethyl)phenyl-N'-cyclohexyl-thiourea (TU) has the following structure:

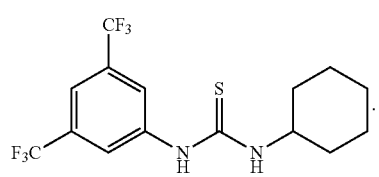

(TU)

TU was prepared as reported by the method of R. C. Pratt, B. G. G. Lohmeijer, D. A. Long, P. N. P. Lundberg, A. Dove, H. Li, C. G. Wade, R. M. Waymouth, and J. L. Hedrick, Macromolecules, 2006, 39 (23), 7863-7871, and dried by stirring in dry THF over CaH₂, filtering, and removing solvent under vacuum. Benzyl alcohol and 1,8-diazabicyclo [5.4.0]undec-7-ene (DBU) were distilled twice from CaH₂ under dry N₂ and stored in the glove box. The macroinitiator, mPEG-OH (~5.0 kDa, lot #1211.265, PDI=1.02) was purchased from RAAP Polymere GmbH (Tuebingen, Germany). 1,5,7-Triazabicyclo[4.4.0]dec-5-ene (TBD) was purchased from Sigma Aldrich. All monomers and reagents were dried extensively by freeze drying process under high vacuum prior to transfer into the glove box.

The following diols used in the preparations below were commercially available (DEA-Boc, Sigma Aldrich) or readily synthesized by reaction of diethanolamine with a suitable acylating agent (ADC and EDC), or by Michael-addition of diethanolamine (DEA) to a corresponding acrylate ester (MDP and tBuDP). The Michael addition reactions are detailed below.

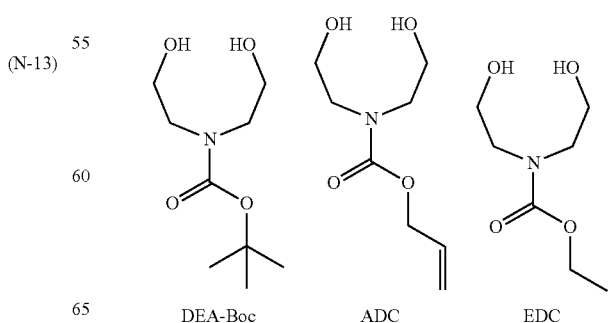

DEA-Boc    ADC    EDC

-continued

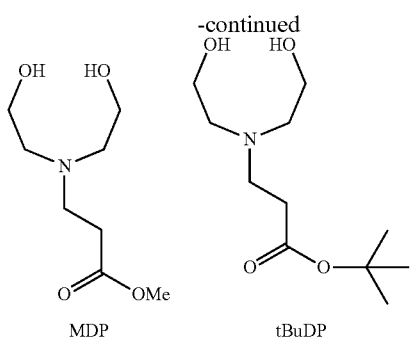

MDP    tBuDP

Example 20. Preparation of Diol MDP

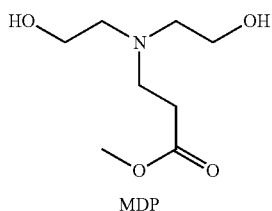

MDP

To a 100 mL round bottom flask containing diethanolamine (DEA, 10.1 g, 96.0 mmol, 1.0 equiv.) and magnetic stir bar, methyl acrylate (35.3 g, 0.41 mol, 4.3 equiv.) was added in one portion and the reaction mixture was allowed to stir at room temperature overnight (about 16 hours). Excess methyl acrylate was removed in vacuo to yield the target diol as colorless viscous oil (18.3 g, ~100%). $^1$H NMR (400 MHz, CDCl$_3$, ppm): delta 3.69 (s, CH$_3$, 3H), 3.60 (t, J=5.2 Hz, —CH$_2$OH, 4H), 3.0 (br. s, —OH, 2H), 2.83 (t, J=6.4 Hz, —CH$_2$COOCH$_3$, 2H), 2.63 (t, J=5.2 Hz, —CH$_2$CH$_2$OH, 4H), 2.50 (t, J=6.4 Hz, —CH2CH$_2$COOCH$_3$, 2H)

Example 21. Preparation of Diol tBuDP

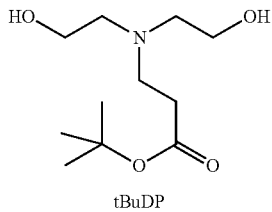 [SMILES: CC(C)(C)OC(=O)CCN(CCO)CCO]

tBuDP

To a 50 mL round bottom flask containing diethanolamine (DEA, 5.1 g, 47.6 mmol, 1.0 equiv.) and magnetic stir bar, tert-butyl acrylate (24.5 g, 0.19 mol, 4.0 equiv.) was added in one portion and the reaction mixture was allowed to stir at room temperature overnight (about 16 hours). Excess tert-butyl acrylate was removed in vacuo to yield the target diol as colorless viscous oil (11.0 g, ~100%). $^1$H NMR (400 MHz, CDCl$_3$, ppm): delta 3.60 (t, J=5.2 Hz, —CH$_2$OH, 4H), 2.80 (br. s, —OH, 2H), 2.78 (t, J=6.2 Hz, —CH$_2$COOtBu, 2H), 2.61 (t, J=5.2 Hz, —CH$_2$CH$_2$OH, 4H), 2.39 (t, J=6.2 Hz, —CH$_2$CH$_2$COOtBu, 2H), 1.44 (s, C(CH$_3$)$_3$, 9H).

Example 22. Preparation of 6-Boc-1,3,6-Dioxazocan-2-One (DXA-Boc)

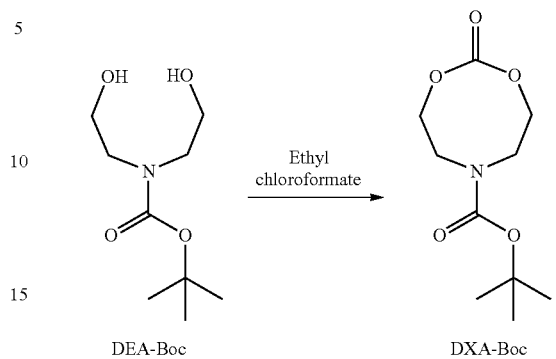

DEA-Boc        DXA-Boc

A round bottom flask was charged with N-Boc-diethanolamine (DEA-Boc, 5.01 g, 24.4 mmol, 1 equivalent), ethyl chloroformate (9.33 mL, 98.0 mmol, 4 equivalents), dry tetrahydrofuran (THF) (600 mL) and a stirbar. The reaction flask was cooled to 0° C. under a nitrogen atmosphere for 30 minutes. Triethylamine (13.7 mL, 98.0 mmol) was added dropwise from an addition funnel to the reaction mixture over the course of 30 minutes. The reaction was allowed to proceed in ice-cold conditions for about 1-2 hours and then allowed to warm up gradually to room temperature, during which a white precipitate formed, and stirring was continued for another 18 hours at room temperature. Filtration of the precipitated HCl salts, followed by concentration of the filtrate gave the crude product as a colorless oil that slowly solidified. Purification by recrystallization from diethyl ether afforded the desired product as a white solid (2.97 g, 53%). $^1$H NMR (400 MHz, CDCl$_3$): delta 4.36 (m, 4H, —OCOCH$_2$—), 3.59 (t, 2H, —CHHNCHH—), 3.52 (t, 2H, —CHHNCHH), 1.46 (s, 9H, Boc C(CH$_3$)$_3$). $^{13}$C NMR (100 MHz, CDCl$_3$, delta, ppm): 155.73, 154.63, 81.10, 69.28, 68.77, 49.07, 48.62 and 28.22.

Example 23. Preparation of Ethyl 2-Oxo-1,3,6-Dioxazocane-6-Carboxylate (DXA-Et)

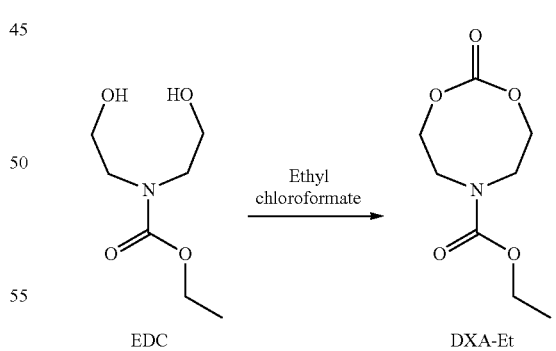

EDC        DXA-Et

The general procedure of Example 22 was followed using ethyl diethanolamine-N-carboxylate (EDC). Isolated yield: 3.1 g (53%); $^1$H NMR (400 MHz, CDCl$_3$, ppm): delta 4.36 (overlapping two set of triplets, J=5.0 Hz, 4H, —CH$_2$OCOOCH$_2$—, a), 4.16 (quartet, J=7.1 Hz, 2H, —CH$_2$CH$_3$, c), 3.62 and 3.57 (overlapping two set of triplets, J=4.9 and 5.0 Hz respectively, 4H, —CH$_2$CH$_2$OCOOCH$_2$CH$_2$—, b), 1.25 (t, J=7.1 Hz, 3H, —CH$_2$CH$_3$, d). $^{13}$C NMR (100 MHz, CDCl$_3$, ppm): delta 155.68, 155.60, 69.25, 68.98, 62.14, 49.35, 48.92 and 14.52.

Example 24. Preparation of Allyl 2-Oxo-1,3,6-Dioxazocane-6-Carboxylate (DXA-Al)

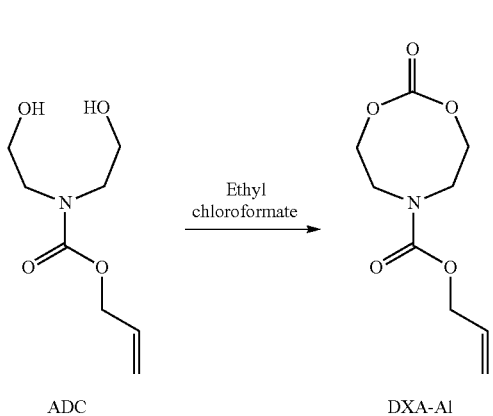

The general procedure of Example 22 was followed using allyl diethanolamine-N-carboxylate (ADC). Isolated yield: 2.4 g (41%); $^1$H NMR (400 MHz, CDCl$_3$, ppm): delta 5.97-5.87 (m, 1H, CH$_2$=CH—), 5.31 and 5.27 (two sets of quartets, J=1.5 Hz, 1H, HC(H)=CH—), 5.24 and 5.22 (two sets of quartets, J=1.3 Hz, 1H, HC(H)=CH—), 4.63-4.60 (m, 2H, CH$_2$=CHCH$_2$—), 4.39 (overlapping two set of triplets, J=4.9 and 5.0 Hz respectively, 4H, —CH$_2$OCOOCH$_2$—), 3.65 and 3.61 (overlapping two set of triplets, J=4.9 and 5.0 Hz respectively, 4H, —CH$_2$CH$_2$OCOCH$_2$CH$_2$—); $^{13}$C NMR (100 MHz, CDCl$_3$, ppm): delta 155.66, 155.31, 132.33, 118.08, 69.27, 69.04, 66.75, 49.64 and 49.08.

Example 25. Preparation of Ethyl 2-Oxo-1,3,6-Dioxazocane-6-Carboxylate (DXA-Et)

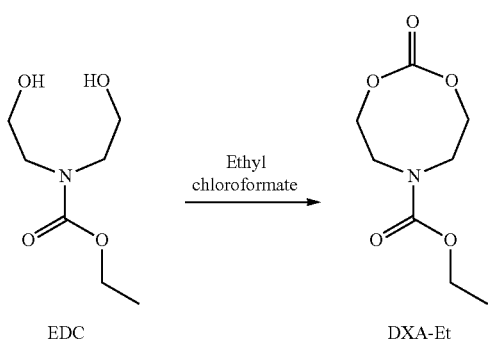

The general procedure of Example 22 was followed using ethyl diethanolamine N-carboxylate (EDC). Isolated yield: 3.1 g (53%); $^1$H NMR (400 MHz, CDCl$_3$, ppm): delta 4.36 (overlapping two set of triplets, J=5.0 Hz, 4H, —CH$_2$OCOOCH$_2$—, a), 4.16 (quartet, J=7.1 Hz, 2H, —CH$_2$CH$_3$, c), 3.62 and 3.57 (overlapping two set of triplets, J=4.9 and 5.0 Hz respectively, 4H, —CH$_2$CH$_2$OCOOCH$_2$CH$_2$—, b), 1.25 (t, J=7.1 Hz, 3H, —CH$_2$CH$_3$, d). $^{13}$C NMR (100 MHz, CDCl$_3$, ppm): delta 155.68, 155.60, 69.25, 68.98, 62.14, 49.35, 48.92 and 14.52.

Example 26. Preparation of 1,3,6-Trioxocan-2-One (TXA)

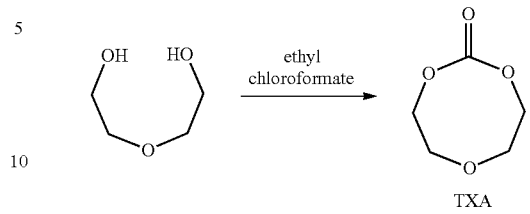

The general procedure of Example 22 was followed using diethylene glycol (5.0 g, 47.1 mmol), ethyl chloroformate (18.0 mL, 189 mmol), dry tetrahydrofuran (THF) (600 mL) and triethylamine (26.5 mL, 190 mmol). Purification of the crude product by recrystallization from 50:5:1 v/v/v diethyl ether: CH$_2$Cl$_2$: MeOH afforded the desired product as a while solid (0.311 g, 5%). $^1$H NMR (400 MHz, CDCl$_3$, ppm): delta 4.29 (t, 4H, —OCOCH$_2$—), 3.72 (t, 4H, —CH$_2$OCH$_2$—).

Example 27. Preparation of Methyl 3-(2-Oxo-1,3,6-Dioxazocan-6-yl)Propanoate (DXA-MeP)

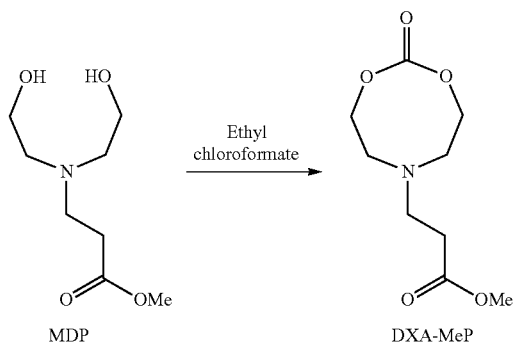

The general procedure of Example 22 was followed using methyl diethanolamine N-propionate (MDP). Isolated yield: 2.4 g (21%); $^1$H NMR (400 MHz, CDCl$_3$, δ, ppm): 4.14 (t, J=5.3 Hz, 4H, —CH$_2$OCOOCH$_2$—), 3.64 (s, 3H, CH$_3$), 2.95 (t, J=7.0 Hz, 2H, —CH$_2$CH$_2$COO CH$_3$), 2.78 (t, J=5.3 Hz, 4H, —CH$_2$CH$_2$OCOOCH$_2$CH$_2$—), 2.41 (t, J=7.0 Hz, 2H, —CH$_2$CH$_2$COOCH$_3$); $^{13}$C NMR (100 MHz, CDCl$_3$, ppm): delta 172.38, 156.03, 68.88, 54.00, 52.52, 51.67 and 32.79.

Example 28. Preparation of T-Butyl 3-(2-Oxo-1,3,6-Dioxazocan-6-yl)Propanoate (DXA-tBuP)

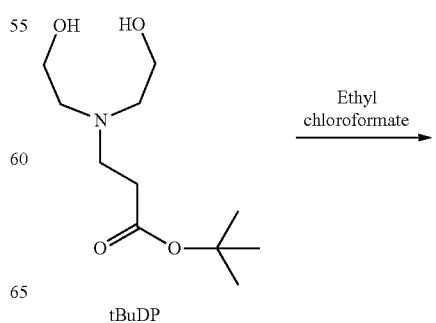

-continued

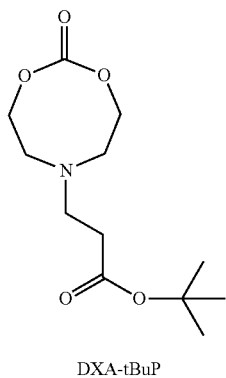

DXA-tBuP

The general procedure of Example 22 was followed using t-butyl diethanolamine N-propionate (tBuDP). Isolated yield: 2.6 g (23%); $^1$H NMR (400 MHz, CDCl$_3$, ppm): delta 4.17 (t, J=5.3 Hz, 4H, —CH$_2$OCOOCH$_2$—), 2.94 (t, J=7.0 Hz, 2H, —CH$_2$CH$_2$COO$^t$Bu), 2.81 (t, J=5.3 Hz, 4H, —CH$_2$CH$_2$OCOOCH$_2$CH$_2$—), 2.37 (t, J=7.0 Hz, 2H, —CH$_2$CH$_2$COO$^t$Bu), 1.42 (s, 9H, —C(CH$_3$)$_3$); $^{13}$C NMR (100 MHz, CDCl$_3$, ppm): delta 171.36, 156.20, 80.67, 68.98, 53.97, 52.40, 34.17 and 27.98.

Polymerizations

Example 29. Preparation of Polymer P-7 by Ring Opening Polymerization of 6-Boc-1,3,6-Dioxazocan-2-One (DXA-Boc)

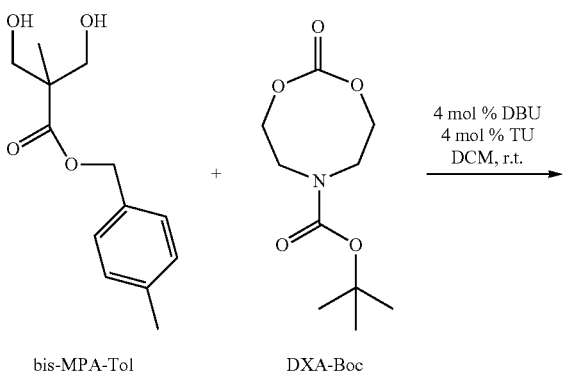

bis-MPA-Tol        DXA-Boc

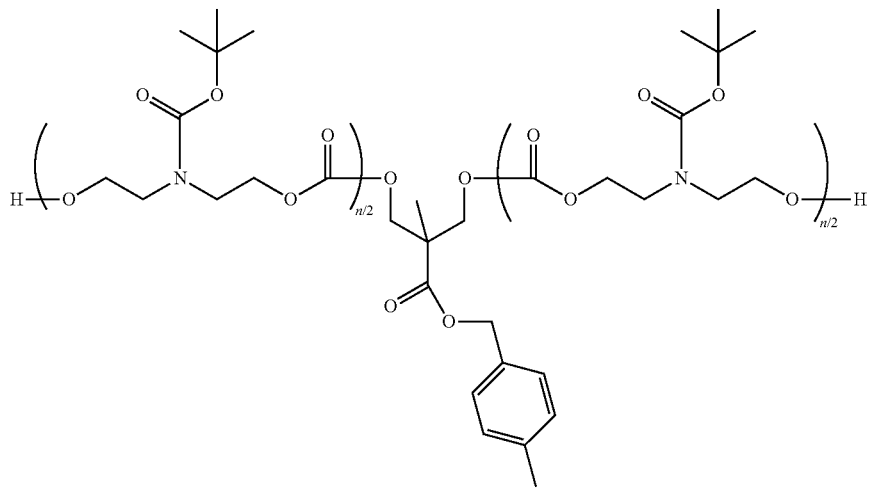

P-7
n = 50

Bis-MPA-Tol can be prepared following the general procedure described above for BnMPA and replacing benzyl alcohol with 4-methylbenzyl alcohol. In a nitrogen-filled glove box, a 4 mL glass vial was charged with DXA-Boc (231 mg, 1.0 mmol), bis-MPA-Tol (4.8 mg, 0.02 mmol), thiourea (TU; 15 mg, 0.04 mmol), a stirbar, and dry dichloromethane (1 mL). The solids were allowed to dissolve, and the polymerization was started by addition of DBU (6.1 mg, 0.04 mmol). After 1 h, the polymerization was terminated by adding benzoic acid (15 mg, 0.12 mmol). Analysis of the crude mixture by 1H NMR spectroscopy indicated that ~90% of the monomer had been consumed. Precipitation from hexane afforded the polymer as a white solid (202 mg, 87% yield). $^1$H NMR (400 MHz, CDCl$_3$, ppm): delta 4.20 (br, 4H, —OCH$_2$—), 3.50 (br, 4H, —CH$_2$NCH$_2$—), 1.44 (s, 9H, Boc C(CH$_3$)$_3$). Mn (GPC): 7447 Da; PDI=1.13.

Example 30. Deprotection of Poly(DXA-Boc)

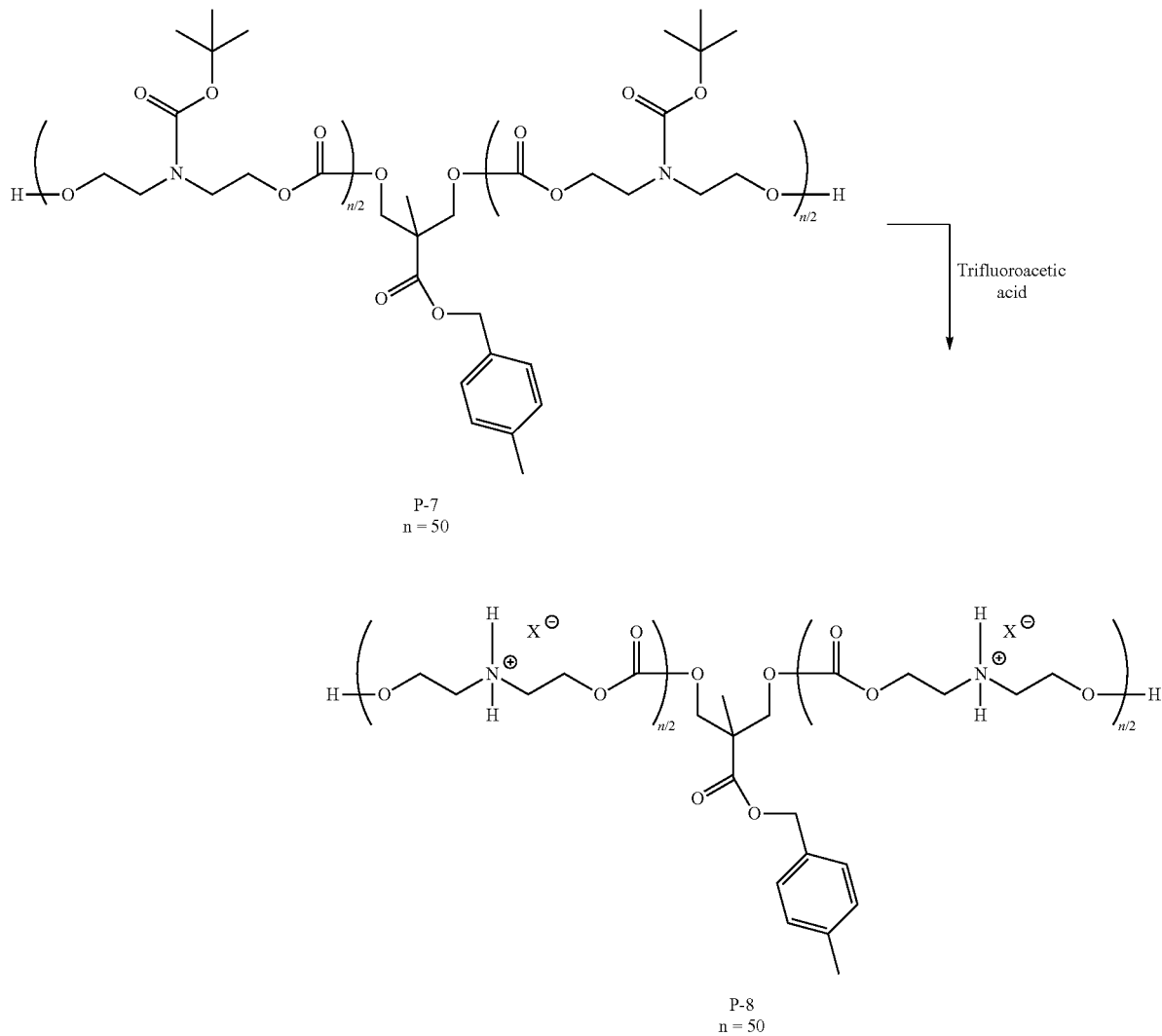

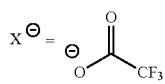

Polymer P-7 (202 mg) was dissolved in dichloromethane (2 mL) in a 4 mL glass vial. Trifluoroacetic acid (TFA; 210 mg, 104 wt % based on weight of P-7) was added, and the mixture was stirred at room temperature for 4 days. Deprotection of the amino groups was confirmed by 1H NMR spectroscopy. $^1$H NMR (400 MHz, CDCl$_3$, ppm): delta 6.02 (br, 2H, —NH$_2$—), 4.47-4.21 (br m, 4H, —OCOCH$_2$—), 3.42 (br, 4H, —CH$_2$NCH$_2$—).

Example 31. Preparation of Polymer P-9 by Ring Opening Polymerization of Allyl 2-Oxo-1,3,6-Dioxazocane-6-Carboxylate (DXA-Al)

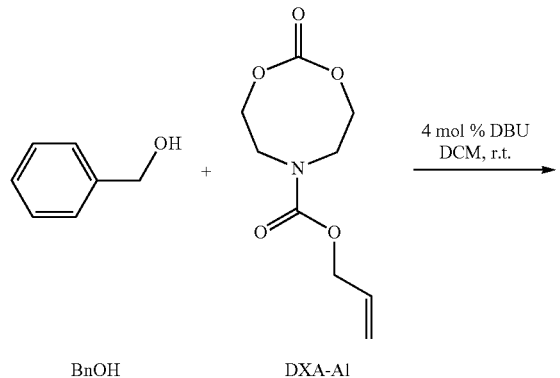

The general procedure of Example 29 was followed using benzyl alcohol as initiator, cyclic monomer DXA-Al, and DBU as catalyst in a molar ration of 1:20:1. The polymerization was terminated after 2 hours. Analysis of the crude mixture by 1H NMR spectroscopy indicated that ~97% of the monomer had been consumed. Mn (GPC): 4330 Da; PDI=1.12.

Example 32. Preparation of Polymer P-10 by Ring Opening Polymerization of Ethyl 2-Oxo-1,3,6-Dioxazocane-6-Carboxylate (DXA-Al)

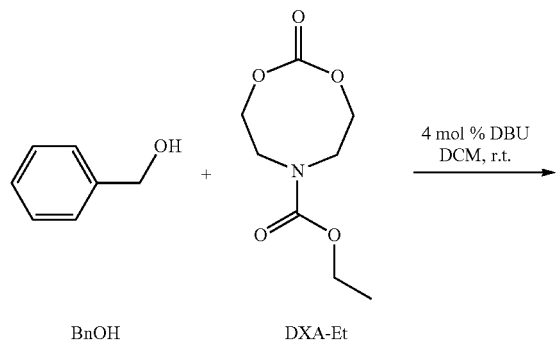

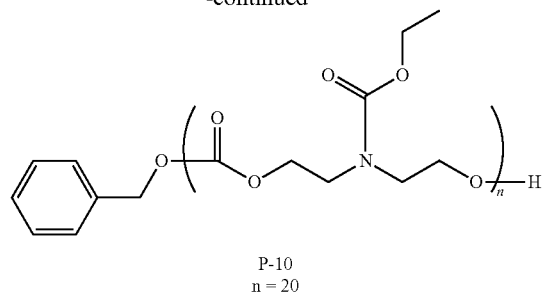

The general procedure of Example 29 was followed using benzyl alcohol as initiator, cyclic monomer DXA-Et, and DBU as catalyst in a molar ration of 1:20:1. The polymerization was terminated after 2 hours. Analysis of the crude mixture by 1H NMR spectroscopy indicated that ~97% of the monomer had been consumed. Mn (GPC): 4270 Da; PDI=1.13.

Example 33. Preparation of Polymer P-11 by Ring Opening Polymerization of Methyl 3-(2-Oxo-1,3,6-Dioxazocan-6-Yl)Propanoate (DXA-MeP)

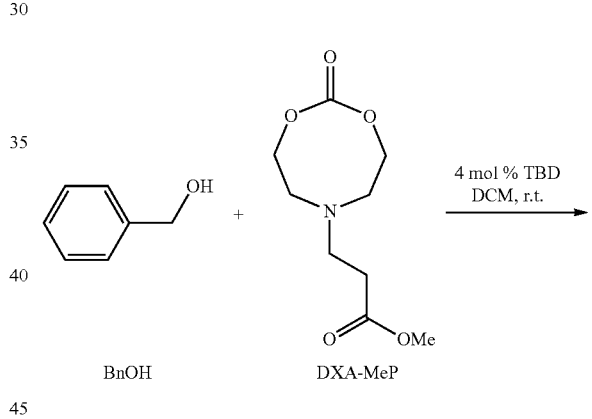

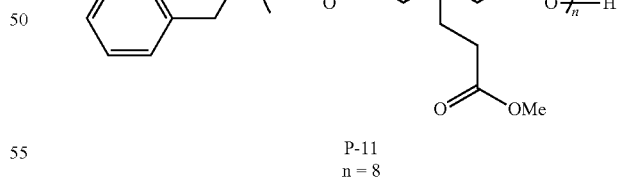

The general procedure of Example 29 was followed using benzyl alcohol as initiator, cyclic monomer DXA-MeP, and 1,5,7-triazabicyclo[4.4.0]dec-5-ene (TBD) as catalyst in a molar ration of 1:20:1. The polymerization was terminated after 2 hours. Analysis of the crude mixture by 1H NMR spectroscopy indicated that ~69% of the monomer had been consumed. Mn (GPC): 1950 Da; PDI=1.19.

Example 34. Preparation of Polymer P-11 by Ring Opening Polymerization of t-Butyl 3-(2-Oxo-1,3,6-Dioxazocan-6-Yl)Propanoate (DXA-tBuP)

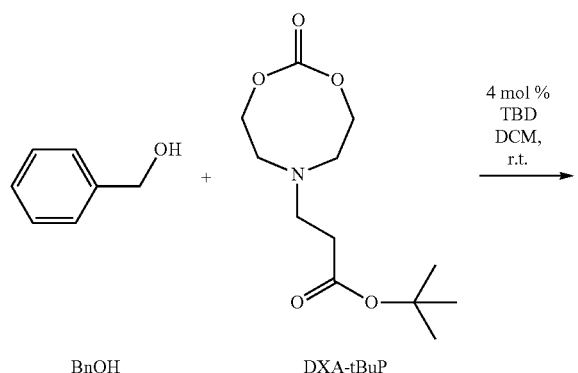

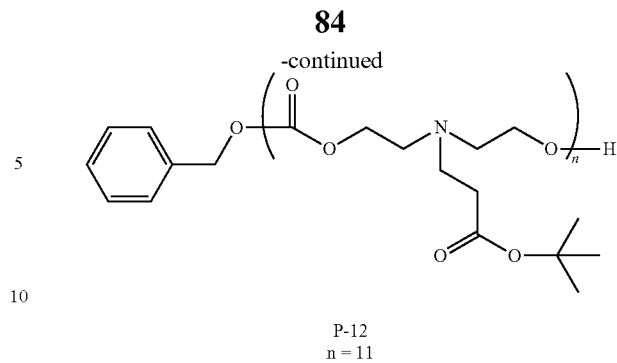

P-12
n = 11

The general procedure of Example 29 was followed using benzyl alcohol as initiator, cyclic monomer DXA-tBuP, and 1,5,7-triazabicyclo[4.4.0]dec-5-ene (TBD) as catalyst in a molar ration of 1:20:1. The polymerization was terminated after 2 hours. Analysis of the crude mixture by 1H NMR spectroscopy indicated that ~71% of the monomer had been consumed. Mn (GPC): 1950 Da; PDI=1.33.

Example 35. Preparation of Block Copolymer P-13 by Sequential Ring Opening Polymerization of DXA pH and DXA tBuP

P-13 m = 12
n = 17

In a 7-mL vial containing a magnetic stir bar, DXA-Ph (112 mg, 540 micromoles, 11.2 equivalents) and benzyl alcohol (5.0 microliters, 5.2 mg, 48.3 micromoles, 1.0 equivalents) were dissolved in DCM (1.0 mL). To this solution, DBU (3.6 microliters, 3.7 mg, 24.2 micromoles, 0.5 equivalents) was added to initiate polymerization. The reaction mixture was allowed to stir at room temperature for 2 hours. After 2 hours, an aliquot (60 microliters) was removed to determine the monomer conversion (found to be about 99% by $^1$H NMR spectroscopy). To the remaining reaction mixture a solution of DXA-tBuP (344 mg, 1330 micromoles, 27.5 equivalents) dissolved in DCM (2.0 mL) was added, followed by additional DBU (54.1 microliters, 55.1 mg, 362 micromoles, 7.5 equivalents). The reaction was allowed to proceed for another 44 hours. The reaction was quenched by the addition of benzoic acid (about 100 mg). The crude block copolymer was purified by precipitating twice into cold diethylether (50 mL). $^1$H NMR (400 MHz, CDCl$_3$, ppm): delta 7.39-7.33 (m, Benzyl, initiator), 7.21 (t, meta-H, Phenyl, polymer), 6.80-6.67 (t, ortho and para-H, Phenyl, polymer), 5.13 (s, CH$_2$, initiator), 4.24 (t, —CH$_2$OCOCH$_2$, of Block 1, phenyl polymer), 4.15 (br. t, —CH$_2$OCOCH$_2$, of Block 2), 3.60 (t, —CH$_2$CH$_2$OCOCH$_2$CH2, of Block 1, phenyl polymer), 3.0-2.60 (br. m, —CH$_2$COOtBu, and CH$_2$CH$_2$OCOOCH$_2$CH$_2$ of polymer, block 2), 2.35 (br. t, —CH$_2$COOtBu of polymer, block 2), 1.45-1.42 (m, C(CH$_3$)$_3$ of polymer block 2); PDI=1.17; m=12; n=17 (based on NMR).

Example 36. Deprotection of P-13

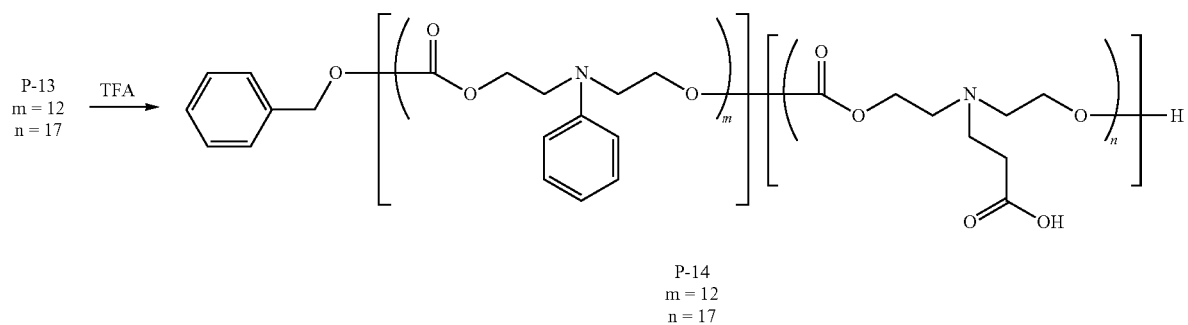

P-14
m = 12
n = 17

Deprotection of the tert-butyl ester groups of P-13 was accomplished by treating P-13 with trifluoroacetic acid (TFA, 10 equivalents, 33% solution in DCM) for 1 hour at room temperature. The crude polymer P-14 was purified by precipitating once into cold diethylether (50 mL). $^1$H NMR (400 MHz, DMSO-d6, ppm): delta 7.40-7.30 (s, Benzyl, initiator), 7.13 (t, meta-H, Phenyl, polymer), 6.74 (m, ortho-H Phenyl, polymer), 6.61 (m, para-H Phenyl, polymer), 5.11 (s, CH$_2$, initiator), 4.42 (t, —CH$_2$OCOCH$_2$, of Block 1, phenyl polymer), 4.16 (br. t, —CH$_2$OCOCH$_2$, of Block 2), 3.55 (t, —CH$_2$CH$_2$OCOCH$_2$CH$_2$, of Block 1, phenyl polymer), 3.50-3.2 (br. m, —CH$_2$COOH, and CH$_2$CH$_2$OCOOCH$_2$ CH$_2$ of polymer, block 2), 2.71 (br. t, —CH$_2$COOH of polymer, block 2).

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. When a range is used to express a possible value using two numerical limits X and Y (e.g., a concentration of X ppm to Y ppm), unless otherwise stated the value can be X, Y, or any number between X and Y.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:

1. A compound of formula (N-12):

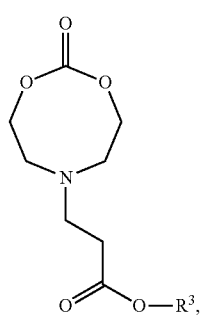

(N-12)

wherein R$^3$ is a hydrocarbyl group comprising 1 to 10 carbons.

2. The compound of claim 1, wherein $R^3$ is selected from the group consisting of methyl, ethyl, n-propyl, iso-propyl, n-butyl, sec-butyl, t-butyl, phenyl, benzyl, and allyl.

3. The compound of claim 1, wherein the compound is

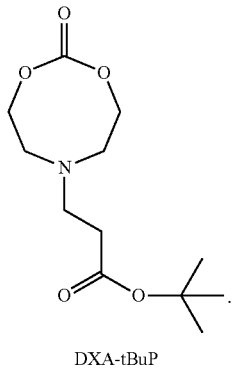 [SMILES: CC(C)(C)OC(=O)CCN1CCOC(=O)OCC1]

DXA-tBuP

4. The compound of claim 1, wherein the compound is

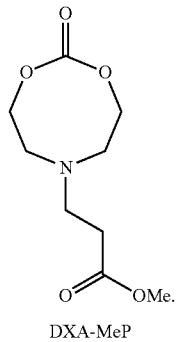 [SMILES: COC(=O)CCN1CCOC(=O)OCC1]

DXA-MeP

5. The compound of claim 1, wherein $R^3$ is ethyl.
6. The compound of claim 1, wherein $R^3$ is n-propyl.
7. The compound of claim 1, wherein $R^3$ is iso-propyl.
8. The compound of claim 1, wherein $R^3$ is n-butyl.
9. The compound of claim 1, wherein $R^3$ is sec-butyl.
10. The compound of claim 1, wherein $R^3$ is phenyl.
11. The compound of claim 1, wherein $R^3$ is benzyl.
12. The compound of claim 1, wherein $R^3$ is allyl.

* * * * *